(12) United States Patent
Kiho et al.

(10) Patent No.: US 11,530,211 B2
(45) Date of Patent: Dec. 20, 2022

(54) DIHYDROINDOLIZINONE DERIVATIVE

(71) Applicant: DAIICHI SANKYO COMPANY, LIMITED, Tokyo (JP)

(72) Inventors: Toshihiro Kiho, Chuo-ku (JP); Tatsuya Yano, Chuo-ku (JP); Satoshi Komoriya, Chuo-ku (JP); Taisaku Tanaka, Chuo-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 16/960,308

(22) PCT Filed: Jan. 18, 2019

(86) PCT No.: PCT/JP2019/001364
§ 371 (c)(1),
(2) Date: Jul. 6, 2020

(87) PCT Pub. No.: WO2019/142883
PCT Pub. Date: Jul. 25, 2019

(65) Prior Publication Data
US 2021/0053965 A1 Feb. 25, 2021

(30) Foreign Application Priority Data

Jan. 18, 2018 (JP) .............................. JP2018-006269

(51) Int. Cl.
| C07D 471/04 | (2006.01) |
| A61P 3/10 | (2006.01) |
| C07D 487/04 | (2006.01) |
| C12N 5/071 | (2010.01) |

(52) U.S. Cl.
CPC .............. *C07D 471/04* (2013.01); *A61P 3/10* (2018.01); *C07D 487/04* (2013.01); *C12N 5/0676* (2013.01); *C12N 2501/73* (2013.01); *C12N 2501/999* (2013.01)

(58) Field of Classification Search
CPC .................................................. C07D 471/04
See application file for complete search history.

(56) References Cited

U.S. PATENT DOCUMENTS

| 7,288,659 B2 | 10/2007 | De Cointet et al. |
| 8,129,182 B2 | 3/2012 | D+3 Amour et al. |
| 8,859,286 B2 | 10/2014 | Agulnick |
| 9,796,962 B2 | 10/2017 | Osafune et al. |
| 10,006,006 B2 | 1/2018 | Rezania |
| 10,000,739 B2 | 6/2018 | Kume et al. |
| 10,190,096 B2 | 1/2019 | Melton et al. |
| 10,253,298 B2 | 4/2019 | Melton et al. |
| 10,443,042 B2 | 10/2019 | Melton et al. |
| 10,772,917 B2 | 9/2020 | Kieffer et al. |
| 2007/0105803 A1 | 5/2007 | Manoharan et al. |
| 2009/0325293 A1 | 12/2009 | Davis et al. |
| 2015/0104430 A1 | 4/2015 | Keller et al. |
| 2016/0175363 A1 | 6/2016 | Melton et al. |
| 2016/0177268 A1 | 6/2016 | Melton et al. |
| 2016/0208215 A1 | 7/2016 | Doehn et al. |
| 2017/0081639 A1 | 3/2017 | Kume et al. |

FOREIGN PATENT DOCUMENTS

| JP | 2003-128551 A | 5/2003 |
| JP | 2009-504782 A | 2/2009 |
| JP | 2011-518563 A | 6/2011 |
| JP | 2017-522347 A | 8/2017 |
| WO | 2012/121168 A1 | 9/2012 |
| WO | 2014/129628 A1 | 8/2014 |
| WO | 2015/125662 A1 | 8/2015 |
| WO | 2016019228 A1 | 2/2016 |

OTHER PUBLICATIONS

Bilguvar, K., et al., "Recessive Loss of Function of the Neuronal Ubiquitin Hydrolase UCHLI Leads to Early-Onset Progressive Neurodegeneration," PNAS 110(9):3489-3494, 2013.
Graham, S.H., et al., "Life and Death in the Trash Heap: The Ubiquitin Proteasome Pathway and UCHLI in Brain Aging, Neurodegenerative Disease and Cerebral Ischemia," Ageing Research Reviews 34:30-38, 2017.
International Search Report dated Mar. 19, 2019, issued in corresponding International Application No. PCT/JP2019/001364, filed Jan. 18, 2019, 3 pages.
Hosoya, M., "Development of the Methods to Prepare Pancreatic β Cells From Human iPS Cells," The CELL 43(12):48 1-484, 2011.
Takeuchi, H., et al., "O-42-5 Establishment of Method for Inducing Differentiation of Insulin-Producing Cells From Human Pluripotent Stem Cells," Regenerative Medicine 12 (Suppl):202,2013.
Taniguchi, H., "Basics and Clinic of GLP-1, Regenerative Medicine and GLP-1," Endocrinology & Diabetology 23(3):267-275, 2006.
Written Opinion dated Mar. 19, 2019, issued in corresponding International Application No. PCT/JP2019/001364, filed Jan. 18, 2019, 5 pages.

(Continued)

*Primary Examiner* — Brian E McDowell
(74) *Attorney, Agent, or Firm* — Christensen O'Connor Johnson Kindness PLLC

(57) ABSTRACT

It is an object of the present invention to provide a new compound capable of efficiently inducing differentiation from pluripotent stem cells into insulin-producing cells. The object of the present invention is achieved by a compound represented by formula (I):

[Formula 1]

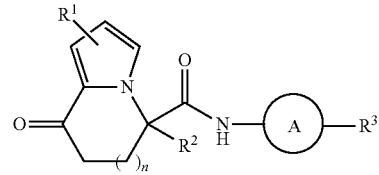

(I)

wherein $R^1$, $R^2$, $R^3$, n and A have the same meanings as defined in the description, respectively, or a salt thereof.

27 Claims, No Drawings

(56) References Cited

OTHER PUBLICATIONS

Shiraki, N. et al., "Methionine Metabolism Regulates Maintenance and Differentiation of Human Pluripotent Stem Cells," Cell Metabolism, 19, 780-794, May 6, 2014.

Shiraki, N. et al., "Guided Differentiation of Embryonic Stem Cells into Pdx1-Expressing Regional-Specific Definitive Endoderm," STEMCELLS 26:874-885, 2008.

Kroon, Evert, et al. "Pancreatic endoderm derived from human embryonic stem cells generates glucose-responsive insulin-secreting cells in vivo." Nature biotechnology 26.4 (2008): 443-452.

Pagliuca, Felicia W., et al. "Generation of functional human pancreatic β cells in vitro." Cell 159.2 (2014): 428-439.

Shahjalal, Hussain Md, et al. "Generation of insulin-producing β-like cells from human iPS cells in a defined and completely xeno-free culture system." Journal of molecular cell biology 6.5 (2014): 394-408.

Kunisada, Yuya, et al. "Small molecules induce efficient differentiation into insulin-producing cells from human induced pluripotent stem cells." Stem cell research 8.2 (2012): 274-284.

Kimura, Azuma, et al. "Small molecule AT7867 proliferates PDX1-expressing pancreatic progenitor cells derived from human pluripotent stem cells." Stem cell research 24 (2017): 61-68.

Rezania, Alireza, et al. "Reversal of diabetes with insulin-producing cells derived in vitro from human pluripotent stem cells." Nature biotechnology 32.11 (2014): 1121-1133.

Office Action dated Mar. 11, 2022, issued in Indian Application No. 202247002538, filed Jan. 17, 2022, 6 pages.

DIHYDROINDOLIZINONE DERIVATIVE

TECHNICAL FIELD

The present invention relates to a compound which promotes differentiation of pluripotent stem cells into insulin-producing cells.

BACKGROUND ART

Diabetes develops with various genetic factors and environmental factors as the background and is a severe disease that significantly reduces the QOL of patients as a result of complications such as nephropathy induced by chronic hyperglycemia. Currently, the number of diabetics in the world exceeds 400 million, which is also problematic in view of medical care economics. Diabetes is roughly classified into type 1 and type 2 diabetes, and loss of pancreatic β cells having an insulin secretory function is a major cause in both pathological conditions. Administration of insulin preparations is a common method for treating type 1 diabetes and severe type 2 diabetes with significant loss of pancreatic β cells, but there are many problems such as side effects including hypoglycemia and the necessity of frequent self-injection. In recent years, transplantation of pancreatic islet cells isolated from an organ donor into a type 1 diabetic patient has become possible and is expected as a treatment method which replaces insulin treatment and enables complete remission of diabetes. However, wide adoption is difficult due to lack of pancreatic islet donors. Therefore, it is desired to urgently realize a technique for producing insulin-producing cells in a large amount from pluripotent stem cells.

As a technique for producing insulin-producing cells from pluripotent stem cells, a method of inducing differentiation of ES cells or iPS cells into insulin-producing cells through a 5-stage to 7-stage process using a compound represented by the following formula has been reported (Patent Document 1 and Non Patent Documents 1, 2, 3, 4, and 5). In the method of Shahjalal, et al. (Patent Document 1 and Non Patent Document 4), insulin-producing cells can be produced from human iPS cells stepwise through a 5-stage differentiation process. First, iPS cells grown in a maintenance medium are cultured in a medium containing activin A or the GSK3β inhibitor CHIR99201 for several days in stage 1, to induce Sox17-positive definitive endoderm cells. In stage 2, the definitive endoderm cells are treated with FGF10 or the sonic hedgehog inhibitor KAAD-cyclopamine for several days, to induce Foxa2-positive primitive gut tube cells. Further, in stage 3, the primitive gut tube cells are treated with a medium containing retinoic acid, KAAD-cyclopamine, the TGFβ receptor kinase inhibitor SB431542, and the BMP signal inhibitor Noggin for several days, to induce differentiation into PDX1-positive pancreatic progenitor cells. In stage 4, the pancreatic progenitor cells are stimulated with the protein kinase C activator indolactam V, ALk5 inhibitor II that is a TGFβ receptor kinase inhibitor, and Noggin, to induce Ngn3-positive pancreatic endocrine progenitor cells. In stage 5 of the final stage, the pancreatic endocrine progenitor cells are cultured in a medium containing a GLP-1 receptor agonist and nicotinamide for several days. Thereby, insulin-producing cells are obtained.

[Formula 1]

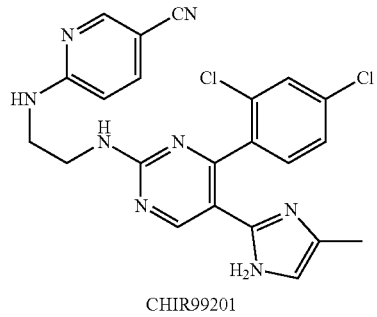

CHIR99201

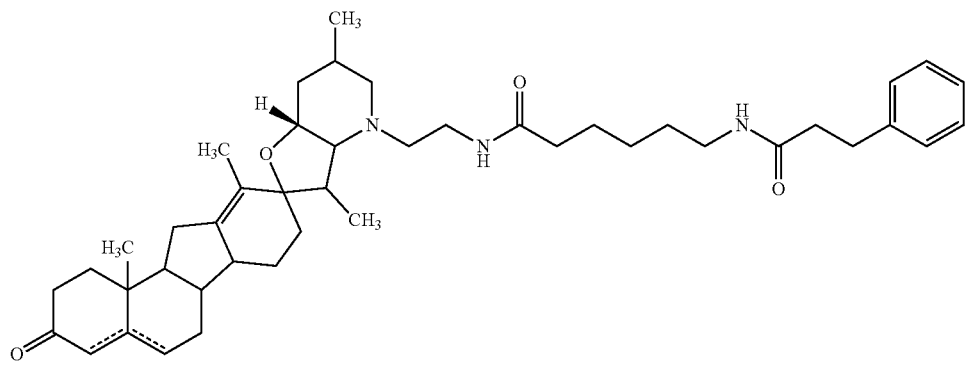

KAAD-cyclopamine

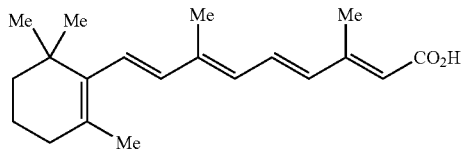

Retinoic acid

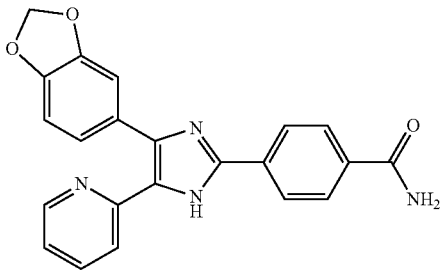

SB431542

Further, there is a report using a compound represented by the following formula. There may be cases of using the small molecule inhibitor LDN193189, instead of Noggin used in the aforementioned differentiation culture, and SANT-1 (Non Patent Documents 2 and 6) or Dorsomorphin (Non Patent Document 5), instead of KAAD-cyclopamine. Further, in the final step of the differentiation culture, there may be cases of using Forskolin or Dexamethasone as a differentiation inducer (Non Patent Document 5). Other than the above, the AXL inhibitor R428 is reported as a compound that promotes the functional maturation of insulin-producing cells (Non Patent Document 3), and the AKT inhibitor AT7867 is reported as a compound that promotes the growth of PDX-1-positive pancreatic progenitor cells (Non Patent Document 7).

[Formula 2]

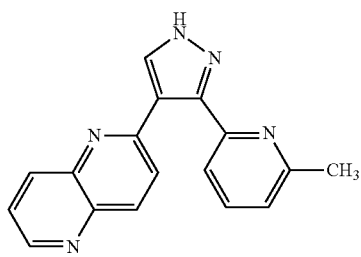

Indolactam V

-continued

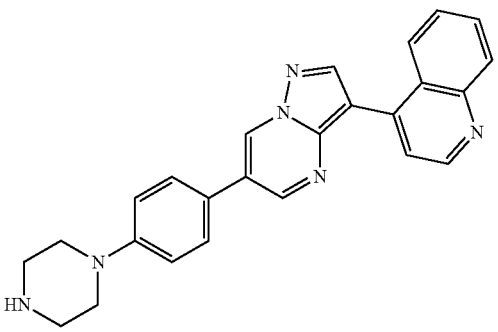

LDN193189

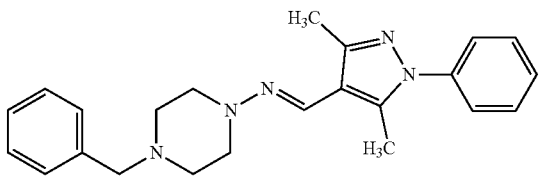

SANT-1

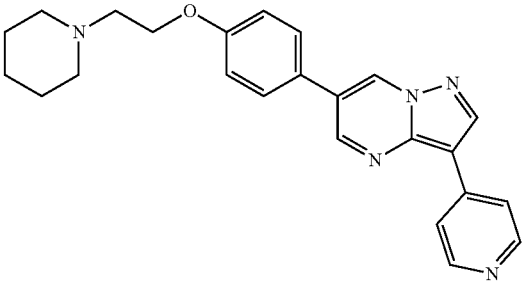

Dorsomorphin

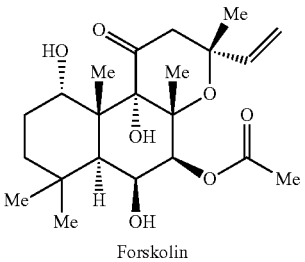

ALK5 inhibitor II

Forskolin

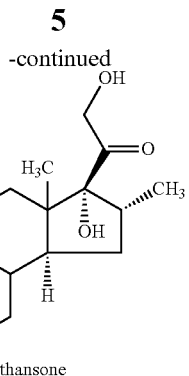

Dexamethansone

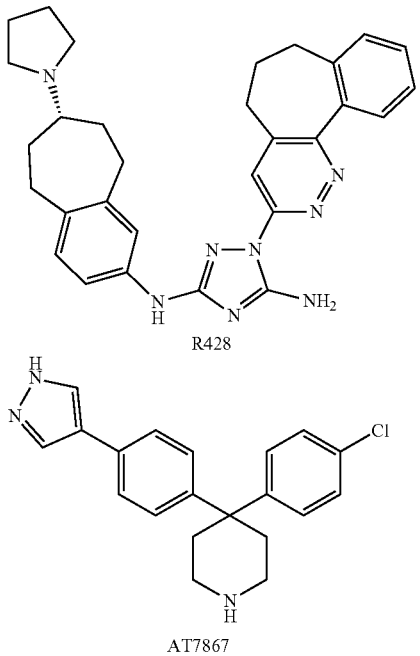

R428

AT7867

In order to apply insulin-producing cells derived from pluripotent stem cells to cell therapy, the stability of cell functions and the efficiency of the production method are important. The stability of cell functions means that the insulin-producing cells obtained exhibit good reproducibility and constant ability in the ability to secrete insulin in response to high glucose and the insulin secretion dynamics in each experiment. These abilities vary depending on the production lot or cell line in the cells obtained by a conventional method, and it is thus difficult to ensure a stable quality, which is a problem. Concerning the efficiency of the production method, there is a problem of poor cost efficiency in conventional methods due to the small number of insulin-producing cells capable of inducing differentiation.

Ubiquitin C-terminal hydrolase (Ubiquitin C-terminal Hydrolase L1; which will be hereinafter referred to as UCHL1) is one of the ubiquitin hydrolases that hydrolyze a bond between ubiquitin and a small adduct bound to its C-terminus and have a role of generating ubiquitin monomers. UCHL1 is highly expressed in nerve cells or neuroendocrine cells and has been suggested to be relevant to neurodegenerative diseases such as Alzheimer's disease and Parkinson's disease (Non Patent Document 8). Further, this enzyme is also highly expressed in pancreatic β cells and has been reported to play an important role in the survival and functions of the cells. Therefore, it is inferred that the enzyme may be involved also in the differentiation or development process of the cells (Non Patent Documents 9 and 10).

CITATION LIST

Patent Documents

Patent Document 1: International Application Publication No. 2015/178397

Non Patent Documents

Non Patent Document 1: Kroon, E. et al., Pancreatic endoderm derived from human embryonic stem cells generates glucose-responsive insulin-secreting cells in vivo. Nature Biotechnology, 26: 443-452, 2008.
Non Patent Document 2: Pagliuca F. W., et al., Generation of functional human pancreatic β cells in vitro. Cell, 159: 428-439, 2014.
Non Patent Document 3: Rezania A. et al., Reversal of diabetes with insulin-producing cells derived in vitro from human pluripotent stem cells. Nature Biotechnology, 32: 1122-1133, 2014.
Non Patent Document 4: Shahjalal H. et al., Generation of insulin-producing β-like cells from human iPS cells in a defined and completely xeno-free culture system. Journal of Molecular Cell Biology, 6: 394-408, 2014.
Non Patent Document 5: Kunisada Y. et al., Small molecules induce efficient differentiation into insulin-producing cells from human induced pluripotent stem cells. Stem Cell Research, 8: 274-284, 2012.
Non Patent Document 6: Nakashima R. et al., Neural cells play an inhibitory role in pancreatic differentiation of pluripotent stem cells. Genes Cells, 20: 1028-1045, 2015.
Non Patent Document 7: Kimura A. et al., Small molecule AT7867 proliferates PDX1-expressing pancreatic progenitor cells derived from human pluripotent stem cells. Stem Cell Research, 24: 61-68, 2017.
Non Patent Document 8: Setsuie R. et al., The functions of UCH-L1 and its relation to neurodegenerative diseases. Neurochemistry International, 51: 105-111, 2007.
Non Patent Document 9: Costes S. et al., β-Cell Dysfunctional ERAD/Ubiquitin/Proteasome System in Type 2 Diabetes Mediated by Islet Amyloid Polypeptide-Induced UCH-L1 Deficiency. Diabetes, 2011, January; 60(1): 227-38.
Non Patent Document 10: Chu K. Y. et al., Ubiquitin C-terminal hydrolase L1 is required for pancreatic beta cell survival and function in lipotoxic conditions. Diabetologia, 2012, January; 55(1): 128-40.

SUMMARY OF INVENTION

Technical Problem

An object of the present invention is to provide a small molecule compound achieving high differentiation efficiency from stem cells into insulin-producing cells, which has been difficult with conventional techniques. Further, another object of the present invention is to provide a method for treating and/or preventing diabetes or a neurodegenerative disease by activating UCHL1, which has been difficult with conventional small molecule compounds.

Solution to Problem

As a result of diligent studies, the inventors have found that a compound represented by formula (I) or a salt thereof has a remarkable effect of promoting induction of differentiation from pluripotent stem cells into insulin-producing cells, and further the compound or a salt thereof is useful for producing insulin-producing cells, thereby accomplishing the present invention. The compound of the present invention has a new structure that is completely different from known differentiation inducers and exerts an effect of further enhancing the efficiency of the induction of differentiation in the later steps of the differentiation process more than known differentiation-promoting compounds and growth factors. Further, the inventors have found that the compound represented by formula (I) or a salt thereof has an action to activate UCHL1 and can treat and/or prevent diabetes or neurodegenerative disease, thereby accomplishing the present invention.

That is, the present invention relates to [1] to [25] described below.

[1] A compound represented by formula (I):

[Formula 3]

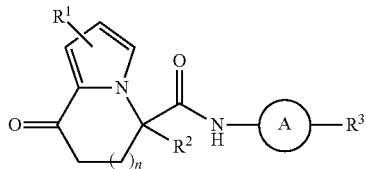

(I)

wherein each substituent is defined as follows:

$R^1$ represents a hydrogen atom, a halogen atom, or a C1-C6 alkyl group;

$R^2$ represents a hydrogen atom or a C1-C6 alkyl group;

$R^3$ represents an aryl group, a C5-C10 cycloalkenyl group, or a heterocyclyl group, each of which is optionally substituted with one to four substituents independently selected from a substituent group α;

the substituent group α includes a halogen atom, a cyano group, a carboxyl group, a C1-C6 alkyl group, a C1-C6 alkoxy group, a halo-C1-C6 alkyl group, a halo-C1-C6 alkoxy group, a hydroxy C1-C6 alkyl group, a C1-C6 alkoxy C1-C6 alkoxy group, a (C1-C6 alkyl)carbonyl group, a (C1-C6 alkoxy)carbonyl group, a (C1-C6 alkoxy)carbonyloxy group, a phenyl C1-C6 alkoxy group, a non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, and a phenoxy group, a phenyl group, and a benzoyl group, which are each optionally substituted with one to four substituents independently selected from a substituent group β;

the substituent group β includes a halogen atom, a C1-C6 alkyl group, a C1-C6 alkoxy group, a halo-C1-C6 alkyl group, a halo-C1-C6 alkoxy group, or a (C1-C6 alkoxy)carbonyl group;

n represents 0 or 1; and

A represents a group represented by any one of formulae (i) to (iv) below:

[Formula 4]

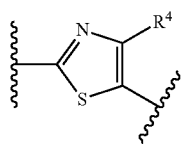

(i)

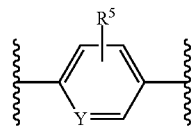

(ii)

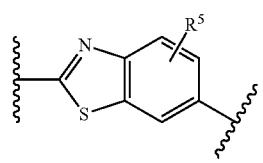

(iii)

(iv)

wherein each substituent is defined as follows:

$R^4$ represents a hydrogen atom, a C1-C6 alkyl group, or a halo-C1-C6 alkyl group;

$R^5$ represents a hydrogen atom, a halogen atom, or a C1-C6 alkyl group; and

Y represents N or CH; or a salt thereof.

[2] A compound according to [1], wherein $R^3$ represents a naphthyl group, a 1,3-benzodioxolyl group, a 2,2-dihalo-1,3-benzodioxolyl group, a C5-C10 cycloalkenyl group, or a phenyl group or a 5- or 6-membered heterocyclyl group, each of which is optionally substituted with one or two substituents independently selected from a substituent group α1;

the substituent group α1 includes a halogen atom, a cyano group, a carboxyl group, a phenoxy group, a benzoyl group, a C1-C6 alkyl group, a C1-C6 alkoxy group, a halo-C1-C6 alkyl group, a halo-C1-C6 alkoxy group, a hydroxy C1-C6 alkyl group, a C1-C6 alkoxy C1-C6 alkoxy group, a (C1-C6 alkyl)carbonyl group, a (C1-C6 alkoxy)carbonyl group, a (C1-C6 alkoxy)carbonyloxy group, a phenyl C1-C6 alkoxy group, a 5- or 6-membered non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, and a phenyl group optionally substituted with one or two substituents independently selected from a substituent group β1; and the substituent group β1 includes a halogen atom, a C1-C6 alkyl group, a C1-C6 alkoxy group, and a (C1-C6 alkoxy)carbonyl group; or a salt thereof.

[3] A compound according to [1], wherein $R^3$ represents a naphthyl group, a 1,3-benzodioxolyl group, a 2,2-dihalo-1,3-benzodioxolyl group, a C5-C10 cycloalkenyl group, a phenyl group optionally substituted with one or two substituents independently selected from a substituent group α2, or a 5- or 6-membered heterocyclyl group optionally substituted with one or two substituents independently selected from a substituent group γ2;

the substituent group α2 includes a halogen atom, a cyano group, a carboxyl group, a phenoxy group, a benzoyl group, a C1-C6 alkyl group, a C1-C6 alkoxy group, a halo-C1-C6 alkyl group, a halo-C1-C6 alkoxy group, a hydroxy C1-C6 alkyl group, a C1-C6 alkoxy C1-C6 alkoxy group, a (C1-C6 alkyl)carbonyl group, a (C1-C6 alkoxy)carbonyl group, a (C1-C6 alkoxy)carbonyloxy group, a phenyl C1-C6 alkoxy group, a 5- or 6-membered non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, and a phenyl group optionally substituted with one or two substituents independently selected from a substituent group β2;

the substituent group β2 includes a halogen atom, a C1-C6 alkyl group, and a C1-C6 alkoxy group; and the substituent group γ2 includes a halogen atom, a C1-C6 alkyl group, a C1-C6 alkoxy group, a (C1-C6 alkyl)carbonyl group, and a (C1-C6 alkoxy)carbonyl group, or a salt thereof.

[4] A compound according to [1], wherein

R³ represents a naphthyl group, a 1,3-benzodioxolyl group, a 2,2-difluoro-1,3-benzodioxolyl group, a C5-C8 cycloalken-1-yl group, a phenyl group optionally substituted with one or two substituents independently selected from a substituent group α3, or a 5- or 6-membered heterocyclyl group optionally substituted with one or two substituents independently selected from a substituent group γ3;

the substituent group α3 includes a halogen atom, a cyano group, a carboxyl group, a phenoxy group, a benzoyl group, a C1-C4 alkyl group, a C1-C4 alkoxy group, a halo-C1-C2 alkyl group, a halo-C1-C2 alkoxy group, a hydroxy C1-C4 alkyl group, a C1-C2 alkoxy C1-C2 alkoxy group, a (C1-C4 alkyl)carbonyl group, a (C1-C4 alkoxy)carbonyl group, a (C1-C4 alkoxy)carbonyloxy group, a phenyl C1-C4 alkoxy group, a morpholin-1-yl group, a carbamoyl group optionally substituted with one or two C1-C4 alkyl groups, a C1-C2 alkoxy group substituted by a carbamoyl group optionally substituted with one or two C1-C4 alkyl groups, a sulfamoyl group substituted with one or two C1-C4 alkyl groups, and a phenyl group optionally substituted with one or two substituents independently selected from a substituent group β3;

the substituent group β3 includes a fluorine atom, a chlorine atom, a C1-C4 alkyl group, and a C1-C4 alkoxy group; and the substituent group γ3 includes a halogen atom, a C1-C4 alkyl group, a C1-C4 alkoxy group, a (C1-C4 alkyl)carbonyl group, and a (C1-C4 alkoxy)carbonyl group, or a salt thereof.

[5] A compound according to any one of [1] to [4], wherein R² represents a hydrogen atom, a chlorine atom, or a methyl group, or a salt thereof.

[6] A compound according to any one of [1] to [5], wherein R² represents a hydrogen atom or a methyl group, or a salt thereof.

[7] A compound according to any one of [1] to [6], wherein A represents a group represented by formula (i), and R⁴ represents a hydrogen atom, a methyl group, or a trifluoromethyl group, or a salt thereof.

[8] A compound according to any one of [1] to [6], wherein A represents a group represented by formula (ii), and R⁵ represents a hydrogen atom, a fluorine atom, or a methyl group, or a salt thereof.

[9] A compound according to any one of [1] to [6], wherein A represents a group represented by formula (iii), and R⁵ represents a hydrogen atom, a fluorine atom, or a methyl group, or a salt thereof.

[10] A compound according to any one of [1] to [9], wherein n represents 1, or a salt thereof.

[11] A compound according to any one of [1] to [10], wherein R³ represents a 2,2-difluoro-1,3-benzodioxolyl group, a 1-tert-butoxycarbonyl-3,6-dihydro-2H-pyridin-4-yl group, or a phenyl group optionally substituted with one or two substituents independently selected from the group consisting of a fluorine atom, a chlorine atom, a trifluoromethyl group, a tert-butoxy group, a trifluoromethoxy group, a 2,2,2-trifluoroethoxy group, a benzyloxy group, and a phenoxy group, or a salt thereof.

[12] A compound according to [1], which is any one selected from the compound group shown below:

[Formula 5]

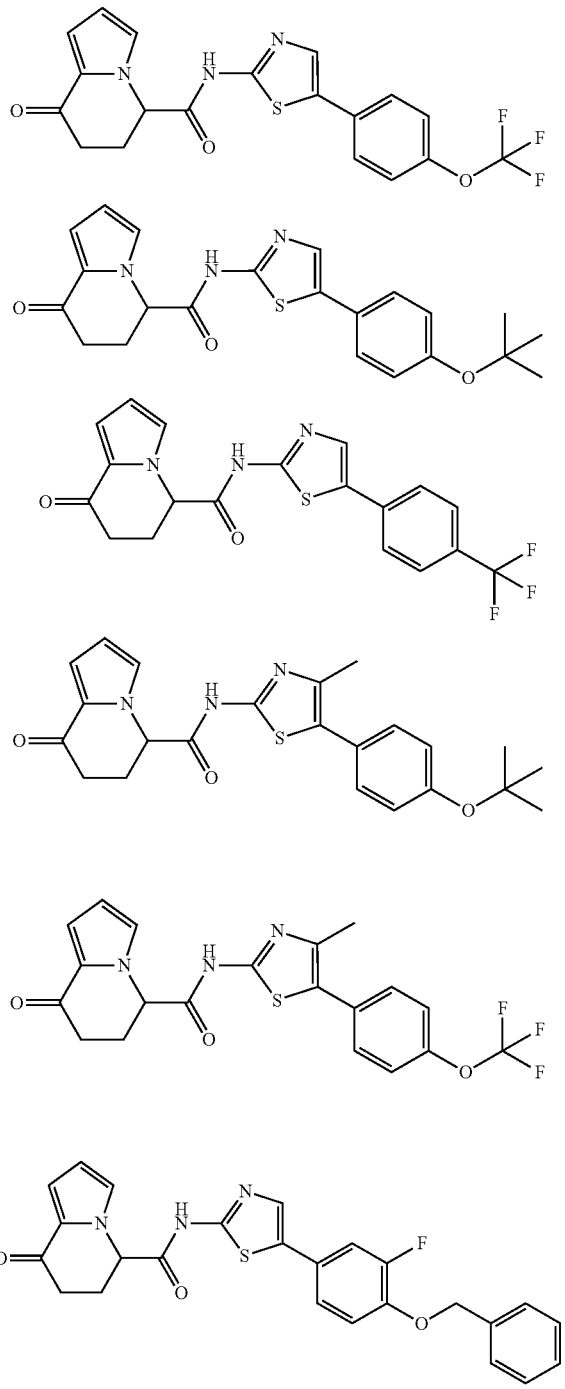

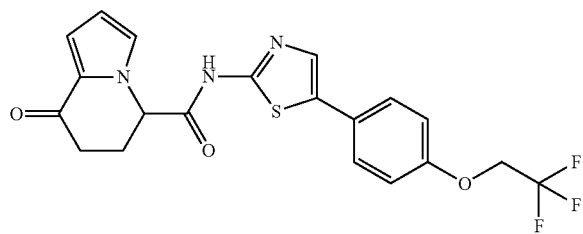

or a salt thereof.

[13] A compound according to [1], represented by the below formula:

[Formula 6]

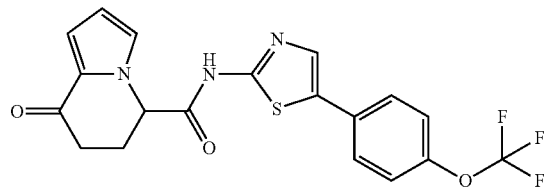

or a salt thereof.

[14] A compound according to [1] represented by the below formula:

[Formula 7]

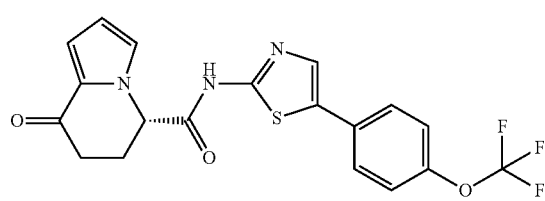

or a salt thereof.

[15] A compound according to [1] represented by the below formula:

[Formula 8]

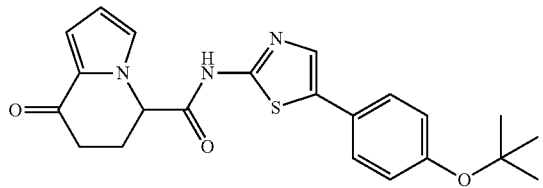

or a salt thereof.

[16] A compound according to [1] represented by the below formula:

[Formula 9]

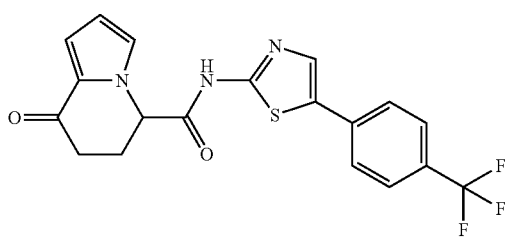

or a salt thereof.

[17] A compound according to [1] represented by the below formula:

[Formula 10]

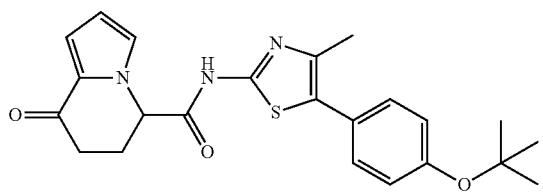

or a salt thereof.

[18] A compound according to [1] represented by the below formula:

[Formula 11]

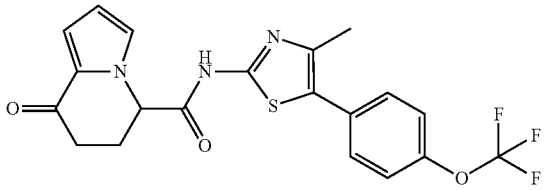

or a salt thereof. [19] A compound according to [1] represented by the below formula:

[Formula 12]

or a salt thereof.

[20] A compound according to [1] represented by the below formula:

[Formula 13]

or a salt thereof.

[21] A compound according to [1] represented by the below formula:

[Formula 14]

or a salt thereof.

[22] A compound according to any one of [1] to [21] or a salt thereof, for differentiating pluripotent stem cells into insulin-producing cells.

[23] Use of a compound according to any one of [1] to [21] or a salt thereof for differentiating pluripotent stem cells into insulin-producing cells.

[24] A method for differentiating pluripotent stem cells into insulin-producing cells, using a compound according to any one of [1] to [21] or a salt thereof.

[25] A method for producing insulin-producing cells, using a compound according to any one of [1] to [21] or a salt thereof.

Further, the present invention relates to [A-1] to [A-48] below according to other aspects.

[A-1] A compound represented by formula (I):

[Formula 15]

(I)

wherein each substituent is defined as follows:
$R^1$ represents a hydrogen atom, a halogen atom, or a C1-C6 alkyl group;
$R^2$ represents a hydrogen atom or a C1-C6 alkyl group;
$R^3$ represents an aryl group optionally substituted with one to four substituents independently selected from a substituent group α, a C5-C10 cycloalkenyl group optionally substituted with one to four substituents independently selected from the substituent group α, or a heterocyclyl group optionally substituted with one to four substituents independently selected from the substituent group α;

the substituent group α includes a halogen atom, a cyano group, a carboxyl group, a C1-C6 alkyl group, a C1-C6 alkoxy group, a halo-C1-C6 alkyl group, a halo-C1-C6 alkoxy group, a hydroxy C1-C6 alkyl group, a C1-C6 alkoxy C1-C6 alkoxy group, a (C1-C6 alkyl)carbonyl group, a (C1-C6 alkoxy)carbonyl group, a (C1-C6 alkoxy)carbonyloxy group, a phenyl C1-C6 alkoxy group, a non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, a phenoxy group optionally substituted with one to four substituents independently selected from a substituent group β, a phenyl group optionally substituted with one to four substituents independently selected from the substituent group β, and a benzoyl group optionally substituted with one to four substituents independently selected from the substituent group β;

the substituent group β includes a halogen atom, a C1-C6 alkyl group, a C1-C6 alkoxy group, a halo-C1-C6 alkyl group, a halo-C1-C6 alkoxy group, and a (C1-C6 alkoxy) carbonyl group;

n represents 0 or 1; and

A represents a group represented by any one of formulae (i) to (iv) below:

[Formula 16]

(i)

(ii)

(iii)

(iv)

wherein each substituent is defined as follows:
• and * each represent a bond, where • is bonded to a nitrogen atom in an amido group of formula (I), and * is bonded to $R^3$;
$R^4$ represents a hydrogen atom, a C1-C6 alkyl group, a halo-C1-C6 alkyl group, or a (C1-C6 alkoxy)carbonyl group;
$R^5$ represents a hydrogen atom, a halogen atom, or a C1-C6 alkyl group; and
Y represents N or CH, or a salt thereof.

[A-2] A compound according to [A-1], wherein

R³ represents a naphthyl group, a 1,3-benzodioxolyl group, a 2,2-dihalo-1,3-benzodioxolyl group, a C5-C10 cycloalkenyl group, a phenyl group optionally substituted with one or two substituents independently selected from a substituent group α1, or a 5- or 6-membered heterocyclyl group optionally substituted with one or two substituents independently selected from the substituent group α1;

the substituent group α1 includes a halogen atom, a cyano group, a carboxyl group, a phenoxy group, a benzoyl group, a C1-C6 alkyl group, a C1-C6 alkoxy group, a halo-C1-C6 alkyl group, a halo-C1-C6 alkoxy group, a hydroxy C1-C6 alkyl group, a C1-C6 alkoxy C1-C6 alkoxy group, a (C1-C6 alkyl)carbonyl group, a (C1-C6 alkoxy)carbonyl group, a (C1-C6 alkoxy)carbonyloxy group, a phenyl C1-C6 alkoxy group, a 5- or 6-membered non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, and a phenyl group optionally substituted with one or two substituents independently selected from a substituent group β1; and the substituent group β1 includes a halogen atom, a C1-C6 alkyl group, a C1-C6 alkoxy group, and a (C1-C6 alkoxy)carbonyl group, or a salt thereof.

[A-3] A compound according to [A-1], wherein

R³ represents a naphthyl group, a 1,3-benzodioxolyl group, a 2,2-dihalo-1,3-benzodioxolyl group, a C5-C10 cycloalkenyl group, a phenyl group optionally substituted with one or two substituents independently selected from a substituent group α2, or a 5- or 6-membered heterocyclyl group optionally substituted with one or two substituents independently selected from a substituent group γ2;

the substituent group α2 includes a halogen atom, a cyano group, a carboxyl group, a phenoxy group, a benzoyl group, a C1-C6 alkyl group, a C1-C6 alkoxy group, a halo-C1-C6 alkyl group, a halo-C1-C6 alkoxy group, a hydroxy C1-C6 alkyl group, a C1-C6 alkoxy C1-C6 alkoxy group, a (C1-C6 alkyl)carbonyl group, a (C1-C6 alkoxy)carbonyl group, a (C1-C6 alkoxy)carbonyloxy group, a phenyl C1-C6 alkoxy group, a 5- or 6-membered non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, and a phenyl group optionally substituted with one or two substituents independently selected from a substituent group β2;

the substituent group β2 includes a halogen atom, a C1-C6 alkyl group, and a C1-C6 alkoxy group; and the substituent group γ2 includes a halogen atom, a C1-C6 alkyl group, a C1-C6 alkoxy group, a (C1-C6 alkyl)carbonyl group, and a (C1-C6 alkoxy)carbonyl group, or a salt thereof.

[A-4] A compound according to [A-1], wherein

R³ represents a naphthyl group, a 1,3-benzodioxolyl group, a 2,2-difluoro-1,3-benzodioxolyl group, a C5-C8 cycloalken-1-yl group, a phenyl group optionally substituted with one or two substituents independently selected from a substituent group α3, or a 5- or 6-membered heterocyclyl group optionally substituted with one or two substituents independently selected from a substituent group γ3;

the substituent group α3 includes a halogen atom, a cyano group, a carboxyl group, a phenoxy group, a benzoyl group, a C1-C4 alkyl group, a C1-C4 alkoxy group, a halo-C1-C2 alkyl group, a halo-C1-C2 alkoxy group, a hydroxy C1-C4 alkyl group, a C1-C2 alkoxy C1-C2 alkoxy group, a (C1-C4 alkyl)carbonyl group, a (C1-C4 alkoxy)carbonyl group, a (C1-C4 alkoxy)carbonyloxy group, a phenyl C1-C4 alkoxy group, a morpholin-1-yl group, a carbamoyl group optionally substituted with one or two C1-C4 alkyl groups, a C1-C2 alkoxy group substituted by a carbamoyl group optionally substituted with one or two C1-C4 alkyl groups, a sulfamoyl group substituted with one or two C1-C4 alkyl groups, and a phenyl group optionally substituted with one or two substituents independently selected from a substituent group β3;

the substituent group β3 includes a fluorine atom, a chlorine atom, a C1-C4 alkyl group, and a C1-C4 alkoxy group; and the substituent group γ3 includes a halogen atom, a C1-C4 alkyl group, a C1-C4 alkoxy group, a (C1-C4 alkyl)carbonyl group, and a (C1-C4 alkoxy)carbonyl group, or a salt thereof.

[A-5] A compound according to any one of [A-1] to [A-4], wherein R² represents a hydrogen atom, a chlorine atom, or a methyl group, or a salt thereof.

[A-6] A compound according to any one of [A-1] to [A-5], wherein R² represents a hydrogen atom or a methyl group, or a salt thereof.

[A-7] A compound according to any one of [A-1] to [A-6], wherein A represents a group represented by formula (i), and R⁴ represents a hydrogen atom, a C1-C6 alkyl group, a halo-C1-C6 alkyl group, or a (C1-C6 alkoxy)carbonyl group, or a salt thereof.

[A-8] A compound according to [A-7], wherein R⁴ represents a hydrogen atom, a methyl group, or a trifluoromethyl group, or a salt thereof.

[A-9] A compound according to any one of [A-1] to [A-6], wherein A represents a group represented by formula (ii), and R⁵ represents a hydrogen atom, a halogen atom, or a C1-C6 alkyl group, or a salt thereof.

[A-10] A compound according to [A-9], wherein R⁵ represents a hydrogen atom, a fluorine atom, or a methyl group, or a salt thereof.

[A-11] A compound according to any one of [A-1] to [A-6], wherein A represents a group represented by formula (iii), and R⁵ represents a hydrogen atom, a fluorine atom, or a methyl group, or a salt thereof.

[A-12] A compound according to any one of [A-1] to [A-6], wherein A represents a group represented by formula (iv), or a salt thereof.

[A-13] A compound according to any one of [A-1] to [A-12], wherein n represents 1, or a salt thereof.

[A-14] A compound according to any one of [A-1] to [A-13], wherein R³ represents a 2,2-difluoro-1,3-benzodioxolyl group, a 1-tert-butoxycarbonyl-3,6-dihydro-2H-pyridin-4-yl group, or a phenyl group optionally substituted with one or two substituents independently selected from the group consisting of a fluorine atom, a chlorine atom, a trifluoromethyl group, a tert-butoxy group, a trifluoromethoxy group, a 2,2,2-trifluoroethoxy group, a benzyloxy group, and a phenoxy group, or a salt thereof.

[A-15] A compound according to [A-1], which is any one selected from the compound group shown below:

[Formula 17]

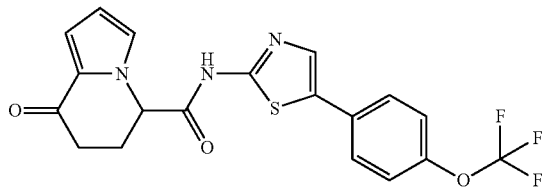

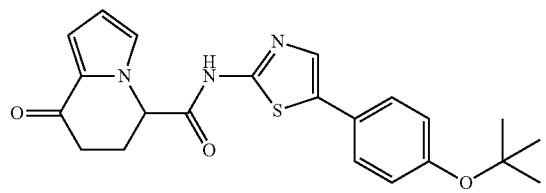

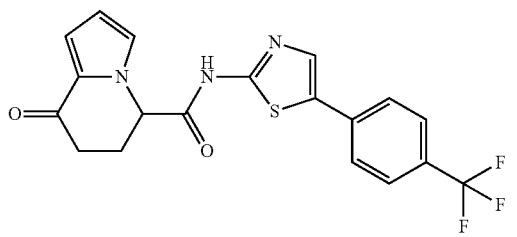

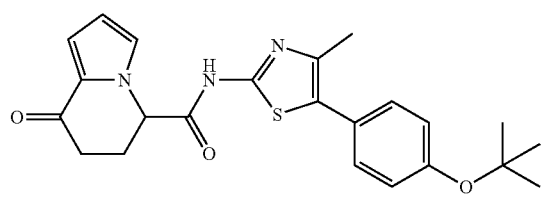

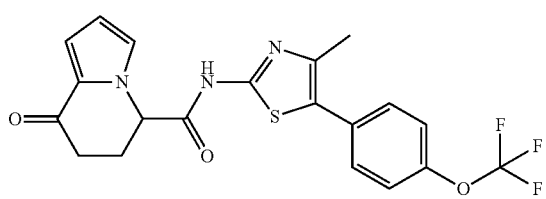

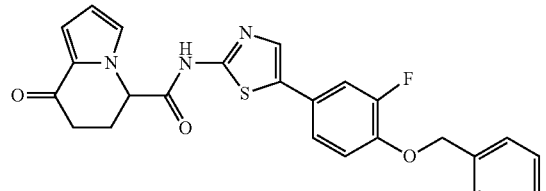

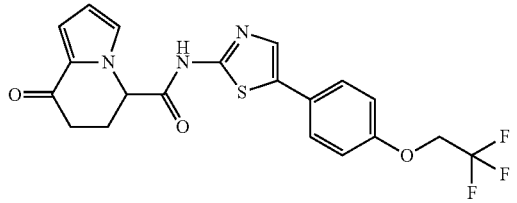

or a salt thereof.

[A-16] A compound according to [A-1], represented by the below formula:

[Formula 18]

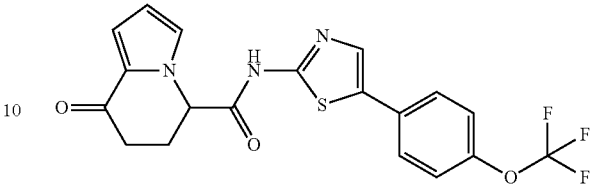

or a salt thereof.

[A-17] An optical isomer of a compound according to [A-1], represented by the below formula:

[Formula 19]

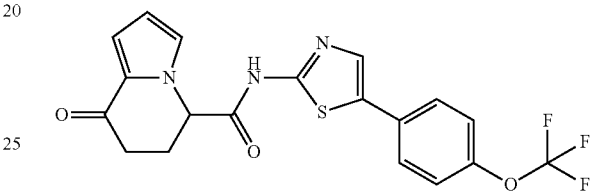

or a salt thereof. [A-18] An optical isomer of a compound according to [A-1] represented by the below formula:

[Formula 20]

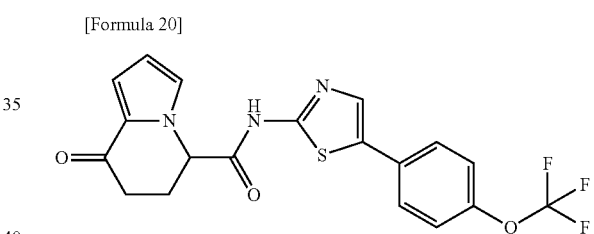

or a salt thereof, exhibiting a retention time of 14.9 minutes in measurement under analysis conditions of: column: YMC CHIRAL ART Cellulose-SB (5 μm), 250×4.6 mm I.D., column temperature: 25° C., flow rate: 0.5 ml/min, mobile phase: n-hexane/ethanol=70/30, and measurement wavelength: 293 nm.

[A-19] An optical isomer of a compound according to [A-1] represented by the below formula:

[Formula 21]

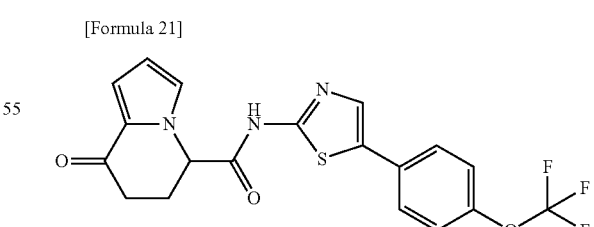

or a salt thereof, exhibiting a retention time of 21.6 minutes in measurement under analysis conditions of: column: YMC CHIRAL ART Cellulose-SB (5 μm), 250×4.6 mm I.D., column temperature: 25° C., flow rate: 0.5 ml/min, mobile phase: n-hexane/ethanol=70/30, and measurement wavelength: 293 nm.

[A-20] A compound according to [A-1] represented by the below formula:

[Formula 22]

or a salt thereof.

[A-21] A compound according to [A-1] represented by the below formula:

[Formula 23]

or a salt thereof.

[A-22] A compound according to [A-1] represented by the below formula:

[Formula 24]

or a salt thereof.

[A-23] A compound according to [A-1] represented by the below formula:

[Formula 25]

or a salt thereof.

[A-24] A compound according to [A-1] represented by the below formula:

[Formula 26]

or a salt thereof.

[A-25] An optical isomer of a compound according to [A-1], represented by the below formula:

[Formula 27]

or a salt thereof.

[A-26] A compound according to [A-1], represented by the below formula:

[Formula 28]

or a salt thereof.

[A-27] A compound according to [A-1], represented by the below formula:

[Formula 29]

or a salt thereof.

[A-28] An optical isomer of a compound according to [A-1], represented by the below formula:

[Formula 30]

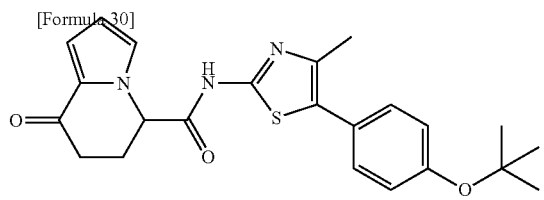

or a salt thereof, exhibiting a retention time of 13.6 minutes in measurement under analysis conditions of: column: YMC CHIRAL ART Cellulose-SC (5 μm), 250×4.6 mm I.D., column temperature: 25° C., flow rate: 0.5 ml/min, mobile phase: n-hexane/ethanol=40/60, and measurement wavelength: 288 nm.

[A-29] An optical isomer of a compound according to [A-1] represented by the below formula:

[Formula 31]

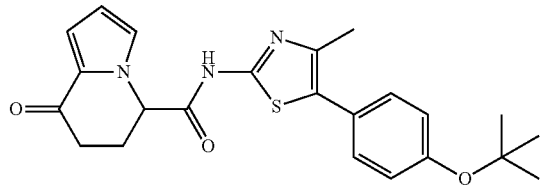

or a salt thereof, exhibiting a retention time of 23.4 minutes in measurement under analysis conditions of: column: YMC CHIRAL ART Cellulose-SC (5 μm), 250×4.6 mm I.D., column temperature: 25° C., flow rate: 0.5 ml/min, mobile phase: n-hexane/ethanol=40/60, and measurement wavelength: 288 nm.

[A-30] A compound according to [A-1] represented by the below formula:

[Formula 32]

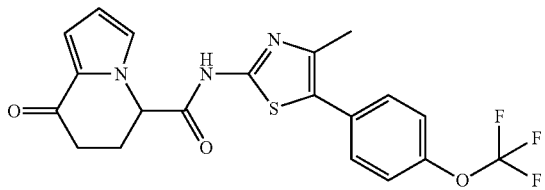

or a salt thereof.

[A-31] A compound according to [A-1] represented by the below formula:

[Formula 33]

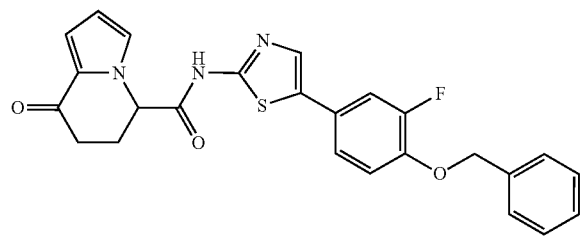

or a salt thereof.

[A-32] A compound according to [A-1] represented by the below formula:

[Formula 34]

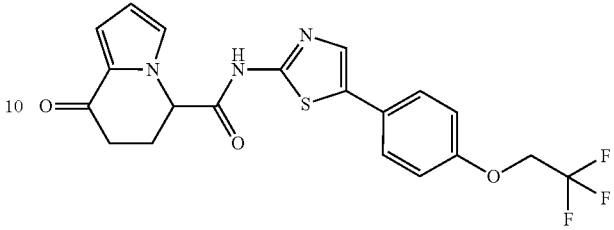

or a salt thereof.

[A-33] A compound according to any one of [A-1] to [A-32] or a salt thereof, for differentiating pluripotent stem cells into insulin-producing cells.

[A-34] A differentiation inducer of pluripotent stem cells into insulin-producing cells, comprising a compound according to any one of [A-1] to [A-32] or a salt thereof.

[A-35] Use of a compound according to any one of [A-1] to [A-32] or a salt thereof for differentiating pluripotent stem cells into insulin-producing cells.

[A-36] A method for differentiating pluripotent stem cells into insulin-producing cells, using a UCHL1 activator.

[A-37] A method according to [A-36], wherein the UCHL1 activator is a compound according to any one of [A-1] to [A-32] or a salt thereof.

[A-38] A method for differentiating pluripotent stem cells into insulin-producing cells, using a compound according to any one of [A-1] to [A-32] or a salt thereof.

[A-39] A pharmaceutical composition comprising a compound according to any one of [A-1] to [A-32] or a pharmaceutically acceptable salt thereof as an active ingredient.

[A-40] A pharmaceutical composition according to [A-39] for treating and/or preventing diabetes or a neurodegenerative disease.

[A-41] A pharmaceutical composition according to [A-40], wherein the diabetes or the neurodegenerative disease is type 1 diabetes, type 2 diabetes, Parkinson's disease, or Alzheimer's disease.

[A-42] Use of a compound according to any one of [A-1] to [A-32] or a pharmaceutically acceptable salt thereof for the manufacture of a medicament for treating and/or preventing diabetes or a neurodegenerative disease.

[A-43] Use according to [A-42], wherein the diabetes or neurodegenerative disease is type 1 diabetes, type 2 diabetes, Parkinson's disease, or Alzheimer's disease.

[A-44] A compound according to any one of [A-1] to [A-32] or a pharmaceutically acceptable salt thereof for use in a method for treating and/or preventing diabetes or a neurodegenerative disease.

[A-45] A compound or a pharmaceutically acceptable salt thereof according to [A-44], wherein the diabetes or neurodegenerative disease is type 1 diabetes, type 2 diabetes, Parkinson's disease, or Alzheimer's disease.

[A-46] A method for treating and/or preventing diabetes or a neurodegenerative disease, comprising administering a pharmacologically effective amount of a compound according to [A-1] to [A-32] or a pharmaceutically acceptable salt thereof to a warm-blooded animal.

[A-47] A method according to [A-46], wherein the diabetes or neurodegenerative disease is type 1 diabetes, type 2 diabetes, Parkinson's disease, or Alzheimer's disease.

[A-48] A method according to [A-46] or [A-47], wherein the warm-blooded animal is a human.

Advantageous Effects of Invention

A compound represented by formula (I) of the present invention or a salt thereof has a remarkable effect when differentiating pluripotent stem cells derived from mammals into insulin-producing cells, as compared with known differentiation induction methods. Accordingly, a compound of the present invention or a salt thereof can be used for the purpose of producing insulin-producing cells. Further, the insulin-producing cells thus induced to differentiate are useful for treating type 1 diabetes and type 2 diabetes. Further, a compound of the present invention or a salt thereof has an action to activate UCHL1 and therefore can be used for treating or preventing diabetes or neurodegenerative diseases of warm-blooded animals (particularly, humans).

DESCRIPTION OF EMBODIMENTS

Hereinafter, the present invention will be described in detail.

In this description, the terms described below will be used.

A "halogen atom" is a fluorine atom, a chlorine atom, a bromine atom, or an iodine atom.

A "C1-C6 alkyl group" is a linear or branched alkyl group having 1 to 6 carbon atoms. Specific examples thereof include a methyl group, an ethyl group, a propyl group, an isopropyl group, a butyl group, an isobutyl group, a sec-butyl group, a tert-butyl group, a pentyl group, an isopentyl group, a 2-methylbutyl group, a neopentyl group, a 1-ethylpropyl group, a hexyl group, an isohexyl group, a 3-methylpentyl group, a 2-methylpentyl group, a 1-methylpentyl group, a 3,3-dimethylbutyl group, a 2,2-dimethylbutyl group, a 1,1-dimethylbutyl group, or a 1,2-dimethylbutyl group.

An "aryl group" is a monocyclic or bicyclic aromatic carbocycle having 6 to 10 carbon atoms, which may be condensed with a non-aromatic heterocycle or cycloalkane. Specific examples thereof include a phenyl group, a naphthyl group, a tetralinyl group, an indanyl group, a chromanyl group, a 2,3-dihydrobenzofuranyl group, a 1,3-benzodioxolyl group, a 2,3-dihydro-1,4-benzodioxinyl group, a 1,2,3,4-tetrahydroquinolinyl group, a 1,2,3,4-tetrahydroisoquinolinyl group, an indolinyl group, or a 3,4-dihydro-2H-1,4-benzoxazinyl group. A phenyl group, a naphthyl group, or a 1,3-benzodioxolyl group is preferred.

A "C5-C10 cycloalkenyl group" is a hydrocarbon ring having one double bond within the ring having 5 to 10 carbon atoms, which may be crosslinked with an alkylene group. Specific examples thereof include a cyclopentenyl group, a cyclohexenyl group, a cycloheptenyl group, a cyclooctenyl group, a bicyclo[2.2.1]heptenyl group, or a bicyclo[2.2.2]octenyl group.

A "heterocyclyl group" is a 4- to 10-membered ring group in which the atoms constituting the ring are one to four heteroatoms independently selected from nitrogen, oxygen, and sulfur, other than carbon, which may be aromatic or non-aromatic, or may be crosslinked with an alkylene group in the case of being non-aromatic. Specific examples of a non-aromatic heterocyclyl group include an azetidinyl group, a pyrrolidinyl group, a piperidinyl group, an azepanyl group, a diazepanyl group, an azocanyl group, a piperazinyl group, a homopiperazinyl group, a morpholinyl group, an oxazepanyl group, a thiomorpholinyl group, a thiazepanyl group, a tetrahydropyranyl group, a tetrahydrofuryl group, a dioxanyl group, a dioxolanyl group, a 2-azabicyclo[2.2.1]heptyl group, a 2,5-diazabicyclo[2.2.1]heptyl group, a 3-azabicyclo[3.2.1]octyl group, an 8-azabicyclo[3.2.1]octyl group, a 9-azabicyclo[3.3.1]nonyl group, a 3,9-diazabicyclo[3.3.1]nonyl group, a dihydropyranyl group, a dihydropyrrolyl group, a dihydropyridyl group, a tetrahydropyridyl group, a tetrahydropyrazyl group, a 3,9-diazaspiro[5.5]undec-3-yl group, a 1,9-diazaspiro[5.5]undec-9-yl group, a 1,8-diazaspiro[4.5]dec-8-yl group, or a 1,4-dioxa-8-azaspiro[4.5]dec-8-yl group. Examples of an aromatic heterocyclyl group include a furyl group, a pyrrolyl group, a thienyl group, an oxazolyl group, a triazolyl group, an imidazolyl group, a pyrazolyl group, an oxadiazolyl group, a thiadiazolyl group, a triazolyl group, a tetrazolyl group, a pyridyl group, a pyrazyl group, a pyrimidyl group, a pyridazinyl group, a triazinyl group, an indolyl group, an isoindolyl group, an indazolyl group, a purinyl group, a quinolyl group, an isoquinolyl group, or a naphthyridinyl group.

A "C1-C6 alkoxy group" is a group in which a C1-C6 alkyl group is bonded to an oxygen atom. Specific examples thereof include a methoxy group, an ethoxy group, a n-propoxy group, an isopropoxy group, a n-butoxy group, a sec-butoxy group, an isobutoxy group, a tert-butoxy group, a pentyloxy group, an isopentyloxy group, a neopentyloxy group, a hexyloxy group, or an isohexyloxy group.

A "halo-C1-C6 alkyl group" is a group in which a C1-C6 alkyl group is substituted with 1 to 7 halogen atoms. Specific examples thereof include a trifluoromethyl group, a difluoromethyl group, a 1,1-difluoroethyl group, a 2,2-difluoroethyl group, or a 2,2,2-trifluoroethyl group.

A "halo-C1-C6 alkoxy group" is a group in which a C1-C6 alkoxy group is substituted with 1 to 7 halogen atoms. Specific examples thereof include a fluoromethoxy group, a difluoromethoxy group, a dichloromethoxy group, a dibromomethoxy group, a trifluoromethoxy group, a trichloromethoxy group, a 2-fluoroethoxy group, a 2-bromoethoxy group, a 2-chloroethoxy group, a 2-iodoethoxy group, a 2,2-difluoroethoxy group, a 2,2,2-trifluoroethoxy group, a 2,2,2-trichloroethoxy group, a pentafluoroethoxy group, a 3-fluoropropoxy group, a 3-chloropropoxy group, a 4-fluorobutoxy group, a 5-fluoropentyloxy group, or a 6-fluorohexyloxy group.

A "hydroxy C1-C6 alkyl group" is a group in which a C1-C6 alkyl group is substituted with one hydroxyl group. Specific examples thereof include a hydroxymethyl group, a hydroxyethyl group, a hydroxypropyl group, a hydroxybutyl group, a hydroxypentyl group, or a hydroxyhexyl group.

A "C1-C6 alkoxy C1-C6 alkoxy group" is a group in which a C1-C6 alkoxy group is substituted with a C1-C6 alkoxy group. Specific examples thereof include a methoxymethoxy group, a methoxyethoxy group, a methoxypropoxy group, an ethoxymethoxy group, an ethoxyethoxy group, an ethoxypropoxy group, or a propoxypropoxy group.

A "(C1-C6 alkyl)carbonyl group" is a group in which a C1-C6 alkyl group is bonded to a carbonyl group. Specific examples thereof include an acetyl group, a propionyl group, a butyryl group, an isobutyryl group, or a pivaloyl group.

A "(C1-C6 alkoxy)carbonyl group" is a group in which a C1-C6 alkoxy group is bonded to a carbonyl group. Specific examples thereof include a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, an isopentyloxycarbonyl group, a neopentyloxycarbonyl group, a n-hexyloxycarbonyl group, or an isohexyloxycarbonyl group.

A "(C1-C6 alkoxy)carbonyloxy group" is a group in which a C1-C6 alkoxy group is bonded to a carbonyloxy group. Specific examples thereof include a methoxycarbonyloxy group, an ethoxycarbonyloxy group, a n-propoxycarbonyloxy group, an isopropoxycarbonyloxy group, a n-butoxycarbonyloxy group, an isobutoxycarbonyloxy group, a sec-butoxycarbonyloxy group, a tert-butoxycarbonyloxy group, a n-pentyloxycarbonyloxy group, an isopentyloxycarbonyloxy group, a neopentyloxycarbonyloxy group, a n-hexyloxycarbonyloxy group, or an isohexyloxycarbonyloxy group.

A "phenyl C1-C6 alkoxy group" is a group in which a C1-C6 alkoxy group is substituted with a phenyl group at any position. Specific examples thereof include a benzyloxy group, a 1-phenylethyloxy group, a 2-phenylethyloxy group, a 1-phenylpropyloxy group, a 2-phenylpropyloxy group, or a 3-phenylpropyloxy group.

A "carbamoyl group optionally substituted with one or two C1-C6 alkyl groups" is a carbamoyl group or a group in which the one or two C1-C6 alkyl groups are bonded to a carbamoyl group. Specific examples thereof include a carbamoyl group, a methylcarbamoyl group, a dimethylcarbamoyl group, an ethylcarbamoyl group, a diethylcarbamoyl group, an ethylmethylcarbamoyl group, a propylcarbamoyl group, or a dipropylcarbamoyl group.

A "C1-C6 alkoxy group substituted by a carbamoyl group optionally substituted with one or two C1-C6 alkyl groups" is a group in which a C1-C6 alkoxy group is substituted by a carbamoyl group optionally substituted with the one or two C1-C6 alkyl groups. Specific examples thereof include a carbamoylmethyloxy group, a carbamoylethyloxy group, a methylcarbamoylmethyloxy group, a methylcarbamoylethyloxy group, a dimethylcarbamoylmethyloxy group, a dimethylcarbamoylethyloxy group, an ethylcarbamoylmethyloxy group, an ethylcarbamoylethyloxy group, a diethylcarbamoylmethyloxy group, a diethylcarbamoylethyloxy group, an ethylmethylcarbamoylmethyloxy group, an ethylmethylcarbamoylethyloxy group, a propylcarbamoylmethyloxy group, a propylcarbamoylethyloxy group, a dipropylcarbamoylmethyloxy group, or a dipropylcarbamoylethyloxy group.

A "sulfamoyl group substituted with one or two C1-C6 alkyl groups" is a group in which the one or two C1-C6 alkyl groups are bonded to a sulfamoyl group. Specific examples thereof include a methylsulfamoyl group, a dimethylsulfamoyl group, an ethylsulfamoyl group, an ethylmethylsulfamoyl group, a diethylsulfamoyl group, a propylsulfamoyl group, or a dipropylsulfamoyl group.

A "C1-C4 alkyl group" is a linear or branched alkyl group having one to four carbon atoms. Specific examples thereof include a methyl group, an ethyl group, a propyl group, an isopropyl group, a butyl group, an isobutyl group, a sec-butyl group, or a tert-butyl group.

A "C1-C4 alkoxy group" is a group in which a C1-C4 alkyl group is bonded to an oxygen atom. Specific examples thereof include a methoxy group, an ethoxy group, a n-propoxy group, an isopropoxy group, a n-butoxy group, a sec-butoxy group, an isobutoxy group, or a tert-butoxy group.

A "C1-C2 alkyl group" is a linear alkyl group having 1 or 2 carbon atoms, such as a methyl group and an ethyl group.

A "halo-C1-C2 alkyl group" is a group in which a C1-C2 alkyl group is substituted with 1 to 5 halogen atoms. Specific examples thereof include a trifluoromethyl group, a difluoromethyl group, a 1,1-difluoroethyl group, a 2,2-difluoroethyl group, or a 2,2,2-trifluoroethyl group.

A "C1-C2 alkoxy group" is a group in which a C1-C2 alkyl group is bonded to an oxygen atom, such as a methoxy group and an ethoxy group.

A "halo-C1-C2 alkoxy group" is a group in which a C1-C2 alkoxy group is substituted with 1 to 5 halogen atoms. Specific examples thereof include a fluoromethoxy group, a difluoromethoxy group, a dichloromethoxy group, a dibromomethoxy group, a trifluoromethoxy group, a trichloromethoxy group, a 2-fluoroethoxy group, a 2-bromoethoxy group, a 2-chloroethoxy group, a 2-iodoethoxy group, a 2,2-difluoroethoxy group, a 2,2,2-trifluoroethoxy group, a 2,2,2-trichloroethoxy group, or a pentafluoroethoxy group.

A "hydroxy C1-C4 alkyl group" is a group in which a C1-C4 alkyl group is substituted by one hydroxyl group. Specific examples thereof include a hydroxymethyl group, a hydroxyethyl group, a hydroxypropyl group, or a hydroxybutyl group.

A "C1-C2 alkoxy C1-C2 alkoxy group" is a group in which a C1-C2 alkoxy group is substituted by a C1-C2 alkoxy group. Specific examples thereof include a methoxymethoxy group, a methoxyethoxy group, an ethoxymethoxy group, or an ethoxyethoxy group.

A "(C1-C4 alkyl)carbonyl group" is a group in which a C1-C4 alkyl group is bonded to a carbonyl group. Specific examples thereof include an acetyl group, a propionyl group, a butyryl group, an isobutyryl group, or a pivaloyl group.

A "(C1-C4 alkoxy)carbonyl group" is a group in which a C1-C4 alkoxy group is bonded to a carbonyl group. Specific examples thereof include a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, or a tert-butoxycarbonyl group.

A "(C1-C4 alkoxy)carbonyloxy group" is a group in which a C1-C4 alkoxy group is bonded to a carbonyloxy group. Specific examples thereof include a methoxycarbonyloxy group, an ethoxycarbonyloxy group, a n-propoxycarbonyloxy group, an isopropoxycarbonyloxy group, a n-butoxycarbonyloxy group, an isobutoxycarbonyloxy group, a sec-butoxycarbonyloxy group, or a tert-butoxycarbonyloxy group.

A "phenyl C1-C4 alkoxy group" is a group in which a C1-C4 alkoxy group is substituted with a phenyl group at any position. Specific examples thereof include a benzyloxy group, a 1-phenylethyloxy group, a 2-phenylethyloxy group, a 1-phenylpropyloxy group, a 2-phenylpropyloxy group, or a 3-phenylpropyloxy group.

A "carbamoyl group optionally substituted with one or two C1-C4 alkyl groups" is a carbamoyl group or a group in which the one or two C1-C4 alkyl groups are bonded to a carbamoyl group. Specific examples thereof include a carbamoyl group, a methylcarbamoyl group, a dimethylcarbamoyl group, an ethylcarbamoyl group, a diethylcarbamoyl group, an ethylmethylcarbamoyl group, a propylcarbamoyl group, or a dipropylcarbamoyl group.

A "C1-C2 alkoxy group substituted by a carbamoyl group optionally substituted with one or two C1-C4 alkyl groups" is a group in which a C1-C2 alkoxy group is substituted by a carbamoyl group optionally substituted with the one or two C1-C4 alkyl groups. Specific examples thereof include a carbamoylmethyloxy group, a carbamoylethyloxy group, a methylcarbamoylmethyloxy group, a methylcarbamoylethyloxy group, a dimethylcarbamoylmethyloxy group, a dimethylcarbamoylethyloxy group, an ethylcarbamoylmethyloxy group, an ethylcarbamoylethyloxy group, a diethylcarbamoylmethyloxy group, a diethylcarbamoylethyloxy group, an ethylmethylcarbamoylmethyloxy group, an ethylmethylcarbamoylethyloxy group, a propylcarbamoylmethyloxy group, a propylcarbamoylethyloxy group, a dipropylcarbamoylmethyloxy group, or a dipropylcarbamoylethyloxy group.

A "sulfamoyl group substituted with one or two C1-C4 alkyl groups" is a group in which the one or two C1-C4 alkyl groups are bonded to a sulfamoyl group. Specific examples thereof include a methylsulfamoyl group, a dimethylsulfamoyl group, an ethylsulfamoyl group, an ethylmethylsulfamoyl group, a diethylsulfamoyl group, a propylsulfamoyl group, or a dipropylsulfamoyl group.

"Stem cells" are cells having self-replication ability and pluripotency, and examples thereof include ES cells, iPS cells, and adult stem cells.

"Pluripotent stem cells" are cells capable of differentiating into various cells of living organisms and are preferably ES cells or iPS cells.

"Insulin-producing cells" are cells that secrete insulin upon reaction with hyperglycemia or the like and have a superior ability to express insulin as compared with other pancreatic hormones such as glucagon or somatostatin.

Preferred aspects of the compound represented by formula (I) in the present invention will be described below.

Examples of the substituent $R^1$ in the present invention can include a hydrogen atom, a halogen atom, and a C1-C6 alkyl group. $R^1$ is preferably a hydrogen atom, a chlorine atom, a bromine atom, or a methyl group, more preferably a hydrogen atom, a chlorine atom, or a methyl group. The $R^1$ substitution can be at any position shown below in (I-i) to (I-iii).

[Formula 35]

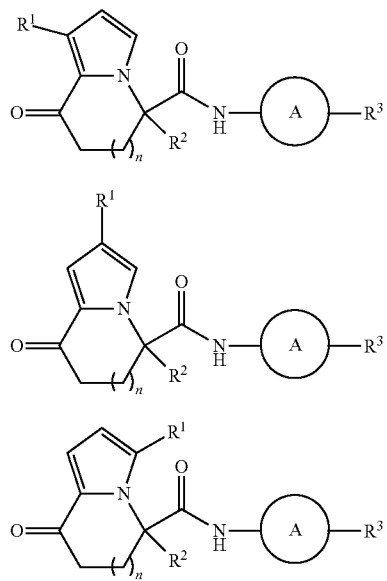

Examples of the substituent $R^2$ in the present invention can include a hydrogen atom or a C1-C6 alkyl group. $R^2$ is preferably a hydrogen atom or a C1-C2 alkyl group, more preferably a hydrogen atom or a methyl group.

Examples of the substituent $R^3$ in the present invention include an aryl group optionally substituted with one to four substituents independently selected from a substituent group α, a C5-C10 cycloalkenyl group optionally substituted with one to four substituents independently selected from the substituent group α, or a heterocyclyl group optionally substituted with one to four substituents independently selected from the substituent group α. $R^3$ is preferably a naphthyl group, a 1,3-benzodioxolyl group, a 2,2-dihalo-1,3-benzodioxolyl group, a C5-C10 cycloalkenyl group, a phenyl group optionally substituted with one or two substituents independently selected from a substituent group α1, or a 5- or 6-membered heterocyclyl group optionally substituted with one or two substituents independently selected from the substituent group α1, more preferably a naphthyl group, a 1,3-benzodioxolyl group, a 2,2-dihalo-1,3-benzodioxolyl group, a C5-C10 cycloalkenyl group, a phenyl group optionally substituted with one or two substituents independently selected from a substituent group α2, or a 5- or 6-membered heterocyclyl group optionally substituted with one or two substituents independently selected from a substituent group γ2. $R^3$ is even more preferably a naphthyl group, a 1,3-benzodioxolyl group, a 2,2-difluoro-1,3-benzodioxolyl group, a C5-C8 cycloalken-1-yl group, a phenyl group optionally substituted with one or two substituents independently selected from a substituent group α3, or a 5- or 6-membered heterocyclyl group optionally substituted with one or two substituents independently selected from a substituent group γ3, particularly preferably a 2,2-difluoro-1,3-benzodioxolyl group, a 1-tert-butoxycarbonyl-3,6-dihydro-2H-pyridin-4-yl group, or a phenyl group optionally substituted with one or two substituents independently selected from the group consisting of a fluorine atom, a chlorine atom, a trifluoromethyl group, a tert-butoxy group, a trifluoromethoxy group, a 2,2,2-trifluoroethoxy group, a benzyloxy group, and a phenoxy group. The substituent groups α to γ are as described below.

Examples of the substituent group α in the present invention include a halogen atom, a cyano group, a carboxyl group, a C1-C6 alkyl group, a C1-C6 alkoxy group, a halo-C1-C6 alkyl group, a halo-C1-C6 alkoxy group, a hydroxy C1-C6 alkyl group, a C1-C6 alkoxy C1-C6 alkoxy group, a (C1-C6 alkyl)carbonyl group, a (C1-C6 alkoxy)carbonyl group, a (C1-C6 alkoxy)carbonyloxy group, a phenyl C1-C6 alkoxy group, a non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, a phenoxy group optionally substituted with one to four substituents independently selected from a substituent group β, a phenyl group optionally substituted with one to four substituents independently selected from the substituent group β, and a benzoyl group optionally substituted with one to four substituents independently selected from the substituent group β. Preferably, the substituent group α1 is a halogen atom, a cyano group, a carboxyl group, a phenoxy group, a benzoyl group, a C1-C6 alkyl group, a C1-C6 alkoxy group, a halo-C1-C6 alkyl group, a halo-C1-C6 alkoxy group, a hydroxy C1-C6 alkyl group, a C1-C6 alkoxy C1-C6 alkoxy group, a (C1-C6 alkyl)carbonyl group, a (C1-C6 alkoxy)carbonyl group, a (C1-C6 alkoxy)carbonyloxy group, a phenyl C1-C6 alkoxy group, a 5- or 6-membered non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, or a phenyl group optionally substituted with one or two substituents independently selected from a substituent group β1. More preferably, the substituent group α2 is a halogen atom, a cyano group, a carboxyl group, a phenoxy group, a benzoyl group, a C1-C6 alkyl group, a C1-C6 alkoxy group, a halo-C1-C6 alkyl group, a halo-C1-C6 alkoxy group, a hydroxy C1-C6 alkyl group, a C1-C6 alkoxy C1-C6 alkoxy group, a (C1-C6 alkyl)carbonyl group, a (C1-C6 alkoxy)carbonyl group, a (C1-C6 alkoxy)carbonyloxy group, a phenyl C1 to C6 alkoxy group, a 5- or 6-membered non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, or a phenyl group optionally substituted with one or two substituents independently selected from a substituent group β2. Even more preferably, the substituent group α3 is a halogen atom, a cyano group, a carboxyl group, a phenoxy group, a benzoyl group, a C1-C4 alkyl group, a C1-C4 alkoxy group, a halo-C1-C2 alkyl group, a halo-C1-C2 alkoxy group, a hydroxy C1-C4 alkyl group, a C1-C2 alkoxy C1-C2 alkoxy group, a (C1-C4 alkyl)carbonyl group, a (C1-C4 alkoxy)carbonyl group, a (C1-C4 alkoxy)carbonyloxy group, a phenyl C1-C4 alkoxy group, a morpholin-1-yl group, a carbamoyl group optionally substituted with one or two C1-C4 alkyl groups, a C1-C2 alkoxy group substituted by a carbamoyl group optionally substituted with one or two C1-C4 alkyl groups, a sulfamoyl group substituted with one or two C1-C4 alkyl groups, or a phenyl group optionally substituted with one or two substituents independently selected from a substituent group β3, particularly preferably, a fluorine atom, a chlorine atom, a trifluoromethyl group, a tert-butoxy group, a trifluoromethoxy group, a 2,2,2-trifluoroethoxy group, a benzyloxy group, or a phenoxy group.

Examples of the substituent group β in the present invention include a halogen atom, a C1-C6 alkyl group, a C1-C6 alkoxy group, a halo-C1-C6 alkyl group, a halo-C1-C6 alkoxy group, and a (C1-C6 alkoxy)carbonyl group. Preferably, the substituent group β1 is a halogen atom, a C1-C6 alkyl group, a C1-C6 alkoxy group, or a (C1-C6 alkoxy)carbonyl group. More preferably, the substituent group β2 is a halogen atom, a C1-C6 alkyl group, or a C1-C6 alkoxy group. Even more preferably, the substituent group β3 is a fluorine atom, a chlorine atom, a C1-C4 alkyl group, or a C1-C4 alkoxy group, particularly preferably, a methyl group, or a methoxy group.

Examples of the substituent group γ in the present invention include the substituent group γ2 including a halogen atom, a C1-C6 alkyl group, a C1-C6 alkoxy group, a (C1-C6 alkyl)carbonyl group, and a (C1-C6 alkoxy)carbonyl group. Preferably, the substituent group γ3 is a halogen atom, a C1-C4 alkyl group, a C1-C4 alkoxy group, a (C1-C4 alkyl)carbonyl group, and a (C1-C4 alkoxy)carbonyl group, more preferably a fluorine atom, a chlorine atom, a methyl group, an isobutoxy group, or a tert-butoxycarbonyl group.

In the present invention, n can represent a numerical value of 0 or 1. When n=0, the compound of the present invention is a compound having a dihydropyrrolizinone structure represented by formula (II) below:

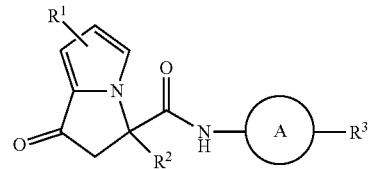

(II)

wherein $R^1$ to $R^3$ have the same meanings as described above. When n=1, the compound of the present invention is a compound having a dihydroindolizinone structure represented by formula (III) below:

[Formula 37]

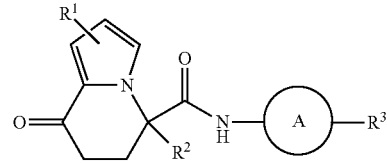

(III)

wherein $R^1$ to $R^3$ have the same meanings as described above. In the present invention, n is preferably 1, and a compound having a dihydroindolizinone structure is more preferred.

In the present invention, A represents a group represented by formulae (i) to (iv) below:

[Formula 38]

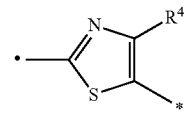

(i)

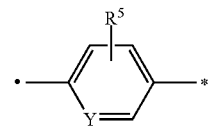

(ii)

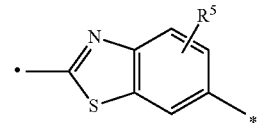

(iii)

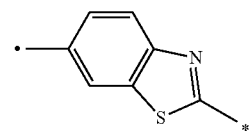

(iv)

wherein •, *, $R^4$, $R^5$, and Y have the same meanings as described above.

When A represents a group represented by formula (i), the compound of the present invention is a compound represented by formula (IV) below:

[Formula 39]

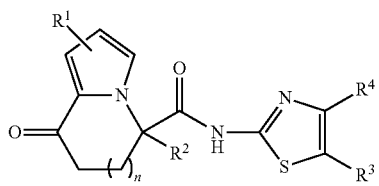
(IV)

wherein $R^1$ to $R^4$ and n have the same meanings as described above.

When A is a group represented by formula (ii), the compound of the present invention is a compound represented by formula (V) below:

[Formula 40]

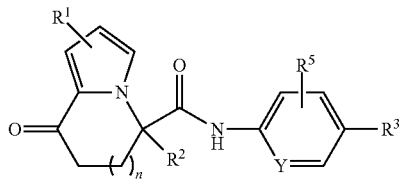
(V)

wherein $R^1$ to $R^3$, $R^5$, n, and Y have the same meanings as described above. The $R^5$ substitution can be at any position shown below in (V-i) to (V-iii).

[Formula 41]

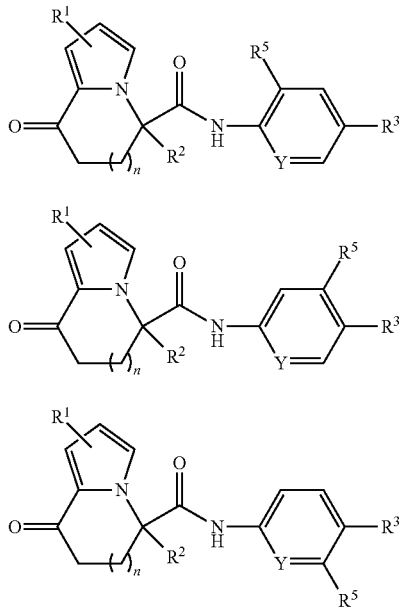
(V-i)
(V-ii)
(V-iii)

When A is a group represented by formula (iii), the compound of the present invention is a compound represented by formula (VI) below:

[Formula 42]

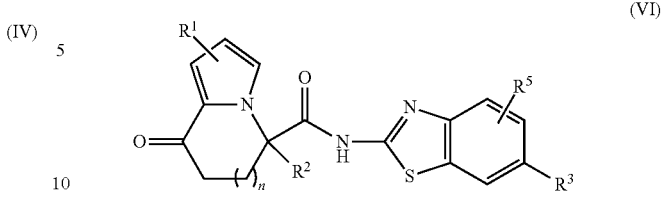
(VI)

wherein $R^1$ to $R^3$, $R^5$, and n have the same meanings as described above. The $R^5$ substitution can be at any position shown below in (VI-i) to (VI-iii).

[Formula 43]

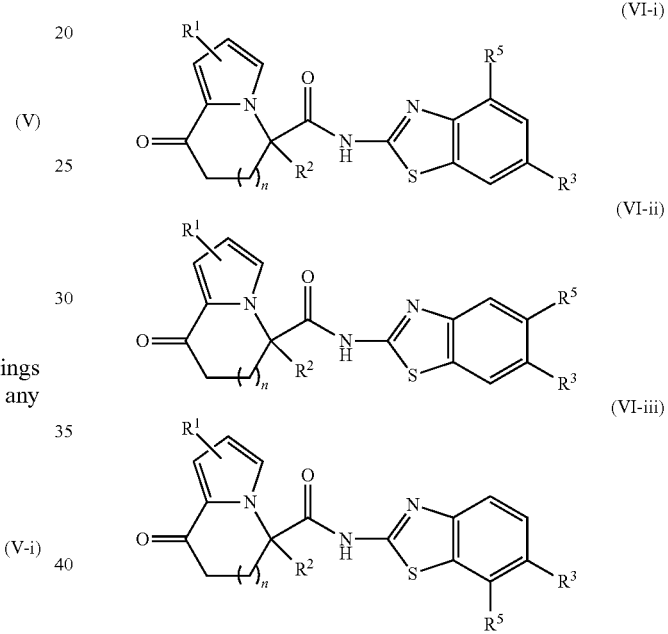
(VI-i)
(VI-ii)
(VI-iii)

When A is a group represented by formula (iv), the compound of the present invention is a compound represented by formula (VII) below:

[Formula 44]

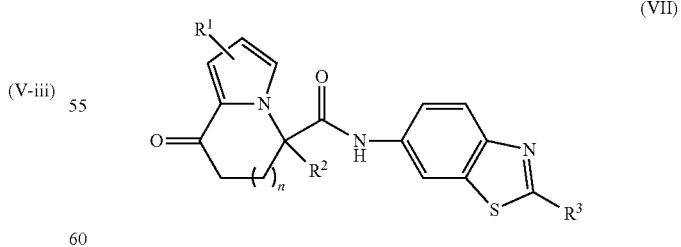
(VII)

wherein $R^1$ to $R^3$ and n have the same meanings as described above.

Examples of the substituent $R^4$ in the present invention include a hydrogen atom, a C1-C6 alkyl group, a halo-C1-C6 alkyl group, or a (C1-C6 alkoxy)carbonyl group. Preferably, $R^4$ is a hydrogen atom, a C1-C4 alkyl group, or a halo-C1-C2 alkyl group, more preferably a hydrogen atom, a methyl group, or a trifluoromethyl group.

Examples of the substituent $R^5$ in the present invention include a hydrogen atom, a halogen atom, or a C1-C6 alkyl group. Preferably, $R^5$ is a hydrogen atom, a fluorine atom, or a methyl group.

Examples of Y in the present invention include N or CH. When Y is N, (ii) in A represents a pyridine ring, and when Y is CH, (ii) in A represents a benzene ring. Y in (ii) of A is preferably CH.

The compound having formula (I) is preferably a compound described in the Examples, more preferably the following compounds:

8-oxo-N-[5-[4-(trifluoromethoxy)phenyl]thiazol-2-yl]-6,7-dihydro-5H-indolizine-5-carboxamide;

N-[5-(4-tert-butoxyphenyl)thiazol-2-yl]-8-oxo-6,7-dihydro-5H-indolizine-5-carboxamide 8-oxo-N-[5-[4-(trifluoromethyl)phenyl]thiazol-2-yl]-6,7-dihydro-5H-indolizine-5-carboxamide;

N-[5-(4-tert-butoxyphenyl)-4-methylthiazol-2-yl]-8-oxo-6,7-dihydro-5H-indolizine-5-carboxamide;

N-[4-methyl-5-[4-(trifluoromethoxy)phenyl]thiazol-2-yl]-8-oxo-6,7-dihydro-5H-indolizine-5-carboxamide;

N-[5-[4-benzyloxy-3-fluorophenyl)thiazol-2-yl]-8-oxo-6,7-dihydro-5H-indolizine-5-carboxamide; or 8-oxo-N-[5-[4-(2,2,2-trifluoroethoxy)phenyl]thiazol-2-yl]-6,7-dihydro-5H-indolizine-5-carboxamide.

The structural formulae thereof are as shown below in order.

[Formula 45]

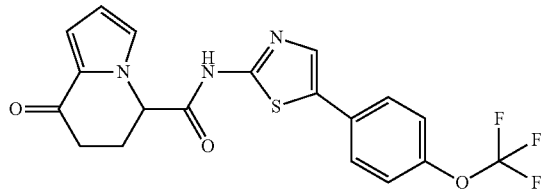
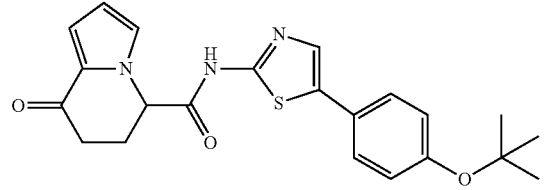
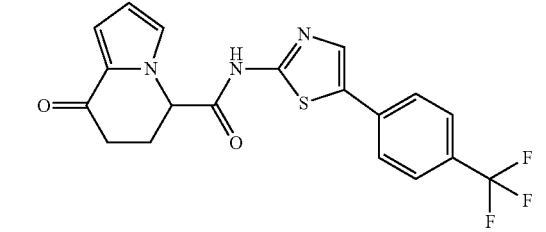
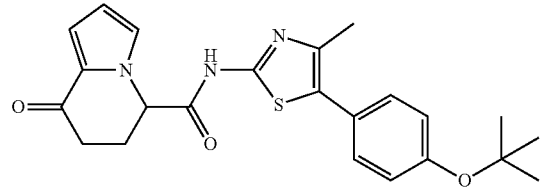
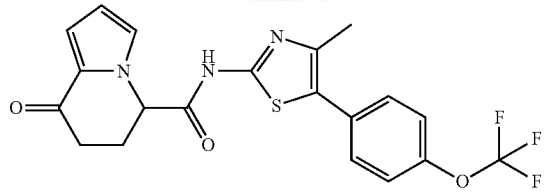
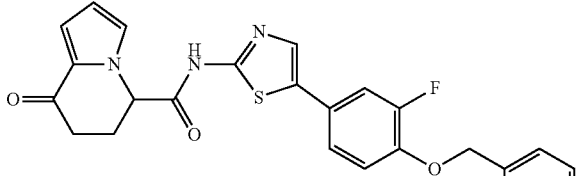
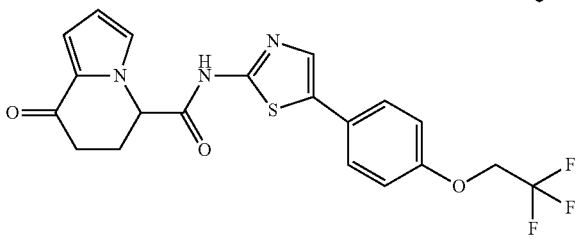

The compound having formula (I) is even more preferably an optically active form of 8-oxo-N-[5-[4-(trifluoromethoxy)phenyl]thiazol-2-yl]-6,7-dihydro-5H-indolizine-5-carboxamide or a salt thereof, and an optically active form of N-[5-(4-tert-butoxyphenyl)-4-methylthiazol-2-yl]-8-oxo-6,7-dihydro-5H-indolizine-5-carboxamide or a salt thereof.

The optically active form of 8-oxo-N-[5-[4-(trifluoromethoxy)phenyl]thiazol-2-yl]-6,7-dihydro-5H-indolizine-5-carboxamide is (5R)-8-oxo-N-[5-[4-(trifluoromethoxy)phenyl]thiazol-2-yl]-6,7-dihydro-5H-indolizine-5-carboxamide, or (5S)-8-oxo-N-[5-[4-(trifluoromethoxy)phenyl]thiazol-2-yl]-6,7-dihydro-5H-indolizine-5-carboxamide. The optically active form of N-[5-(4-tert-butoxyphenyl)-4-methylthiazol-2-yl]-8-oxo-6,7-dihydro-5H-indolizine-5-carboxamide is (5R)—N-[5-(4-tert-butoxyphenyl)-4-methylthiazol-2-yl]-8-oxo-6,7-dihydro-5H-indolizine-5-carboxamide, or (5S)-N-[5-(4-tert-butoxyphenyl)-4-methylthiazol-2-yl]-8-oxo-6,7-dihydro-5H-indolizine-5-carboxamide.

The structural formulae thereof are as shown below in order.

[Formula 46]

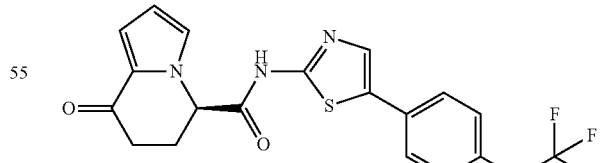
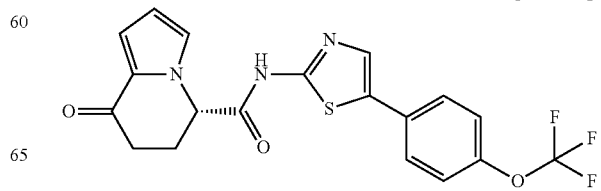

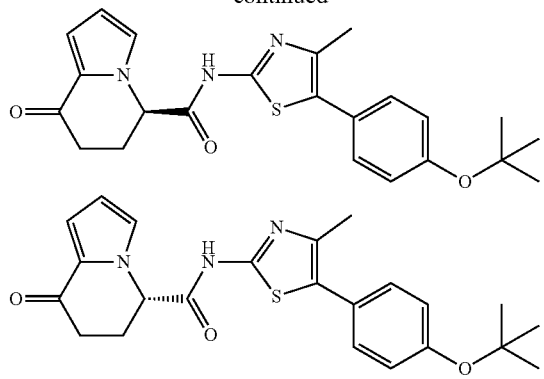

The separation and analysis of optical isomers from racemic compounds can be achieved by high-performance liquid chromatography (HPLC) using chiral columns. The identification of the optical isomers by HPLC can be performed with reference to the retention time but can be preferably performed by analyzing a mixture of a standard sample of such a racemic compound or optical isomer with an analysis sample because there may be cases where the retention time is affected by deterioration of columns, reproducibility between devices, and the like. Further, when measuring optical isomers by HPLC, there is no variation in the order in which the optical isomers are eluted under the same measurement conditions. Therefore, there may be cases where the optical isomers are characterized by a first peak in which the retention time is relatively short and a second peak in which the retention time is relatively long under specific conditions.

(Salt)

A "salt thereof" means "a salt with a base" or "an acid addition salt" of a compound that can be obtained by reaction with a base or an acid in the case where the compound has an acidic group or a basic group. In use for treating warm-blooded animals (particularly humans), the salt thereof is preferably a pharmaceutically acceptable salt. Further, a "salt thereof" and a "pharmaceutically acceptable salt" also include hydrates thereof.

A "salt with a base" of the compound is preferably an alkali metal salt such as a sodium salt, potassium salt, and lithium salt; an alkaline earth metal salt such as a magnesium salt and calcium salt; an organic base salt such as a N-methylmorpholine salt, triethylamine salt, tributylamine salt, diisopropylethylamine salt, dicyclohexylamine salt, N-methylpiperidine salt, pyridine salt, 4-pyrrolidinopyridine salt, and picoline salt; or an amino acid salt such as a glycine salt, lysine salt, arginine salt, ornithine salt, glutamate, and aspartate, more preferably, an alkali metal salt or alkaline earth metal salt.

An "acid addition salt" of the compound is preferably a hydrohalide such as a hydrofluoric acid salt, hydrochloride, hydrobromide, and hydroiodide; an inorganic acid salt such as a nitrate, perchlorate, sulfate, and phosphate; a lower alkanesulfonate such as a methanesulfonate, trifluoromethanesulfonate, and ethanesulfonate; an arylsulfonate such as a benzenesulfonate and p-toluenesulfonate; an organic acid salt such as an acetate, malate, fumarate, succinate, citrate, ascorbate, tartrate, oxalate, and maleate; and an amino acid salt such as a glycine salt, lysine salt, arginine salt, ornithine salt, glutamate, and aspartate, more preferably, a hydrohalide (particularly, a hydrochloride).

(Hydrates, etc.)

The compound of the present invention or a salt thereof may absorb moisture, adhere to the adsorbed water, or become a hydrate by standing in the atmosphere or recrystallizing. The present invention includes such various hydrates, solvates, and crystalline polymorphic compounds.

(Isomers)

There can be tautomers or geometric isomers of the compound of the present invention corresponding to the types of substituents. In this description, the compound of the present invention may be described as only one embodiment of such an isomer, but the present invention also includes other isomers than above, separated isomers, or mixtures thereof.

The compound of the present invention may have asymmetric carbon atoms or axial asymmetry, and optical isomers based on these may exist. The present invention also includes separated optical isomers and mixtures thereof.

(Isotopes)

The compound of the present invention also includes label bodies, that is, compounds in which one or more atoms of the compound are substituted with isotopes (such as $^2$H, $^3$H, $^{13}$C, $^{14}$C, and $^{35}$S).

(Prodrugs)

The present invention also includes pharmacologically acceptable prodrugs of the compound of the present invention. Such a pharmacologically acceptable prodrug is a compound having a group that can be converted into an amino group, a hydroxyl group, a carboxyl group, or the like by solvolysis or under physiological conditions. Examples of a group forming a prodrug include the group described in Prog. Med, 5, 2157-2161 (1985).

More specifically, in the case where an amino group is present in the compound, examples of a prodrug can include a compound with the amino group acylated or phosphorylated (for example, a compound with the amino group eicosanoylated, alanylated, pentylaminocarbonylated, (5-methyl-2-oxo-1,3-dioxolen-4-yl)methoxycarbonylated, tetrahydrofuranylated, pyrrolidylmethylated, or pivaloyloxymethylated).

In the case where a hydroxyl group is present in the compound, examples thereof can include a compound with the hydroxyl group acylated, alkylated, phosphorylated, or borated (for example, a compound with the hydroxyl group acetylated, palmitoylated, propanoylated, pivaloylated, succinylated, fumarylated, alanylated, or dimethylaminomethylcarbonylated).

In the case where a carboxyl group is present in the compound, examples thereof include a compound with the carboxyl group esterified or amidated (for example, a compound with the carboxyl group ethyl esterified, phenyl esterified, carboxymethyl esterified, dimethylaminomethyl esterified, pivaloyloxymethyl esterified, ethoxycarbonyloxyethyl esterified, amidated, or methylamidated).

(Production Method)

Next, typical methods for producing a compound represented by formula (I) will be described. A compound of the present invention can be produced by various production methods, and the production methods shown below are just examples. Therefore, the present invention should not be construed as being limited to these examples.

A compound represented by formula (I), a salt thereof, and a synthetic intermediate thereof can be produced by applying various known production methods using characteristics based on their basic skeletons or the types of substituents. As known methods, there are methods disclosed in "ORGANIC FUNCTIONAL GROUP PREPARATIONS", the second edition, ACADEMIC PRESS, INC., 1989 and "Comprehensive Organic Transformations", VCH Publishers Inc., 1989, for example.

Further, a compound of the present invention and a salt thereof can be synthesized according to methods A to C described below. In the synthesis of a compound of the present invention, it may be effective as a manufacturing technology to protect functional groups with suitable protecting groups (groups that can be easily converted into the functional groups) at the transient stage from raw materials into an intermediate, depending on the types of functional groups. Examples of protecting groups can include the protecting groups disclosed in P. G. M. Wuts and T. W. Greene, Protective Groups in Organic Synthesis (the third edition, 1999), and these reaction conditions may be appropriately selected for use. In general, once a synthetic route is set by a person skilled in the art, protecting groups optimal for the synthetic route are appropriately set by a person skilled in the art.

In such a method, a desired compound can be obtained by introducing the protecting groups and performing reactions, and then removing the protecting groups, as required. Further, prodrugs of the compound of the present invention can be produced by introducing specific groups at the transient stage from raw materials into an intermediate or further performing reactions using a compound obtained above, in the same manner as the aforementioned protecting groups. Each reaction can be performed by applying a general method such as esterification, amidation, and dehydration.

A compound of the present invention can be produced using an intermediate that can be synthesized by a known method or a modification thereof. In particular, an intermediate containing a group represented by formulae (ii) to (iv), which corresponds to A, can be produced using commercially available raw materials by applying a known method or a modification thereof.

The compound to be obtained in each step of methods A to C below may be a salt formed with the compound. For example, hydrochloride, sulfate, sodium salt, potassium salt, or the like can be mentioned.

The solvent to be used in the reaction in each step of methods A to C below is not specifically limited, as long as it does not inhibit the reaction and partially dissolves the starting materials, and is selected, for example, from the following solvent group. The solvent group is composed of aliphatic hydrocarbons such as hexane, pentane, petroleum ether, and cyclohexane; aromatic hydrocarbons such as benzene, toluene, and xylenes; hydrocarbon halides such as methylene chloride (chlorinated methylene), chloroform, carbon tetrachloride, dichloroethane, chlorobenzene, and dichlorobenzene; ethers such as diethyl ether, diisopropyl ether, tetrahydrofuran, dioxane, dimethoxyethane, and diethylene glycol dimethyl ether; ketones such as acetone, methyl ethyl ketone, methyl isobutyl ketone, and cyclohexanone; esters such as ethyl acetate, propyl acetate, and butyl acetate; nitriles such as acetonitrile, propionitrile, butyronitrile, and isobutyronitrile; carboxylic acids such as acetic acid and propionic acid; alcohols such as methanol, ethanol, 1-propanol, 2-propanol, 1-butanol, 2-butanol, 1-methyl-1-propanol, and 2-methyl-2-propanol; amides such as formamide, dimethylformamide, dimethylacetamide, N-methyl-2-pyrrolidone, and hexamethylphosphate triamide; sulfoxides such as dimethylsulfoxide and sulfolane; water; and mixtures thereof.

The acid to be used in the reaction in each step of methods A to C below is not specifically limited, as long as it does not inhibit the reaction, and is selected from the following acid group. The acid group is composed of inorganic acids such as hydrochloric acid, hydrobromic acid, hydriodic acid, phosphoric acid, sulfuric acid, and nitric acid; organic acids such as acetic acid, propionic acid, trifluoroacetic acid, and pentafluoropropionic acid; and organic sulfonic acids such as methanesulfonic acid, trifluoromethanesulfonic acid, p-toluenesulfonic acid, and camphorsulfonic acid.

The base to be used in the reaction in each step of methods A to C below is not specifically limited, as long as it does not inhibit the reaction, and is selected from the following base group. The base group is composed of alkali metal carbonates such as lithium carbonate, sodium carbonate, potassium carbonate, and cesium carbonate; alkali metal bicarbonates such as lithium bicarbonate, sodium bicarbonate, and potassium bicarbonate; alkali metal hydroxides such as lithium hydroxide, sodium hydroxide, and potassium hydroxide; alkaline earth metal hydroxides such as calcium hydroxide and barium hydroxide; alkali metal hydrides such as lithium hydride, sodium hydride, and potassium hydride; alkali metal amides such as lithium amide, sodium amide, and potassium amide; alkali metal alkoxides such as lithium methoxide, sodium methoxide, sodium ethoxide, sodium tert-butoxide, and potassium tert-butoxide; lithium alkylamides such as lithium diisopropylamide; silylamides such as lithium bistrimethylsilylamide and sodium bistrimethylsilylamide;

alkyl lithiums such as n-butyl lithium, sec-butyl lithium, and tert-butyl lithium; alkylmagnesium halides such as methylmagnesium chloride, methylmagnesium bromide, methylmagnesium iodide, ethylmagnesium chloride, ethylmagnesium bromide, isopropylmagnesium chloride, isopropylmagnesium bromide, and isobutylmagnesium chloride; and organic amines such as triethylamine, tributylamine, diisopropylethylamine, N-methylpiperidine, N-methylmorpholine, N-ethylmorpholine, pyridine, picoline, 4-(N,N-dimethylamino)pyridine, 4-pyrrolidinopyridine, 2,6-di(tert-butyl)-4-methylpyridine, quinoline, N,N-dimethylaniline, N,N-diethyl aniline, 1,5-diazabicyclo[4,3,0]non-5-ene (DBN), 1,4-diazabicyclo[2,2,2]octane (DABCO), and 1,8-diazabicyclo[5,4,0]undec-7-ene (DBU).

The reaction temperature in the reaction in each step of methods A to C below differs depending on the solvent, the starting materials, the reagent, and the like, and the reaction time differs depending on the solvent, the starting materials, the reagent, the reaction temperature, and the like.

In the reaction in each step of methods A to C below, the target compound of the step is isolated from the reaction mixture after the completion of the reaction according to a conventional method. The target compound is obtained, for example, by (i) leaking insoluble matter such as catalysts, as required, (ii) adding water and a solvent immiscible with water (such as methylene chloride, diethyl ether, and ethyl acetate) to the reaction mixture to extract the target compound, (iii) washing organic layers with water, followed by drying using a drying agent such as anhydrous magnesium sulfate, and (iv) distilling off the solvent. The target compound obtained can be further purified by a conventional method, such as recrystallization, reprecipitation, distillation, or column chromatography (including a normal phase and a reverse phase) using silica gel or alumina, as required. The target compound obtained can be identified by a standard analytical technique such as elemental analysis, NMR, mass spectrometry, and IR analysis, to analyze the composition and purity thereof. Alternatively, the target compound of each step can be used for the next reaction as it is without purification.

An optical isomer can be separated and purified in each step of methods A to C below by fractional recrystallization using optically active amines such as (R)- or (S)-1-phenylethylamine or separation using optically active columns.

Hereinafter, methods for producing a compound of the present invention will be described. However, the production methods are not limited to the following methods at all.

[Method A]

Method A is a method for producing a compound (A2) that can be used as a synthetic intermediate when producing the compound represented by formula (I). The compound (A2) can be produced by a known method or a modification thereof other than the synthesis methods shown in this method and Examples.

[Formula 47]

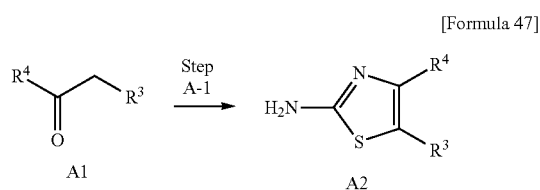

wherein $R^3$ and $R^4$ have the same meanings as described above.

(Step A-1) Formation of Thiazole Ring

Step A-1 is a step of allowing an equal amount or excess amount of a halogenating agent or bromotrimethylsilane and thiourea to act on a compound (A1) to produce the compound (A2). Examples of the halogenating agent include chlorine and bromine. The solvent in the reaction is not specifically limited, as long as the reaction proceeds, but dichloromethane, chloroform, ethanol, acetonitrile, N,N-dimethylformamide, acetic acid, or the like is used. The reaction temperature is generally 0 to 100° C., and the reaction time is generally about 0.5 hours to 2 days.

(Method B)

Method B is a method for producing a compound (B3) that can be used as a synthetic intermediate when producing the compound represented by formula (I). In the following figure, $P^1$ and $P^2$ each represent a protecting group of the amino group or a hydrogen atom. Specific examples of the protecting group include a Boc group (tert-butoxycarbonyl group), a Cbz group (benzyloxycarbonyl group), a benzylidene group, or a diphenylmethylene group. In the case where $P^1$ represents a benzylidene group or a diphenylmethylene group, $P^2$ represents the same protecting group as $P^1$. $R^3$ and A may each have a protecting group on a substituent contained therein, and each step includes a step of protecting the substituent or removing the protecting group, as required.

[Formula 48]

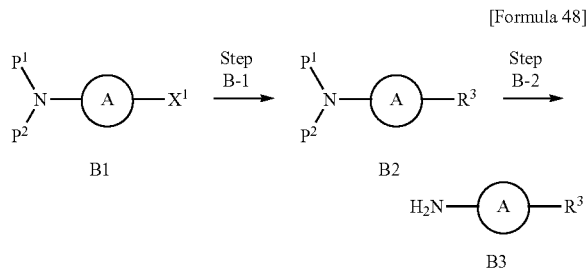

wherein $R^3$ has the same meanings as described above, $X^1$ represents a halogen atom or a leaving group such as a methanesulfonyloxy group, a trifluoromethanesulfonyloxy group, or a p-toluenesulfonyloxy group, and $P^1$ and $P^2$ each represent any protecting group.

(Step B-1) Coupling Reaction

Step B-1 is a step of introducing the substituent $R^3$ into a substituent $X^2$ on A of a compound (B1) in the presence of a palladium catalyst under conditions using an equal amount or an excess amount of boronic acid or boronic acid ester ($R^3$—B(OH)$_2$ or $R^3$—B(OR)$_2$, where R represents any alkyl group) (Suzuki-Miyaura coupling); conditions using an organic tin reagent ($R^3$—SnR$_3$) (Stille coupling); or conditions using an organic zinc reagent ($R^3$—ZnX, where X represents a halogen atom) (Negishi coupling), to obtain a compound (B2). In the aforementioned reaction, a base can be added, as required. Examples of the palladium catalyst include tetrakis (triphenylphosphine) palladium, [1,1'-bis (diphenylphosphino)ferrocene] palladium (II) dichloride dichloromethane complex (1:1), chloro(2-dicyclohexylphosphino-2'4'6'-triisopropyl-1,1'-biphenyl)[2-(2'-amino-1,1'-biphenyl)] palladium (II), tris(dibenzylideneacetone) dipalladium, palladium (II) acetate, palladium (II) acetylacetonate, or bis(triphenylphosphine) palladium (II) dichloride. Further, examples of the base include organic bases such as triethylamine, diisopropylethylamine, 1,8-diazabicyclo[5.4.0]undec-7-ene (DBU), or 1,5-diazabicyclo[4.3.0]non-5-ene (DBN), and inorganic bases such as potassium bicarbonate, sodium bicarbonate, potassium carbonate, sodium carbonate, potassium hydroxide, sodium hydroxide, potassium phosphate, or sodium phosphate. The reaction solvent is not specifically limited as long as the reaction proceeds, but examples thereof can include methanol, ethanol, tetrahydrofuran, 1,2-dimethoxyethane, 1,4-dioxane, water, N,N-dimethylformamide, dimethylsulfoxide, benzene, toluene, xylenes, or mixtures thereof. The reaction temperature is generally about 20 to 150° C. The reaction time is generally about 1 hour to 2 days. This coupling reaction can be performed according to the method described in A. Meijere and F. Diederich, "Metal-Catalyzed Cross-Coupling Reactions (the second edition, 2004)".

(Step B-2) Deprotection

Step B-2 is a step of removing the protecting groups $P^1$ and $P^2$ in the compound (B2) to produce the compound (B3). In this step, deprotection of the protecting groups in $R^3$ can be performed, as required. The reaction conditions thereof differ depending on the types of the protecting groups $P^1$ and $P^2$. The reaction can be performed, for example, according to the method described in T. W. Greene and P. G. Wuts, "Protective Groups in Organic Synthesis (the third edition, 1999)".

(Method C)

Method C is a method for producing a compound of the present invention (I) from a compound (C1) that can be synthesized using a known method or a modification thereof.

[Formula 49]

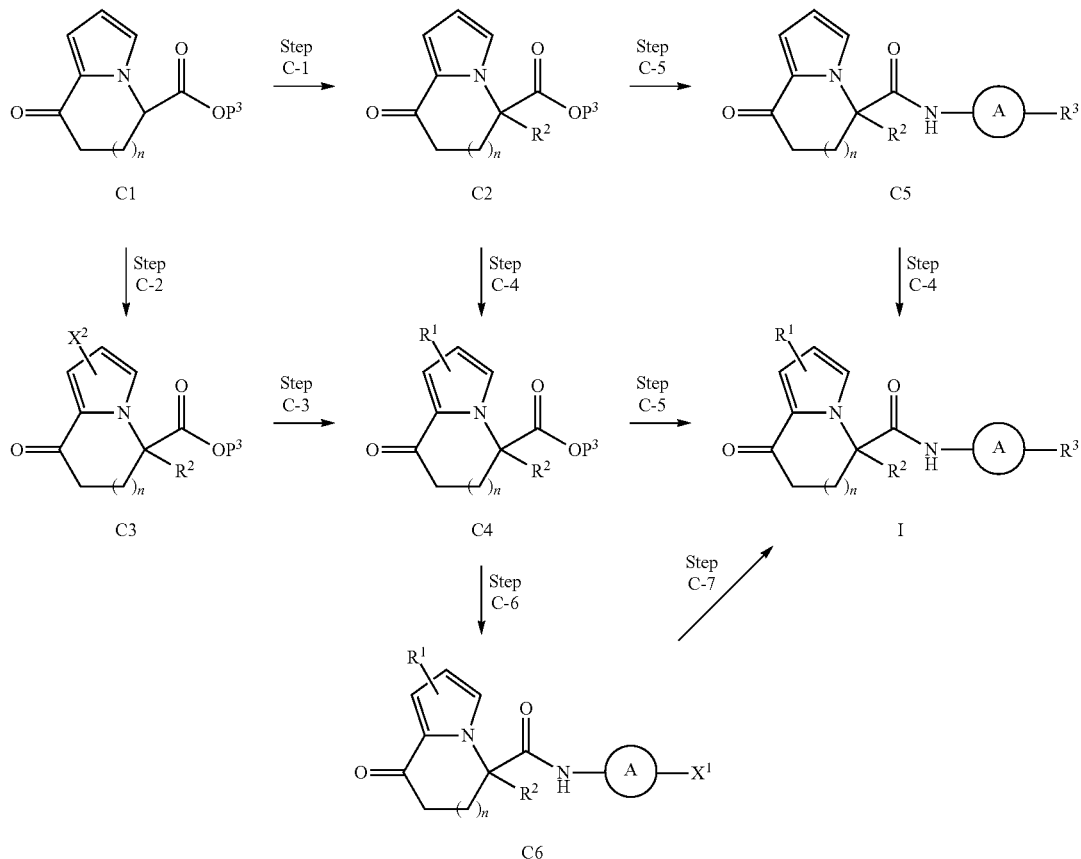

wherein R¹ to R³, n, A and X¹ have the same meanings as described above, X² represents a halogen atom, and P³ represents any protecting group.

(Step C-1) Alkylation Reaction

Step C-1 is a step of treating a compound (C1) with a base in the presence of an equal amount or an excess amount of an alkylating agent, thereby introducing the substituent $R^2$, to produce a compound (C2). As the alkylating agent, an alkyl halide, methanesulfonic acid alkyl ester, p-toluenesulfonic acid alkyl ester, or the like can be used. Examples of the base include potassium hexamethyldisilazide and sodium hexamethyldisilazide. The reaction solvent is not specifically limited, as long as the reaction proceeds, but is preferably tetrahydrofuran. The reaction temperature is generally −78 to 0° C. The reaction time is generally 0.5 to 24 hours.

(Step C-2) Halogenation and Alkylation

Step C-2 is a step of halogenating a compound (C1) with an equal amount or an excess amount of a halogenating agent, followed by alkylation, to produce a compound (C3). The order of halogenation and alkylation can be appropriately replaced. Examples of the halogenating agent include N-bromosuccinimide and N-iodosuccinimide. The reaction solvent is not specifically limited, as long as the reaction proceeds, but is preferably dichloromethane or dimethylformamide. The reaction temperature is generally about 0 to 50° C. The reaction time is generally 0.5 to 24 hours. The alkylation can be performed in the same manner as in step C-1.

(Step C-3) Coupling Reaction

Step C-3 is a step of subjecting a compound (C3) to a coupling reaction, to produce a compound (C4). Step C-3 can be performed in the same manner as in step B-1.

(Step C-4)

Step C-4 is a step of subjecting a compound (C2) or a compound (C5) to halogenation or a coupling reaction following the halogenation, to obtain a compound (C4) or a compound of the present invention (I). The halogenation can be performed in the same manner as in step C-2, and the coupling reaction can be performed in the same manner as in step B-1.

(Step C-5) Condensation Reaction

Step (C-5) is a step of removing the protecting groups of the carboxyl group in a compound (C2) or a compound (C4) to form a carboxylic acid, followed by condensation using an equal amount or an excess amount of a compound (A2) of method A or a compound (B3) of method B, to produce a compound (C5) or a compound of the present invention (I). The deprotection of the carboxyl group can be performed according to the method described in T. W. Greene and P. G. Wuts, "Protective Groups in Organic Synthesis (the third edition, 1999)". The condensation reaction is performed by allowing a suitable sulfonylating agent or a suitable condensing agent to act on the carboxylic acid obtained from the compound (C2) and the compound (C4) in the presence of a base. In the condensation reaction, an additive that promotes the reaction can be added, as required. Examples of the sulfonylating agent include 2,4,6-triisopropylbenzenesulfonyl chloride, p-toluenesulfonyl chloride, and benzenesulfonyl chloride. Examples of the condensing agent include WSC (1-ethyl-3-(3-dimethylaminopropyl)carbodiimide), DCC (1,3-dicyclohexylcarbodiimide), DMT-MM (4-(4,6-dimethoxy-1,3,5-triazin-2-yl)-4-methylmorpholinium chloride), CDI (1,1'-carbonyldiimidazole), DEPC (diethyl phosphorocyanidate), and DPPA (diphenylphosphorylazide). Examples of the base include aromatic amines such as pyridine and lutidine, and tertiary amines such as triethylamine, N,N-diisopropylethylamine, and DMAP (4-dimethylaminopyridine). Typical examples of the additive include HOAt (3H-[1,2,3]triazolo[4,5-b]pyridin-3-ol), HOBt (1H-benzotriazol-1-ol), and HOSu (N-hydroxysuccinimide). The reaction solvent is not specifically limited, as long as the reaction proceeds, but is preferably dichloromethane or N,N-dimethylformamide. The reaction temperature is generally 0 to 50° C. The reaction time is generally 0.5 to 24 hours.

(Step C-6) Condensation Reaction

Step (C-6) is a step of removing the protecting groups of the carboxyl group in the compound (C4), followed by condensation with an amine derivative, to produce a compound (C6). The same method as in step (C-5) can be used.

(Step C-7) Coupling Reaction

Step (C-7) is a step of subjecting the compound (C6) to a coupling reaction, to produce a compound of the present invention (I). The same method as in step (B-1) can be used.

The effect of a compound of the present invention or a salt thereof to promote the differentiation into insulin-producing cells can be confirmed by the method of Experimental Example 1, which will be described below.

A compound of the present invention or a salt thereof can be used as a main component of a pharmaceutical agent or reagent for promoting induction of differentiation from pluripotent stem cells into insulin-producing cells, and the present invention provides such a pharmaceutical agent or a reagent. Various stem cells can be employed as the pluripotent stem cells targeted, as long as they are stem cells capable of differentiating into endoderm cells, but the pluripotent stem cells are preferably ES cells or iPS cells, more preferably iPS cells. Various pluripotent stem cells derived from mammals can be employed but are preferably derived from humans, mice, rats, pet animals such as dogs and cats, livestock animals such as bovines, horses, pigs, and sheep, more preferably humans.

The differentiation process from pluripotent stem cells into insulin-producing cells is, for example, divided into five stages as described in Non Patent Document 4. That is, the five stages are: stage 1 in which Sox17-positive definitive endoderm cells are induced from pluripotent stem cells, stage 2 in which Foxa2-positive primitive gut tube cells are induced from the definitive endoderm cells, stage 3 in which PDX1-positive pancreatic progenitor cells are induced from the primitive gut tube cells, stage 4 in which Ngn3-positive pancreatic endocrine progenitor cells are induced from the pancreatic progenitor cells, and stage 5 in which insulin-producing cells are finally induced from the pancreatic endocrine progenitor cells. In this description, the cell differentiation may be expressed with these stages. The medium to be used for such culture is not specifically limited, as long as it is a medium generally used for cell culture, and various media can be used, such as DMEM medium and B-27 supplement.

A compound of the present invention or a salt thereof is added in the differentiation stage after the primitive gut tube cells in a differentiation process into insulin-producing cells, thereby remarkably promoting the differentiation into insulin-producing cells. The compound of the present invention is added during culture of the primitive gut tube cells, pancreatic progenitor cells, and/or pancreatic endocrine progenitor cells derived from pluripotent stem cells. In the aforementioned differentiation stages, the compound may be added at any one stage or two stages out of stages 3 to 5, or at all the three stages, but is preferably added at all the stages from stage 3 to stage 5.

In stage 3, a medium containing retinoic acid, KAAD-cyclopamine, a TGFβ receptor kinase inhibitor (such as SB431542), or a BMP signal inhibitor (such as Noggin) is generally used, but a compound of the present invention or a salt thereof may be added instead of these or may be added in addition to these.

In stage 4, a medium containing a protein kinase C activator (such as indolactam V), a TGFβ receptor kinase inhibitor (such as ALk5 inhibitor II), or Noggin is generally used for culture, but a compound of the present invention or a salt thereof may be added instead of these or may be added in addition to these.

In stage 5, a medium containing GLP-1 receptor agonist or nicotinamide is generally used for culture, a compound of the present invention or a salt thereof may be added instead of these or may be added in addition to these.

A compound of the present invention or a salt thereof can be added to the medium in solid form as it is, in powder form, or after being dissolved in an organic solvent such as dimethylsulfoxide. The amount to be added is not specifically limited but is set by a person skilled in the art, so that the differentiation from pluripotent stem cells into insulin-producing cells proceeds efficiently. In several embodiments of the present invention, a compound of the present invention is added so as to be present in the medium in an amount of 1 ng/mL to 5 mg/mL, preferably 10 ng/mL to 5 mg/mL, more preferably 50 ng/mL to 5 mg/mL, even more preferably 100 ng/mL to 1 mg/mL.

A compound of the present invention or a salt thereof has been confirmed to bind to UCHL1 and has an effect to improve its enzyme activity. It has been reported that UCHL1 exhibits high expression level in pancreatic β cells and is deficient in pancreatic β cells of type 2 diabetics, and a reduction in expression level or activity thereof induces apoptosis in pancreatic β cells. Thus, UCHL1 is considered to be a very important enzyme in the survival and functions of pancreatic β cells. The fact that a compound of the present invention having an action to activate UCHL1 has promoted induction of differentiation into insulin-producing cells is considered to suggest that activation of UCHL1 in the cells has induced, promoted, and/or supported the phenotype of differentiated cells as insulin-producing cells. That is, the present invention also provides a method for promoting induction of differentiation from pluripotent stem cells into insulin-producing cells by enhancing functions of UCHL1 in cells during the differentiation in the induction of differentiation. As a method for enhancing the functions of UCHL1 in the cells, there is no limitation to addition of a compound of the present invention, and a method of increasing the expression level of UCHL1 proteins by introducing UCHL1 gene or editing the gene, a method of adding UCHL1 proteins to a culture solution, a method of enhancing the expression of UCHL1 proteins in the cells by adding a substance that activates an upstream signal of UCHL1 gene, or the like can be employed.

A compound of the present invention or a salt thereof has an action to activate UCHL1 and can be used for treating and/or preventing diseases the pathological conditions of which can be expected to be improved by the activation of UCHL1. Examples of such diseases can include diabetes such as type 1 diabetes or type 2 diabetes, and neurodegenerative diseases such as Alzheimer's disease or Parkinson's disease. The action of a compound of the present invention or a salt thereof to activate UCHL1 can be confirmed by Experimental Example 2, which will be described below.

A compound of the present invention or a salt thereof has an action to improve the pathological conditions of diabetes and can be used for treating and preventing diabetes. Such an action to improve the pathological conditions of diabetes can be confirmed by Experimental Example 3, which will be described below.

(Administration Form)

A compound of the present invention or a salt thereof is administered in various forms. The administration may be in any form of oral administration such as tablets, pills, capsules, granules, powders, or liquid formulations, or parenteral administration such as intra-articular, intravenous, or intramuscular injections, suppositories, eye drops, eye ointments, transdermal solutions, ointments, transdermal patches, transmucosal solutions, transmucosal patches, or inhalants.

As a solid composition for oral administration, tablets, powders, granules, or the like are used. In such a solid composition, one or more active ingredients are mixed with at least one inert excipient, such as lactose, mannitol, glucose, hydroxypropyl cellulose, microcrystalline cellulose, starch, polyvinylpyrrolidone, and/or magnesium aluminometasilicate. The composition may contain inert additives, for example, lubricants such as magnesium stearate, disintegrants such as sodium carboxymethyl starch, stabilizers, and solubilizers, according to a conventional method. The tablets or pills may be coated with sugar or a film of gastric or enteric substance, as required.

Liquid compositions for oral administration include pharmaceutically acceptable emulsifiers, solutions, suspending agents, syrups, or elixirs and include inert diluents that are commonly used, such as purified water or ethanol. The liquid compositions may contain additives such as solubilizers, humectants, and suspending agents, sweeteners, flavoring agents, aromatics, or preservatives other than the inert diluents.

Injections for parenteral administration contain sterile aqueous or non-aqueous solutions, suspending agents, or emulsifiers. Examples of the aqueous solvents include distilled water for injections or physiological saline. Examples of the non-aqueous solvents include propylene glycol, polyethylene glycol, vegetable oils such as olive oil, alcohols such as ethanol, or polysorbate 80. Such compositions may further contain tonicity agents, preservatives, humectants, emulsifiers, dispersants, stabilizers, or solubilizers. These are sterilized, for example, by filtration through a bacteria-retaining filter, compounding of a bactericide, or irradiation. Further, these can be used also by producing a sterile solid composition and dissolving or suspending it in sterile water or a sterile solvent for injections before use.

Examples of external medicines include ointments, plasters, creams, jellies, cataplasms, sprays, lotions, eye drops, and eye ointments. They contain ointment bases, lotion bases, aqueous or non-aqueous liquid formulations, suspending agents, emulsions, or the like that are commonly used. Examples of ointments or lotion bases include polyethylene glycol, propylene glycol, white vaseline, white beeswax, polyoxyethylene hardened castor oil, glycerin monostearate, stearyl alcohol, cetyl alcohol, lauromacrogol, and sorbitan sesquioleate.

Inhalants and transmucosal agents such as nasal preparations are used in solid, liquid, or semi-solid form and can be produced according to a conventionally known method. For example, known excipients and further pH adjusters, preservatives, surfactants, lubricants, stabilizers, thickeners, or the like may be appropriately added. A device suitable for inhalation or insufflation can be used for administration. For example, using a known device such as a metered dose inhalation device or nebulizer, the compound can be administered alone, or a powder mixture prescribed, or in combination with a pharmaceutically acceptable carrier as a solution or a suspension. Dry powder inhalers and the like may be used for single or multiple dose administration, and dry powder or powder-containing capsules may be used. Alternatively, forms of suitable propellants such as pressurized aerosol sprays using a suitable gas such as chlorofluoroalkane, hydrofluoroalkane, or carbon dioxide may be employed.

(Dosage)

Generally, in the case of oral administration, the dosage per day is suitably about 0.001 to 100 mg/kg, preferably 0.1 to 30 mg/kg, more preferably 0.1 to 10 mg/kg per body weight. Then, this dosage is administered once or separately twice or more. In the case of intravenous administration, the dosage per day is suitably about 0.0001 to 10 mg/kg per body weight. Then, this dosage is administered once or separately multiple times per day. Further, in the case of transmucosal agents, about 0.001 to 100 mg/kg per body weight is administered once or separately multiple times per day. The dosage is appropriately determined in consideration of the symptom, age, gender, and the like corresponding to individual cases.

(Combined Use)

A compound of the present invention or a salt thereof can be used in combination with various therapeutic agents or prophylactic agents for diseases on which the compound is considered to be effective. In such combined use, the administration may be carried out simultaneously or sequentially or intermittently at desired time intervals. Formulations for simultaneous administration may be a combination formulation or may be separate formulations.

(Formulation Example 1) Powder 5 g of a compound of the present invention, 895 g of lactose, and 100 g of corn starch are mixed together with a blender, to obtain a powder.

(Formulation Example 2) Granules 5 g of a compound of the present invention, 865 g of lactose, and 100 g of low-substituted hydroxypropyl cellulose are mixed together. Thereafter, 300 g of a 10% hydroxypropyl cellulose aqueous solution is added thereto, and the mixture is kneaded. The mixture is granulated using an extrusion granulator, followed by drying, to obtain granules.

(Formulation Example 3) Tablets 5 g of a compound of the present invention, 90 g of lactose, 34 g of corn starch, 20 g of crystalline cellulose, and 1 g of magnesium stearate are mixed together with a blender. Thereafter, the mixture is tableted with a tableting machine, to obtain tablets.

Hereinafter, the present invention will be described further in detail by way of Reference Examples, Examples, and Experimental Examples, but the scope of the present invention is not limited to these examples.

In the Reference Examples and Examples, elution in column chromatography was performed under observation by TLC (Thin Layer Chromatography). In the TLC observation, silica gel 60F254 available from Merck KGaA was employed as a TLC plate, a solvent used as an elution solvent in column chromatography was employed as a developing solvent, and a UV detector was employed as a detection method. As a silica gel for the column, silica gel SK-85 also available from Merck KGaA (230 to 400 mesh) or Chromatorex NH available from FUJI SILYSIA CHEMICAL LTD. (200-350 mesh) was used. Other than normal column chromatography devices, an automatic chromatography device available from Shoko Science Co., Ltd. (Purif-α2 or Purif-espoir2) was appropriately used. An elution solvent was determined based on the TLC observation.

The abbreviations used in the Reference Examples, Examples, and Experimental Examples below have the following meanings:

mg: milligram, g: gram, μL: microliter, mL: milliliter, mmol: millimole, mM: millimolar concentration, μM: micromolar concentration, μm: micrometer, mm: millimeter, and MHz: megahertz.

In the nuclear magnetic resonance (which will be hereinafter referred to as $^1$H NMR) spectrum in the Reference Examples and Examples below, chemical shift values were described in terms of δ values (ppm) using tetramethylsilane as a standard substance. The splitting pattern is indicated by s for singlet, d for doublet, t for triplet, q for quadruplet, m for multiplet, and br for broad. Mass spectrometry (which will be hereinafter referred to as MS) was performed by EI (Electron Ionization), ESI (Electrospray Ionization), or FAB (Fast Atom Bombardment).

EXAMPLES

Reference Example 1

N-(5-Bromothiazol-2-yl)-8-oxo-6,7-dihydro-5H-indolizine-5-carboxamide

To a solution of commercially available 8-oxo-6,7-dihydro-5H-indolizine-5-carboxylic acid (1.51 g, 8.43 mmol), commercially available 5-bromothiazol-2-amine (2.64 g, 10.2 mmol) and 3-hydroxytriazolo[4,5-b]pyridine (1.23 g, 9.04 mmol) in dichloromethane (30 mL) were added 1-ethyl-3-(3-dimethylaminopropyl)carbodiimide hydrochloride (2.43 g, 12.6 mmol) and N,N-diisopropylethylamine (2.94 mL, 16.9 mmol), followed by stirring at room temperature for 2 hours. The reaction solution was washed with 1N hydrochloric acid and a saturated aqueous solution of sodium chloride, dried over anhydrous sodium sulfate, and then filtered to distil off the solvent under reduced pressure. The residue was purified by silica-gel column chromatography (n-hexane/10% methanol-ethyl acetate solution=3/1-0/1) to obtain 1.88 g (yield: 66%) of the title compound as a solid.

Reference Example 2

N-(4-Bromophenyl)-8-oxo-6,7-dihydro-5H-indolizine-5-carboxamide

Using commercially available 4-bromoaniline, 4.66 g (yield: 84%) of the title compound was obtained as a solid according to the method of Reference Example 1.

Reference Example 3

N-(4-Bromo-2-fluorophenyl)-8-oxo-6,7-dihydro-5H-indolizine-5-carboxamide

Using commercially available 4-bromo-2-fluoroaniline, 345 mg (yield: 58%) of the title compound was obtained as a solid according to the method of Reference Example 1.

Reference Example 4

N-(5-Bromo-4-methylthiazol-2-yl)-8-oxo-6,7-dihydro-5H-indolizine-5-carboxamide

Using commercially available 5-bromo-4-methyl-thiazol-2-amine, 252 mg (yield: 25%) of the title compound was obtained as a solid according to the method of Reference Example 1.

Reference Example 5

N-(6-Bromo-1,3-benzothiazol-2-yl)-8-oxo-6,7-dihydro-5H-indolizine-5-carboxamide

Using commercially available 2-amino-6-bromobenzothiazole, 585 mg (yield: 42%) of the title compound was obtained as a solid according to the method of Reference Example 1.

Reference Example 6

N-(4-Bromo-2-methylphenyl)-8-oxo-6,7-dihydro-5H-indolizine-5-carboxamide

Using commercially available 4-bromo-2-methyl-aniline, 515 mg (yield: 66%) of the title compound was obtained as a solid according to the method of Reference Example 1.

Reference Example 7

N-(5-Bromo-2-pyridyl)-8-oxo-6,7-dihydro-5H-indolizine-5-carboxamide

Using commercially available 5-bromopyridin-2-amine, 455 mg (yield: 58%) of the title compound was obtained as a solid according to the method of Reference Example 1.

Reference Example 8

N-(2-Chloro-1,3-benzothiazol-6-yl)-8-oxo-6,7-dihydro-5H-indolizine-5-carboxamide Using commercially available 2-chloro-1,3-benzothiazol-6-amine, 637 mg (yield: 76%) of the title compound was obtained as a solid according to the method of Reference Example 1.

Reference Example 9

5-[4-(Trifluoromethoxy)phenyl]thiazol-2-amine

To a mixture of N-(5-bromothiazol-2-yl)-1,1-diphenyl-methanimine disclosed in International Publication No. WO 2003014095 (1.46 g, 4.25 mmol), commercially available 4-(trifluoromethoxy)phenylboronic acid (4.30 g, 20.0 mmol), potassium carbonate (2.97 g, 21.5 mmol), water (3 mL) and 1,4-dioxane (15 mL) was added a [1,1'-bis(diphenylphosphino)ferrocene]palladium(II) dichloride-dichloromethane complex (1:1) (338 mg, 0.414 mmol), followed by stirring at 100° C. under a nitrogen atmosphere for 4 hours. After water was added to the reaction mixture, it was extracted with ethyl acetate. The organic layers were combined, washed with water and saturated saline, and then dried over anhydrous sodium sulfate. The solvent was distilled off under reduced pressure, and the residue obtained was purified by silica-gel column chromatography (n-hexane/ethyl acetate=9/1-3/1). To a solution of an oil material obtained in methanol (20 mL) was added 1N hydrochloric acid (5 mL, 5.0 mmol), followed by stirring at room temperature for 5.5 hours. The reaction mixture was concentrated under reduced pressure, and the precipitated solid was washed with dichloromethane to obtain 897 mg (yield: 81%) of the title compound as a solid.

Reference Example 10 tert-Butyl N-[5-[4-(dimethylcarbamoyl)phenyl]thiazol-2-yl]carbamate

To a solution of commercially available tert-butyl N-(5-bromothiazol-2-yl) carbamate (500 mg, 1.89 mmol) in 1,4-dioxane (30 mL) were added [4-(dimethylcarbamoyl)phenyl]boronic acid (519 mg, 2.69 mmol) and a [1,1'-bis(diphenylphosphino)ferrocene]palladium(II) dichloride-dichloromethane complex (1:1) (74 mg, 0.09 mmol) at room temperature, followed by stirring. To the reaction mixture were added potassium carbonate (743 mg, 5.38 mmol) and water (3.0 mL), followed by stirring at 100° C. in an argon atmosphere for 4.5 hours. After water was added to the reaction mixture, it was extracted with ethyl acetate. The organic layers were combined, washed with water and saturated saline, and then dried over anhydrous sodium sulfate. The solvent was distilled off under reduced pressure, and the residue obtained was purified by silica-gel column chromatography (dichloromethane/methanol=100/0-93/7, 90/10-70/30) to obtain 172 mg (yield: 28%) of the title compound as a solid.

Reference Example 11

4-(2-Aminothiazol-5-yl)-N,N-dimethylbenzamide

To a solution of the tert-butyl N-[5-[4-(dimethylcarbamoyl)phenyl]thiazol-2-yl]carbamate obtained in Reference Example 10 (172 mg, 0.495 mmol) in dichloromethane (10 mL) was added trifluoroacetic acid (2.0 mL, 26 mmol) at room temperature, followed by stirring and thereafter standing. After the reaction solution was concentrated under reduced pressure, and a saturated aqueous solution of sodium bicarbonate was added thereto, the mixture was extracted with dichloromethane. After the organic layers were dried over anhydrous sodium sulfate, the solvent was distilled off under reduced pressure to obtain 118 mg (yield: 96%) of the title compound as a solid.

Reference Example 12

5-(1,3-Benzodioxol-5-yl)thiazol-2-amine

Using commercially available 1,3-benzodioxol-5-ylboronic acid, a product was obtained according to the method of Reference Example 10. Thereafter, 123 mg (31%, 2 steps) of the title compound was obtained as a solid according to the method of Reference Example 11.

Reference Example 13

4-(2-Aminothiazol-5-yl)benzonitrile

A solution of bromine (56 μL, 1.09 mmol) in dichloromethane (0.56 mL) was added to a solution of commercially available 4-(2-oxoethyl)benzonitrile (142 mg, 0978 mmol) in dichloromethane (10 mL) under ice cooling. After the reaction solution was warmed to room temperature, the mixture was stirred for 3 hours. After neutralization by adding a saturated aqueous solution of sodium bicarbonate to the reaction solution under ice cooling, the mixture was extracted with dichloromethane. After the organic layers were combined and dried over anhydrous sodium sulfate, the solvent was distilled off under reduced pressure. To a solution of the residue obtained in ethanol (30 mL) was added thiourea (150 mg, 1.97 mmol), followed by stirring under heating reflux for 4.5 hours. After cooling, the solvent was distilled off under reduced pressure, and the residue obtained was purified by silica-gel column chromatography (dichloromethane/methanol=99/1-95/5) to obtain 8.3 mg (4.2%) of the title compound as a solid.

Reference Example 14 tert-Butyl 2-[4-[2-(tert-butoxycarbonylamino)thiazol-5-yl]phenoxy]acetate

Using commercially available tert-butyl 2-[4-(4,4,5,5-tetramethyl-1,3,2-dioxaborolan-2-yl) phenoxy]acetate (2.4 g, 7.2 mmol), 248 mg (11%) of the title compound was obtained as a solid according to the method of Reference Example 10.

Reference Example 15

Methyl 2-[4-(2-aminothiazol-5-yl)phenoxy]acetate

Using the tert-butyl 2-[4-[2-(tert-butoxycarbonylamino) thiazol-5-yl]phenoxy]acetate (193 mg, 0.475 mmol) obtained in Reference Example 14, a solid was obtained according to the method of Reference Example 11. To a mixed solution of the solid obtained in tetrahydrofuran (10 mL) and methanol (3 mL) was added trimethylsilyldiazomethane (0.6M hexane solution, 1.0 mL) at room temperature, followed by stirring for 6 hours. After the reaction solution was concentrated under reduced pressure and a saturated aqueous solution of sodium bicarbonate was added thereto, the mixture was extracted with dichloromethane. After the organic layers were dried over anhydrous sodium sulfate, the solvent was distilled off under reduced pressure, and the residue obtained was purified by silica-gel column chromatography (dichloromethane/methanol=99/1-97/3) to obtain 92.5 mg (yield: 74%) of the title compound as a solid.

Reference Example 16

Methyl 2-[4-[2-[(8-oxo-6,7-dihydro-5H-indolizine-5-carbonyl)amino]thiazol-5-yl]phenoxy]acetate Using the methyl 2-[4-(2-aminothiazol-5-yl)phenoxy]acetate obtained in Reference Example 15, 85.7 mg (yield:

89%) of the title compound was obtained as a solid according to the method of Example 1.

Reference Example 17

Methyl 2-bromo-8-oxo-6,7-dihydro-5H-indolizine-5-carboxylate

To a solution of commercially available methyl 8-oxo-6,7-dihydro-5H-indolizine-5-carboxylate (261 mg, 1.35 mmol) in dichloromethane (5 mL) was added N-bromosuccinimide (228 mg, 1.28 mmol) at room temperature, followed by stirring for 4 hours. The solvent was distilled off under reduced pressure, and the residue obtained was purified by silica-gel column chromatography (n-hexane/ethyl acetate=4/1-2/1) to obtain 56.9 mg (yield: 16%) of the title compound as a solid.

Reference Example 18

2-Bromo-8-oxo-N-[5-[4-(trifluoromethoxy)phenyl]thiazol-2-yl]-6,7-dihydro-5H-indolizine-5-carboxamide To a solution of the methyl 2-bromo-8-oxo-6,7-dihydro-5H-indolizine-5-carboxylate obtained in Reference Example 17 (56.9 mg, 0.209 mmol) in ethanol (2 mL) was added a 1N sodium hydroxide aqueous solution (0.5 mL, 0.50 mmol), followed by stirring at 60° C. for 2 hours. After acidification with 1N hydrochloric acid, the mixture was extracted with ethyl acetate. After the organic layers were dried over anhydrous sodium sulfate, the solvent was distilled off under reduced pressure, to obtain a yellow solid (52.5 mg). Using the solid obtained (52.5 mmol) and the 5-[4-(trifluoromethoxy)phenyl]thiazol-2-amine obtained in Reference Example 9, 48.0 mg (yield: 55%) of the title compound was obtained as a solid according to the method of Example 9.

Reference Example 19

N-(5-Bromothiazol-2-yl)-2-methyl-8-oxo-6,7-dihydro-5H-indolizine-5-carboxamide

To a mixture of the methyl 2-bromo-8-oxo-6,7-dihydro-5H-indolizine-5-carboxylate (65.2 mg, 0.24 mmol) obtained in Reference Example 17, commercially available 2,4,6-trimethyl-1,3,5,2,4,6-trioxatriborinane (0,201 mL, 1.44 mmol) and potassium carbonate (171 mg, 1.24 mmol) were added 1,4-dioxane (1.5 mL) and water (0.5 mL). Thereafter, [1,1'-bis(di-tert-butylphosphino)ferrocene]palladium(II) dichloride (15.6 mg, 0.024 mmol) was further added thereto, followed by stirring at 100° C. under a nitrogen atmosphere for 2.5 hours. After water and 1N hydrochloric acid were added to the reaction solution, it was extracted with ethyl acetate. After the organic layers were washed with saturated saline and dried over anhydrous sodium sulfate, the solvent was distilled off under reduced pressure. Using the residue obtained, 23.9 mg (yield: 22%) of the title compound was obtained as a solid according to the method of Reference Example 1.

Reference Example 20

Methyl 2-chloro-8-oxo-6,7-dihydro-5H-indolizine-5-carboxylate

Using commercially available N-chlorosuccinimide, 56.3 mg (yield: 5.2%) of the title compound was obtained as a solid according to the method of Reference Example 17.

Reference Example 21

Methyl 5-methyl-8-oxo-6,7-dihydroindolizine-5-carboxylate

To a solution of commercially available methyl 8-oxo-6,7-dihydro-5H-indolizine-5-carboxylate (987 mg, 4.89 mmol) and methyl iodide (1.27 mL, 20.4 mmol) in tetrahydrofuran was added a 1.0M potassium bis(trimethylsilyl)amide tetrahydrofuran solution (11.2 mL, 11.2 mmol) dropwise over 30 minutes or more at −78° C. After the mixture was stirred at the same temperature for 1 hour, a saturated aqueous solution of ammonium chloride was added thereto, followed by quenching. After water was added to the reaction solution, it was extracted with ethyl acetate. The organic layers were washed with saturated saline and dried over anhydrous sodium sulfate. The solvent was distilled off under reduced pressure, and the residue obtained was purified by silica-gel column chromatography (n-hexane/ethyl acetate=6/1-1/1) to obtain 592 mg (yield: 56%) of the title compound as an oil material.

Reference Example 22

5-Methyl-8-oxo-6,7-dihydroindolizine-5-carboxylic acid

To a solution of the methyl 5-methyl-8-oxo-6,7-dihydroindolizine-5-carboxylate obtained in Reference Example 21 (63.0 mg, 0.304 mmol) in ethanol (1.0 mL) was added a 1N sodium hydroxide aqueous solution (0.91 mL, 0.91 mmol), followed by stirring at 80° C. for 2 hours. After neutralization by adding 1N hydrochloric acid to the reaction solution, it was extracted with ethyl acetate. The organic layers were washed with saturated saline and dried over anhydrous sodium sulfate. The solvent was distilled off under reduced pressure to obtain 48.3 mg (yield: 82%) of the title compound as a solid.

Reference Example 23

N-(5-Bromothiazol-2-yl)-5-methyl-8-oxo-6,7-dihydroindolizine-5-carboxamide

Using the 5-methyl-8-oxo-6,7-dihydroindolizine-5-carboxylic acid (472 mg, 2.44 mmol) obtained in Reference Example 22, 628 mg (yield: 73%) of the title compound was obtained as a solid according to the method of Reference Example 1.

Reference Example 24

N-(5-Bromo-4-isopropylthiazol-2-yl)-8-oxo-6,7-dihydro-5H-indolizine-5-carboxamide Using commercially available 5-bromo-4-isopropylthiazol-2-amine, 287 mg (yield: 43%) of the title compound was obtained as a solid according to the method of Reference Example 1.

Reference Example 25

Methyl 5-bromo-2-[(8-oxo-6,7-dihydro-5H-indolizine-5-carbonyl)amino]thiazol-4-carboxylate Using commercially available methyl 2-amino-5-bromothiazole-4-carboxylate, 219 mg (yield: 29%) of the title compound was obtained as an amorphous material according to the method of Reference Example 1.

Example 1

8-Oxo-N-(5-phenylthiazol-2-yl)-6,7-dihydro-5H-indolizine-5-carboxamide

To a solution of commercially available 8-oxo-6,7-dihydro-5H-indolizine-5-carboxylic acid (1.5 g, 8.4 mmol), 5-phenylthiazol-2-amine described in Journal of Medicinal Chemistry 1983, 26, 1158-1163 (1.0 g, 5.7 mmol), N,N-dimethylpyridin-4-amine (0.14 g, 1.1 mmol) and N,N-diisopropylethylamine (2.5 mL, 14 mmol) in dichloromethane (50 mL) was added commercially available 2,4,6-triisopropylsulfonyl chloride (2.5 g, 8.3 mmol) at room temperature, followed by stirring for 3 hours. After the reaction solution was diluted by adding dichloromethane, a saturated aqueous solution of sodium bicarbonate was added for neutralization and washing. After organic layers were dried over anhydrous sodium sulfate, the solvent was distilled off under reduced pressure. The residue was purified by silica-gel column chromatography (dichloromethane/methanol=99/1-95/5) to obtain 1.59 g (yield: 83%) of the title compound as a solid.

Example 2

Methyl 4-[2-[(8-oxo-6,7-dihydro-5H-indolizine-5-carbonyl)amino]thiazol-5-yl]benzoate Using the methyl 4-(2-aminothiazol-5-yl)benzoate described in International Publication No. WO 2012121168, 18.4 g (yield: 54%) of the title compound was obtained as a solid according to the method of Example 1.

Example 3

N-[5-[4-(Dimethylcarbamoyl)phenyl]thiazol-2-yl]-8-oxo-6,7-dihydro-5H-indolizine-5-carboxamide Using the 4-(2-aminothiazol-5-yl)-N,N-dimethylbenzamide obtained in Reference Example 11, 7.17 g (yield: 75%) of the title compound was obtained as a solid according to the method of Example 1.

Example 4

N-[5-(1,3-Benzodioxol-5-yl)thiazol-2-yl]-8-oxo-6,7-dihydro-5H-indolizine-5-carboxamide Using the 5-(1,3-benzodioxol-5-yl)thiazol-2-amine obtained in Reference Example 12, 130 mg (yield: 62%) of the title compound was obtained as a solid according to the method of Example 1.

Example 5

4-[2-[(8-Oxo-6,7-dihydro-5H-indolizine-5-carbonyl)amino]thiazol-5-yl]benzoic acid To a mixed solution of the methyl 4-[2-[(8-oxo-6,7-dihydro-5H-indolizine-5-carbonyl)amino]thiazol-5-yl]benzoate (383 mg, 0.969 mmol) obtained in Example 2 with ethanol (3 mL) and water (2 mL) was added a 1N sodium hydroxide aqueous solution (3.8 mL, 3.8 mmol), followed by stirring at 50° C. for 4 hours. Water was added to the reaction solution, followed by neutralization with 1N hydrochloric acid, and the precipitated solid was collected by filtration. The solid obtained was washed with water and thereafter dried to obtain 326 mg (yield: 88%) of the title compound as a solid.

Example 6

N-[5-(4-Carbamoylphenyl)thiazol-2-yl]-8-oxo-6,7-dihydro-5H-indolizine-5-carboxamide To a solution of the 4-[2-[(8-oxo-6,7-dihydro-5H-indolizine-5-carbonyl)amino]thiazol-5-yl]benzoic acid obtained in Example 5 (17 mg, 0.045 mmol) in N,N-dimethylformamide (1 mL) were added [dimethylamino(triazolo[4,5-b]pyridin-3-yloxy)methylene]-dimethyl-ammonium hexafluorophosphate (25 mg, 0.067 mmol), N,N-diisopropylethylamine (39 µL, 0.22 mmol) and a 7M ammonia methanol solution (64 µL, 0.45 mmol) at room temperature, followed by stirring for 15 hours. The reaction solution was purified by direct silica-gel column chromatography (dichloromethane/50% methanol ethyl acetate solution=95/5-90/10) to obtain 4.9 mg (yield: 29%) of the title compound.

Example 7

N-[5-(4-Cyanophenyl)thiazol-2-yl]-8-oxo-6,7-dihydro-5H-indolizine-5-carboxamide

Using the 4-(2-aminothiazol-5-yl)benzonitrile obtained in Reference Example 13, 9.0 mg (yield: 60%) of the title compound was obtained according to the method of Example 1.

Example 8

N-[5-[4-[2-(Dimethylamino)-2-oxo-ethoxy]phenyl]thiazol-2-yl]-8-oxo-6,7-dihydro-5H-indolizine-5-carboxamide To a mixed solution of the methyl 2-[4-[2-[(8-oxo-6,7-dihydro-5H-indolizine-5-carbonyl)amino]thiazol-5-yl]phenoxy]acetate obtained in Reference Example 16 (84 mg, 0.197 mmol) in tetrahydrofuran (8.0 mL) and methanol (3.0 mL) was added a 5N aqueous solution of sodium hydroxide (0.20 mL, 1.0 mmol) at room temperature, followed by stirring and thereafter standing overnight. After neutralization with 5N hydrochloric acid, the solvent was distilled off under reduced pressure, to obtain a solid. To a solution of the solid obtained in N,N-dimethylformamide (3 mL) were added N,N-diisopropylethylamine (52 µL, 0.30 mmol) and a 2.0M solution of dimethylamine tetrahydrofuran (0.50 mL, 1.0 mmol) at room temperature. Thereafter, [dimethylamino(triazolo[4,5-b]pyridin-3-yloxy)methylene]dimethylammonium hexafluorophosphate (42 mg, 0.11 mmol) was further added thereto, followed by stirring for 3 hours. After the reaction solution was diluted by adding dichloromethane, a saturated aqueous solution of sodium bicarbonate was added for neutralization and washing. After the organic layers were dried over anhydrous sodium sulfate, the solvent was distilled off under reduced pressure. The residue was purified by silica-gel column chromatography (dichloromethane/methanol=99/1-95/5) to obtain 39.1 mg (yield: 89%) of the title compound as a solid.

Example 9

8-Oxo-N-[5-[4-(trifluoromethoxy)phenyl]thiazol-2-yl]-6,7-dihydro-5H-indolizine-5-carboxamide To a solution of commercially available 8-oxo-6,7-dihydro-5H-indolizine-5-carboxylic acid (109 mg, 0.61 mmol), the 5-[4-(trifluoromethoxy)phenyl]thiazol-2-amine obtained in Reference Example 9 (127 mg, 0.488 mmol) and 3-hydroxytriazole [4,5-b]pyridine (128 mg, 0.941 mmol) in dichloromethane (3 mL) were added 1-ethyl-3-(3-dimethylaminopropyl)carbodiimide hydrochloride (352 mg, 1.84 mmol) and N,N-diisopropylethylamine (0.531 mL, 3.05 mmol) at room temperature, followed by stirring for 2 hours at room temperature. The reaction solution was diluted with dichloromethane and thereafter washed with water and a saturated aqueous solution of sodium chloride. The organic layers were dried over anhydrous sodium sulfate and thereafter filtered to distill off the solvent under reduced pressure. The residue was purified by silica-gel column chromatography (n-hexane/ethyl acetate solution=3/1-0/1) to obtain 74.3 mg (yield: 29%) of the title compound as a solid.

Example 10

(5R)-8-Oxo-N-[5-[4-(trifluoromethoxy)phenyl]thiazol-2-yl]-6,7-dihydro-5H-indolizine-5-carboxamide and (5S)-8-oxo-N-[5-[4-(trifluoromethoxy)phenyl]thiazol-2-yl]-6,7-dihydro-5H-indolizine-5-carboxamide Using the 8-oxo-N-[5-[4-(trifluoromethoxy)phenyl]thiazol-2-yl]-6,7-dihydro-5H-indolizine-5-carboxamide obtained in Example 9, optical resolution was performed by HPLC (column: YMC CHIRAL ART Cellulose-SB (5 μm) 250×30 mm I.D., flow rate: 31.8 ml/min, and solvent: n-hexane/ethanol=70/30). After the first peak eluted earlier was collected, the solvent was distilled off under reduced pressure to obtain the title compound (48 mg, optical purity: 99.9% ee) as a solid. Further, after the second peak eluted later was collected, the solvent was distilled off under reduced pressure to obtain the title compound (48 mg, optical purity: 99.8% ee) as a solid.

Example 11

N-[5-(4-Tert-butoxyphenyl)thiazol-2-yl]-8-oxo-6,7-dihydro-5H-indolizine-5-carboxamide To a mixture of the N-(5-bromothiazol-2-yl)-8-oxo-6,7-dihydro-5H-indolizine-5-carboxamide obtained in Reference Example 1 (137 mg, 0.401 mmol), commercially available (4-tert-butoxyphenyl)boronic acid (389 mg, 2.01 mmol) and cesium carbonate (670 mg, 2.06 mmol) were added N,N-dimethylformamide (2 mL) and water (1 mL). Thereafter, chloro(2-dicyclohexylphosphino-2',4',6'-triisopropyl-1,1'-biphenyl)[2-(2'-amino-1,1'-biphenyl)]palladium (II) (33.2 mg, 0.042 mmol) was added thereto, followed by stirring at 90° C. under a nitrogen atmosphere for 5 hours. After water was added to the reaction solution, it was extracted with ethyl acetate. After organic layers were washed with saturated saline and dried over anhydrous sodium sulfate, the solvent was distilled off under reduced pressure. The residue was purified by silica-gel column chromatography (n-hexane/ethyl acetate=3/1-0/1) to obtain 63.3 mg (yield: 39%) of the title compound as a solid.

Example 12

N-[5-(4-Chlorophenyl)thiazol-2-yl]-8-oxo-6,7-dihydro-5H-indolizine-5-carboxamide Using commercially available 4-chlorophenylboronic acid, 11.0 mg (yield: 6.4%) of the title compound was obtained as a solid according to the method of Example 11.

Example 13

N-[5-(3-Chlorophenyl)thiazol-2-yl]-8-oxo-6,7-dihydro-5H-indolizine-5-carboxamide Using commercially available 5-(3-chlorophenyl)thiazol-2-amine, 158 mg (yield: 48%) of the title compound was obtained as a solid according to the method of Example 9.

Example 14

N-[5-(2-Chlorophenyl)thiazol-2-yl]-8-oxo-6,7-dihydro-5H-indolizine-5-carboxamide Using commercially available 2-chlorophenylboronic acid, 13.2 mg (yield: 8.0%) of the title compound was obtained according to the method of Example 11.

Example 15

N-[5-(3-Fluorophenyl)thiazol-2-yl]-8-oxo-6,7-dihydro-5H-indolizine-5-carboxamide Using commercially available 5-(3-fluorophenyl)thiazol-2-amine, 127 mg (yield: 87%) of the title compound was obtained as a solid according to the method of Example 1.

Example 16

N-[5-(4-Fluorophenyl)thiazol-2-yl]-8-oxo-6,7-dihydro-5H-indolizine-5-carboxamide Using commercially available 5-(4-fluorophenyl)thiazol-2-amine, 198 mg (yield: 64%) of the title compound was obtained as a solid according to the method of Example 1.

Example 17

N-[5-(2-Fluorophenyl)thiazol-2-yl]-8-oxo-6,7-dihydro-5H-indolizine-5-carboxamide Using commercially available 5-(2-fluorophenyl)thiazol-2-amine, 119 mg (yield: 82%) of the title compound was obtained as a solid according to the method of Example 1.

Example 18

8-Oxo-N-[5-(p-tolyl)thiazol-2-yl]-6,7-dihydro-5H-indolizine-5-carboxamide

Using commercially available 4-methylphenylboronic acid, 24.7 mg (yield: 18%) of the title compound was obtained as a solid according to the method of Example 11.

Example 19

N-[5-(o-Tolyl)thiazol-2-yl]-8-oxo-6,7-dihydro-5H-indolizine-5-carboxamide

Using commercially available 2-methylphenylboronic acid, 16.6 mg (yield: 11%) of the title compound was obtained as a solid according to the method of Example 11.

Example 20

N-[5-(m-Tolyl)thiazol-2-yl]-8-oxo-6,7-dihydro-5H-indolizine-5-carboxamide

Using commercially available 5-(m-tolyl)thiazol-2-amine, 115 mg (yield: 58%) of the title compound was obtained according to the method of Example 9.

Example 21

8-Oxo-N-[5-[4-(trifluoromethyl)phenyl]thiazol-2-yl]-6,7-dihydro-5H-indolizine-5-carboxamide Using commercially available [4-(trifluoromethyl)phenyl]boronic acid, 32.9 mg (yield: 17%) of the title compound was obtained according to the method of Example 11.

Example 22

N-[5-[4-(2-Methoxyphenyl)phenyl]thiazol-2-yl]-8-oxo-6,7-dihydro-5H-indolizine-5-carboxamide Using commercially available [4-(2-methoxyphenyl)phenyl]boronic acid, 3.6 mg (yield: 16%) of the title compound was obtained according to the method of Example 11.

Example 23

8-Oxo-N-[5-[4-(p-tolyl)phenyl]thiazol-2-yl]-6,7-dihydro-5H-indolizine-5-carboxamide Using commercially available [4-(p-tolyl)phenyl]boronic acid, 9.0 mg (yield: 42%) of the title compound was obtained according to the method of Example 11.

Example 24

N-[5-(2-Naphthyl)thiazol-2-yl]-8-oxo-6,7-dihydro-5H-indolizine-5-carboxamide

Using commercially available 4,4,5,5-tetramethyl-2-(2-naphthyl)-1,3,2-dioxaborolane, 1.6 mg (yield: 8.2%) of the title compound was obtained according to the method of Example 11.

Example 25

8-Oxo-N-[5-[3-(trifluoromethoxy)phenyl]thiazol-2-yl]-6,7-dihydro-5H-indolizine-5-carboxamide Using commercially available [3-(trifluoromethoxy)phenyl]boronic acid, 9.0 mg (yield: 43%) of the title compound was obtained according to the method of Example 11.

Example 26

N-[5-(4-methoxyphenyl)thiazol-2-yl]-8-oxo-6,7-dihydro-5H-indolizine-5-carboxamide Using commercially available (4-methoxyphenyl)boronic acid, 19.7 mg (yield: 17%) of the title compound was obtained as a solid according to the method of Example 11.

Example 27

N-[5-(3-Methoxyphenyl)thiazol-2-yl]-8-oxo-6,7-dihydro-5H-indolizine-5-carboxamide Using commercially available (3-methoxyphenyl)boronic acid, 1.9 mg (yield: 38%) of the title compound was obtained according to the method of Example 11.

Example 28

N-[5-[2-Methyl-4-(trifluoromethoxy)phenyl]thiazol-2-yl]-8-oxo-6,7-dihydro-5H-indolizine-5-carboxamide Using commercially available [2-methyl-4-(trifluoromethoxy)phenyl]boronic acid, 4.2 mg (yield: 19%) of the title compound was obtained according to the method of Example 11.

Example 29

N-[5-[3-Methyl-4-(trifluoromethoxy)phenyl]thiazol-2-yl]-8-oxo-6,7-dihydro-5H-indolizine-5-carboxamide Using commercially available [3-methyl-4-(trifluoromethoxy)phenyl]boronic acid, 8.4 mg (yield: 38%) of the title compound was obtained according to the method of Example 11.

Example 30

N-[5-[3-Chloro-4-(trifluoromethoxy)phenyl]thiazol-2-yl]-8-oxo-6,7-dihydro-5H-indolizine-5-carboxamide Using commercially available [3-chloro-4-(trifluoromethoxy)phenyl]boronic acid, 2.8 mg (yield: 12%) of the title compound was obtained according to the method of Example 11.

Example 31

N-[5-[3-(Hydroxymethyl)-4-(trifluoromethoxy)phenyl]thiazol-2-yl]-8-oxo-6,7-dihydro-5H-indolizine-5-carboxamide Using commercially available [3-(hydroxymethyl)-4-(trifluoromethoxy)phenyl]boronic acid, 9.1 mg (yield: 40%) of the title compound was obtained according to the method of Example 11.

Example 32

N-[5-(4-Benzyloxyphenyl)thiazol-2-yl]-8-oxo-6,7-dihydro-5H-indolizine-5-carboxamide Using commercially available (4-benzyloxyphenyl)boronic acid, 7.6 mg (yield: 34%) of the title compound was obtained according to the method of Example 11.

Example 33

N-[5-(4-Isopropoxyphenyl)thiazol-2-yl]-8-oxo-6,7-dihydro-5H-indolizine-5-carboxamide Using commercially available (4-isopropoxyphenyl)boronic acid, 29.0 mg (yield: 24%) of the title compound was obtained as a solid according to the method of Example 11.

Example 34

N-(4-Methyl-5-phenylthiazol-2-yl)-8-oxo-6,7-dihydro-5H-indolizine-5-carboxamide Using commercially available 4-methyl-5-phenylthiazol-2-amine, 160 mg (yield: 82%) of the title compound was obtained according to the method of Example 9.

Example 35

N-[5-(4-tert-Butoxyphenyl)-4-methylthiazol-2-yl]-8-oxo-6,7-dihydro-5H-indolizine-5-carboxamide To a mixture of the N-(5-bromo-4-methylthiazol-2-yl)-8-oxo-6,7-dihydro-5H-indolizine-5-carboxamide obtained in Reference Example 4 (106 mg, 0.300 mmol), commercially available (4-tert-butoxyphenyl)boronic acid (292 mg, 1.50 mmol) and cesium carbonate (596 mg, 1.83 mmol) were added N,N-dimethylformamide (1.5 mL) and water (1 mL). Thereafter, chloro(2-dicyclohexylphosphino-2',4',6'-triisopropyl-1,1'-biphenyl)[2-(2'-amino-1,1'-biphenyl)]palladium (II) (25.0 mg, 0.032 mmol) was added thereto, followed by stirring at 90° C. under a nitrogen atmosphere for 5 hours. After water was added to the reaction solution, it was extracted with ethyl acetate. After organic layers were washed with saturated saline and dried over anhydrous sodium sulfate, the solvent was distilled off under reduced pressure. The residue was purified by silica-gel column chromatography (n-hexane/ethyl acetate=3/1-0/1). Thereafter, the solid obtained was washed with diethyl ether to obtain 65.0 mg (yield: 51%) of the title compound as a solid.

Example 36

N-[4-Methyl-5-[4-(trifluoromethoxy)phenyl]thiazol-2-yl]-8-oxo-6,7-dihydro-5H-indolizine-5-carboxamide Using commercially available [4-(trifluoromethoxy)phenyl]boronic acid, 72.0 mg (yield: 49%) of the title compound was obtained according to the method of Example 35.

Example 37

N-[5-[4-(Hydroxymethyl)phenyl]thiazol-2-yl]-8-oxo-6,7-dihydro-5H-indolizine-5-carboxamide Using commercially available [4-(hydroxymethyl)phenyl]boronic acid, 5.3 mg (yield: 29%) of the title compound was obtained according to the method of Example 11.

Example 38

N-[5-[4-(2-Methoxyethoxy)phenyl]thiazol-2-yl]-8-oxo-6,7-dihydro-5H-indolizine-5-carboxamide Using commercially available [4-(2-methoxyethoxy)phenyl]boronic acid, 0.6 mg (yield: 2.7%) of the title compound was obtained according to the method of Example 11.

Example 39

N-[5-[4-(Difluoromethoxy)phenyl]thiazol-2-yl]-8-oxo-6,7-dihydro-5H-indolizine-5-carboxamide Using commercially available [4-(difluoromethoxy)phenyl]boronic acid, 7.0 mg (yield: 35%) of the title compound was obtained according to the method of Example 11.

Example 40

N-[5-(2,2-Difluoro-1,3-benzodioxol-5-yl)thiazol-2-yl]-8-oxo-6,7-dihydro-5H-indolizine-5-carboxamide Using commercially available (2,2-difluoro-1,3-benzodioxol-5-yl)boronic acid, 9.4 mg (yield: 45%) of the title compound was obtained according to the method of Example 11.

Example 41

N-[5-(4-Morpholinophenyl)thiazol-2-yl]-8-oxo-6,7-dihydro-5H-indolizine-5-carboxamide Using commercially available 4-[4-(4,4,5,5-tetramethyl-1,3,2-dioxaborolan-2-yl)phenyl]morpholine, 27.6 mg (yield: 24%) of the title compound was obtained as a solid according to the method of Example 11.

Example 42

N-[5-[4-(Dimethylsulfamoyl)phenyl]thiazol-2-yl]-8-oxo-6,7-dihydro-5H-indolizine-5-carboxamide Using commercially available [4-(dimethylsulfamoyl)phenyl]boronic acid, 9.7 mg (yield: 44%) of the title compound was obtained according to the method of Example 11.

Example 43

N-[5-(4-Benzyloxy-3-fluorophenyl)thiazol-2-yl]-8-oxo-6,7-dihydro-5H-indolizine-5-carboxamide Using commercially available (4-benzyloxy-3-fluorophenyl)boronic acid, 62.8 mg (yield: 33%) of the title compound was obtained as a solid according to the method of Example 11.

Example 44

N-[5-(4-Benzyloxy-2-fluorophenyl)thiazol-2-yl]-8-oxo-6,7-dihydro-5H-indolizine-5-carboxamide Using commercially available (4-benzyloxy-2-fluorophenyl)boronic acid, 9.7 mg (yield: 42%) of the title compound was obtained according to the method of Example 11.

Example 45

8-Oxo-N-[5-[4-(2,2,2-trifluoroethoxy)phenyl]thiazol-2-yl]-6,7-dihydro-5H-indolizine-5-carboxamide Using commercially available [4-(2,2,2-trifluoroethoxy)phenyl]boronic acid, 53.0 mg (yield: 28%) of the title compound was obtained as a solid according to the method of Example 11.

Example 46

8-Oxo-N-[5-(4-phenoxyphenyl)thiazol-2-yl]-6,7-dihydro-5H-indolizine-5-carboxamide Using commercially available (4-phenoxyphenyl)boronic acid, 53.0 mg (yield: 29%) of the title compound was obtained as a solid according to the method of Example 11.

Example 47

N-[5-(4-Bromophenyl)thiazol-2-yl]-8-oxo-6,7-dihydro-5H-indolizine-5-carboxamide

Using commercially available 5-(4-bromophenyl)thiazol-2-amine, 755 mg (yield: 59%) of the title compound was obtained as a solid according to the method of Example 9.

Example 48 tert-Butyl[4-[2-[(8-oxo-6,7-dihydro-5H-indolizine-5-carbonyl)amino]thiazol-5-yl]phenyl]carbonate Using commercially available (4-tert-butoxycarbonyloxyphenyl)boronic acid, 1.0 mg (yield: 4.3%) of the title compound was obtained according to the method of Example 11.

Example 49

N-[5-(4-Isobutoxyphenyl)thiazol-2-yl]-8-oxo-6,7-dihydro-5H-indolizine-5-carboxamide Using commercially available (4-isobutoxyphenyl)boronic acid, 6.5 mg (yield: 32%) of the title compound was obtained according to the method of Example 11.

Example 50

N-[5-(Cyclohexen-1-yl)thiazol-2-yl]-8-oxo-6,7-dihydro-5H-indolizine-5-carboxamide Using commercially available 2-(cyclohexen-1-yl)-4,4,5,5-tetramethyl-1,3,2-dioxaborolane, 13.8 mg (yield: 13%) of the title compound was obtained as a solid according to the method of Example 11.

Example 51 tert-Butyl 4-[2-[(8-oxo-6,7-dihydro-5H-indolizine-5-carbonyl)amino]thiazol-5-yl]-3,6-dihydro-2H-pyridine-1-carboxylate Using commercially available tert-butyl 4-(4,4,5,5-tetramethyl-1,3,2-dioxaborolan-2-yl)-3,6-dihydro-2H-pyridine-1-carboxylate, 7.7 mg (yield: 35%) of the title compound was obtained according to the method of Example 11.

Example 52

N-[5-(5-Chloro-6-isobutoxy-3-pyridyl)thiazol-2-yl]-8-oxo-6,7-dihydro-5H-indolizine-5-carboxamide Using commercially available (5-chloro-6-isobutoxy-3-pyridyl)boronic acid, 3.2 mg (yield: 15%) of the title compound was obtained according to the method of Example 11.

Example 53 tert-Butyl 3-[2-[(8-oxo-6,7-dihydro-5H-indolizine-5-carbonyl)amino]thiazol-5-yl]-2,5-dihydropyrrole-1-carboxylate Using commercially available tert-butyl 3-(4,4,5,5-tetramethyl-1,3,2-dioxaborolan-2-yl)-2,5-dihydropyrrole-1-carboxylate, 7.6 mg (yield: 35%) of the title compound was obtained according to the method of Example 11.

Example 54

N-[5-(5-Methyl-2-furyl)thiazol-2-yl]-8-oxo-6,7-dihydro-5H-indolizine-5-carboxamide Using commercially available 4,4,5,5-tetramethyl-2-(5-methyl-2-furyl)-1,3,2-dioxaborolane, 7.3 mg (yield: 43%) of the title compound was obtained according to the method of Example 11.

Example 55

N-[5-(2,4-Dimethylthiazol-5-yl)thiazol-2-yl]-8-oxo-6,7-dihydro-5H-indolizine-5-carboxamide Using commercially available 2,4-dimethyl-5-(4,4,5,5-tetramethyl-1,3,2-dioxaborolan-2-yl)thiazole, 3.6 mg (yield: 19%) of the title compound was obtained according to the method of Example 11.

Example 56

N-[5-(5-Chloro-2-thienyl)thiazol-2-yl]-8-oxo-6,7-dihydro-5H-indolizine-5-carboxamide Using commercially available (5-chloro-2-thienyl)boronic acid, 1.0 mg (yield: 5.2%) of the title compound was obtained according to the method of Example 11.

Example 57

N-[5-(4-Acetylphenyl)thiazol-2-yl]-8-oxo-6,7-dihydro-5H-indolizine-5-carboxamide Using commercially available (4-acetylphenyl)boronic acid, 6.2 mg (yield: 33%) of the title compound was obtained according to the method of Example 11.

Example 58

1-Oxo-N-[5-[4-(trifluoromethoxy)phenyl]thiazol-2-yl]-2,3-dihydropyrrolidine-3-carboxamide Using commercially available 1-oxo-2,3-dihydropyrrolidine-3-carboxylic acid, 71.9 mg (yield: 29%) of the title compound was obtained as a solid according to the method of Example 9.

Example 59

8-Oxo-N-[6-[4-(trifluoromethoxy)phenyl]-1,3-benzothiazol-2-yl]-6,7-dihydro-5H-indolizine-5-carboxamide Using the N-(6-bromo-1,3-benzothiazol-2-yl)-8-oxo-6,7-dihydro-5H-indolizine-5-carboxamide obtained in Reference Example 5 and commercially available [4-(trifluoromethoxy)phenyl]boronic acid, 59.5 mg (yield: 46%) of the title compound was obtained as a solid according to the method of Example 11.

Example 60

N-[6-[4-(Difluoromethoxy)phenyl]-1,3-benzothiazol-2-yl]-8-oxo-6,7-dihydro-5H-indolizine-5-carboxamide Using the N-(6-bromo-1,3-benzothiazol-2-yl)-8-oxo-6,7-dihydro-5H-indolizine-5-carboxamide obtained in Reference Example 5 and commercially available [4-(difluoromethoxy)phenyl]boronic acid, 11.2 mg (yield: 49%) of the title compound was obtained according to the method of Example 11.

Example 61

N-[6-(2,2-Difluoro-1,3-benzodioxol-5-yl)-1,3-benzothiazol-2-yl]-8-oxo-6,7-dihydro-5H-indolizine-5-carboxamide Using the N-(6-bromo-1,3-benzothiazol-2-yl)-8-oxo-6,7-dihydro-5H-indolizine-5-carboxamide obtained in Reference Example 5 and commercially available (2,2-difluoro-1,3-benzodioxol-5-yl)boronic acid, 12.6 mg (yield: 54%) of the title compound was obtained according to the method of Example 11.

Example 62

2-Methyl-8-oxo-N-[5-[4-(trifluoromethoxy)phenyl]thiazol-2-yl]-6,7-dihydro-5H-indolizine-5-carboxamide To a mixture of the 2-bromo-8-oxo-N-[5-[4-(trifluoromethoxy)phenyl]thiazol-2-yl]-6,7-dihydro-5H-indolizine-5-carboxamide obtained in Reference Example 18 (42.8 mg, 0.0856 mmol), commercially available 2,4,6-trimethyl-1,3,5,2,4,6-trioxatriborinane (0.127 mL, 0.908 mmol) and potassium carbonate (184 mg, 1.33 mmol) were added 1,4-dioxane (1.5 mL) and water (0.5 mL). Thereafter, chloro(2-dicyclohexylphosphino-2'4'6'-triisopropyl-1,1'-biphenyl)[2-(2'-amino-1,1'-biphenyl)]palladium(II) (15.3 mg, 0.019 mmol) was added thereto, followed by stirring at 100° C. under a nitrogen atmosphere for 4 hours. Since the raw materials remained, the same operation was repeated again, and disappearance of the raw materials was confirmed. After water was added to the reaction solution, it was extracted with ethyl acetate. After the organic layers were washed with saturated saline and dried over anhydrous sodium sulfate, the solvent was distilled off under reduced pressure. The residue was purified by silica-gel column chromatography (n-hexane/ethyl acetate=9/1-1/1) to obtain 5.6 mg (yield: 15%) of the title compound as a solid.

Example 63

N-[5-(4-tert-Butoxyphenyl)thiazol-2-yl]-2-methyl-8-oxo-6,7-dihydro-5H-indolizine-5-carboxamide Using the N-(5-bromothiazol-2-yl)-2-methyl-8-oxo-6,7-dihydro-5H-indolizine-5-carboxamide obtained in Reference Example 19, 6.4 mg (yield: 22%) of the title compound was obtained as a solid according to the method of Example 11.

Example 64

2-Chloro-8-oxo-N-[5-[4-(trifluoromethoxy)phenyl]thiazol-2-yl]-6,7-dihydro-5H-indolizine-5-carboxamide To a mixed solution of the methyl 2-chloro-8-oxo-6,7-dihydro-5H-indolizine-5-carboxylate obtained in Reference Example 20 (66.2 mg, 0.291 mmol) in ethanol (1 mL) and tetrahydrofuran (1 mL) was added a 1N sodium hydroxide aqueous solution (0.5 mL, 0.5 mmol) at room temperature, followed by stirring for 2 hours. After water was added to the reaction solution, the mixture was acidified by adding 1N hydrochloric acid and extracted with ethyl acetate. After the organic layers were washed with saturated saline and dried over anhydrous sodium sulfate, the solvent was distilled off under reduced pressure. Using the residue obtained (carboxylic acid compound 62 mg), 68.0 mg (yield: 37%) of the title compound was obtained as a solid according to the method of Example 9.

Example 65

5-Methyl-8-oxo-N-[5-[4-trifluoromethoxy]phenyl]thiazol-2-yl]-6,7-dihydroindolizine-5-carboxamide To a mixture of the N-(5-bromothiazol-2-yl)-5-methyl-8-oxo-6,7-dihydroindolizine-5-carboxamide obtained in Reference Example 23 (168 mg, 0.475 mmol), commercially available [4-(trifluoromethoxy)phenyl]boronic acid (588 mg, 2.86 mmol) and cesium carbonate (1.03 g, 3.16 mmol) were added N,N-dimethylformamide (2 mL) and water (1 mL). Thereafter, chloro(2-dicyclohexylphosphino-2'4'6'-triisopropyl-1,1'-biphenyl)[2-(2'-amino-1,1'-biphenyl)]palladium(II) (38.6 mg, 0.049 mmol) was added thereto, followed by stirring at 90° C. under a nitrogen atmosphere for 4 hours. After water was added to the reaction solution, it was extracted with ethyl acetate. After the organic layers were washed with saturated saline and dried over anhydrous sodium sulfate, the solvent was distilled off under reduced pressure. The residue was purified by silica-gel column chromatography (n-hexane/ethyl acetate=3/1-0/1) to obtain 59.7 mg (yield: 29%) of the title compound as a solid.

Example 66

5-Methyl-8-oxo-N-[5-(p-tolyl)thiazol-2-yl]-6,7-dihydroindolizine-5-carboxamide

Using commercially available 4-methylphenylboronic acid, 8.6 mg (yield: 47%) of the title compound was obtained according to the method of Example 65.

Example 67

5-Methyl-N-[5-(m-tolyl)thiazol-2-yl]-8 oxo-6,7-dihydroindolizine-5-carboxamide

Using commercially available 3-methylphenylboronic acid, 8.1 mg (yield: 44%) of the title compound was obtained according to the method of Example 65.

Example 68

N-[5-(2,2-Difluoro-1,3-benzodioxol-5-yl)thiazol-2-yl]-5-methyl-8-oxo-6,7-dihydroindolizine-5-carboxamide Using commercially available (2,2-difluoro-1,3-benzodioxol-5-yl)boronic acid, 0.6 mg (yield: 3.0%) of the title compound was obtained according to the method of Example 65.

Example 69

N-[5-(4-Isopropoxyphenyl)thiazol-2-yl]-5-methyl-8-oxo-6,7-dihydroindolizine-5-carboxamide Using commercially available (4-isopropoxyphenyl)boronic acid, 6.8 mg (yield: 33%) of the title compound was obtained according to the method of Example 65.

Example 70

5-Methyl-N-[5-[3-methyl-4-(trifluoromethoxy)phenyl]thiazol-2-yl]-8-oxo-6,7-dihydroindolizine-5-carboxamide Using commercially available [3-methyl-4-(trifluoromethoxy)phenyl]boronic acid, 8.3 mg (yield: 37%) of the title compound was obtained according to the method of Example 65.

Example 71

N-[5-[3-Chloro-4-(trifluoromethoxy)phenyl]thiazol-2-yl]-5-methyl-8-oxo-6,7-dihydroindolizine-5-carboxamide Using commercially available [3-chloro-4-(trifluoromethoxy)phenyl]boronic acid, 5.0 mg (yield: 21%) of the title compound was obtained according to the method of Example 65.

Example 72

5-Methyl-8-oxo-N-[5-[3-(trifluoromethoxy)phenyl]thiazol-2-yl]-6,7-dihydroindolizine-5-carboxamide Using commercially available [3-(trifluoromethoxy)phenyl]boronic acid, 7.8 mg (yield: 36%) of the title compound was obtained according to the method of Example 65.

Example 73

8-Oxo-N-[4-[4-(trifluoromethoxy)phenyl]phenyl]-6,7-dihydro-5H-indolizine-5-carboxamide Using the N-(4-bromophenyl)-8-oxo-6,7-dihydro-5H-indolizine-5-carboxamide obtained in Reference Example 2 (1.21 g, 3.62 mmol) and commercially available 4-(trifluoromethoxyphenyl)boronic acid, 1.29 g (yield: 86%) of the title compound was obtained as a solid according to the method of Example 11.

Example 74

N-[4-(2,2-Difluoro-1,3-benzodioxol-5-yl)phenyl]-8-oxo-6,7-dihydro-5H-indolizine-5-carboxamide Using the N-(4-bromophenyl)-8-oxo-6,7-dihydro-5H-indolizine-5-carboxamide obtained in Reference Example 2 and commercially available (2,2-difluoro-1,3-benzodioxol-5-yl)boronic acid, 10.4 mg (yield: 50%) of the title compound was obtained according to the method of Example 11.

Example 75

N-[4-[4-(Difluoromethoxy)phenyl]phenyl]-8-oxo-6,7-dihydro-5H-indolizine-5-carboxamide Using the N-(4-bromophenyl)-8-oxo-6,7-dihydro-5H-indolizine-5-carboxamide obtained in Reference Example 2 and commercially available [4-(difluoromethoxy)phenyl]boronic acid, 11.5 mg (yield: 58%) of the title compound was obtained according to the method of Example 11.

Example 76

N-[4-[3-Chloro-4-(trifluoromethoxy)phenyl]phenyl]-8-oxo-6,7-dihydro-5H-indolizine-5-carboxamide Using the N-(4-bromophenyl)-8-oxo-6,7-dihydro-5H-indolizine-5-carboxamide obtained in Reference Example 2 and commercially available [3-chloro-4-(trifluoromethoxy)phenyl]boronic acid, 7.0 mg (yield: 31%) of the title compound was obtained according to the method of Example 11.

Example 77

3-Bromo-8-oxo-N-[4-[4-(trifluoromethoxy)phenyl]phenyl]-6,7-dihydro-5H-indolizine-5-carboxamide To a solution of the 8-oxo-N-[4-[4-(trifluoromethoxy)phenyl]phenyl]-6,7-dihydro-5H-indolizine-5-carboxamide obtained in Example 73 (150 mg, 0.363 mmol) in dichloromethane (15 mL) was added N-bromosuccinimide (45.9 mg, 0.258 mmol) at room temperature, followed by stirring for 4.5 hours. The reaction solution was concentrated under reduced pressure, and the residue obtained was purified by silica-gel column chromatography (n-hexane/10% methanol ethyl acetate solution=3/1-1/1) to obtain 93.6 mg (yield: 52%) of the title compound as a solid.

Example 78

N-[2-Fluoro-4-[4-(trifluoromethoxy)phenyl]phenyl]-8-oxo-6,7-dihydro-5H-indolizine-5-carboxamide Using the N-(4-bromo-2-fluorophenyl)-8-oxo-6,7-dihydro-5H-indolizine-5-carboxamide obtained in Reference Example 3 and commercially available [4-(trifluoromethoxy)phenyl]boronic acid, 73.4 mg (yield: 91%) of the title compound was obtained as a solid according to the method of Example 11.

Example 79

N-[4-[3-Chloro-4-(trifluoromethoxy)phenyl]-2-fluorophenyl]-8-oxo-6,7-dihydro-5H-indolizine-5-carboxamide Using the N-(4-bromo-2-fluorophenyl)-8-oxo-6,7-dihydro-5H-indolizine-5-carboxamide obtained in Reference Example 3 and commercially available [3-chloro-4-(trifluoromethoxy)phenyl]boronic acid, 5.0 mg (yield: 21%) of the title compound was obtained according to the method of Example 11.

Example 80

N-[4-(4-tert-Butoxyphenyl)-2-fluorophenyl]-8-oxo-6,7-dihydro-5H-indolizine-5-carboxamide Using the N-(4-bromo-2-fluorophenyl)-8-oxo-6,7-dihydro-5H-indolizine-5-carboxamide obtained in Reference Example 3, 75.0 mg (yield: 84%) of the title compound was obtained as a solid according to the method of Example 11.

Example 81

N-[2-Methyl-4-[4-(trifluoromethoxy)phenyl]phenyl]-8-oxo-6,7-dihydro-5H-indolizine-5-carboxamide Using the N-(4-bromo-2-methylphenyl)-8-oxo-6,7-dihydro-5H-indolizine-5-carboxamide obtained in Reference Example 6 and commercially available [4-(trifluoromethoxy)phenyl]boronic acid, 184 mg (yield: 92%) of the title compound was obtained as a solid according to the method of Example 11.

Example 82

8-Oxo-N-[5-[4-(trifluoromethoxy)phenyl]-2-pyridyl]-6,7-dihydro-5H-indolizine-5-carboxamide Using the N-(5-bromo-2-pyridyl)-8-oxo-6,7-dihydro-5H-indolizine-5-carboxamide obtained in Reference Example 7 and commercially available [4-(trifluoromethoxy)phenyl]boronic acid, 4.0 mg (yield: 17%) of the title compound was obtained according to the method of Example 11.

Example 83

8-Oxo-N-[2-[4-(trifluoromethoxy)phenyl]-1,3-benzothiazol-6-yl]-6,7-dihydro-5H-indolizine-5-carboxamide Using the N-(2-chloro-1,3-benzothiazol-6-yl)-8-oxo-6,7-dihydro-5H-indolizine-5-carboxamide obtained in Reference Example 8 and commercially available [4-(trifluoromethoxy)phenyl]boronic acid, 86.8 mg (yield: 58%) of the title compound was obtained as a solid according to the method of Example 11.

Example 84

N-[5-(2,2-Difluoro-1,3-benzodioxol-5-yl)-4-methylthiazol-2-yl]-8-oxo-6,7-dihydroindolizine-5-carboxamide Using commercially available (2,2-difluoro-1,3-benzodioxol-5-yl)boronic acid, 10.4 mg (yield: 48%) of the title compound was obtained according to the method of Example 35.

Example 85

N-[5-(4-Benzyloxy-3-fluorophenyl)-4-methylthiazol-2-yl]-8-oxo-6,7-dihydro-5H-indolizine-5-carboxamide Using commercially available (4-benzyloxy-3-fluorophenyl)boronic acid, 10.4 mg (yield: 44%) of the title compound was obtained according to the method of Example 35.

Example 86

N-[5-(4-Isobutoxyphenyl)-4-methylthiazol-2-yl]-8-oxo-6,7-dihydro-5H-indolizine-5-carboxamide Using commercially available (4-isobutoxyphenyl)boronic acid, 12.2 mg (yield: 58%) of the title compound was obtained according to the method of Example 35.

Example 87

N-[5-(5-Chloro-6-isobutoxy-3-pyridyl)-4-methylthiazol-2-yl]-8-oxo-6,7-dihydro-5H-indolizine-5-carboxamide Using commercially available (5-chloro-6-isobutoxy-3-pyridyl)boronic acid, 6.6 mg (yield: 29%) of the title compound was obtained according to the method of Example 35.

Example 88

N-[4-Methyl-5-[4-(2,2,2-trifluoroethoxy)phenyl]thiazol-2-yl]-8-oxo-6,7-dihydro-5H-indolizine-5-carboxamide Using commercially available [4-(2,2,2-trifluoroethoxy)phenyl]boronic acid, 13.2 mg (yield: 59%) of the title compound was obtained according to the method of Example 35.

Example 89

N-[4-Methyl-5-[3-methyl-4-(trifluoromethoxy)phenyl]thiazol-2-yl]-8-oxo-6,7-dihydro-5H-indolizine-5-carboxamide Using commercially available [3-methyl-4-(trifluoromethoxy)phenyl]boronic acid, 7.5 mg (yield: 33%) of the title compound was obtained according to the method of Example 35.

Example 90 tert-Butyl 4-[4-methyl-2-[(8-oxo-6,7-dihydro-5H-indolizine-5-carbonyl)amino]thiazol-5-yl]-3,6-dihydro-2H-pyridine-1-carboxylate Using commercially available tert-butyl 4-(4,4,5,5-tetramethyl-1,3,2-dioxaborolan-2-yl)-3,6-dihydro-2H-pyridine-1-carboxylate, 12.8 mg (yield: 56%) of the title compound was obtained according to the method of Example 35.

Example 91

N-[5-[4-(Difluoromethoxy)phenyl]-4-methylthiazol-2-yl]-8-oxo-6,7-dihydro-5H-indolizine-5-carboxamide Using the N-(6-bromo-1,3-benzothiazol-2-yl)-8-oxo-6,7-dihydro-5H-indolizine-5-carboxamide obtained in Reference Example 5 and commercially available [4-(difluoromethoxy)phenyl]boronic acid, 10.9 mg (yield: 52%) of the title compound was obtained according to the method of Example 35.

Example 92

N-[6-[3-Methyl-4-(trifluoromethoxy)phenyl]-1,3-benzothiazol-2-yl]-8-oxo-6,7-dihydro-5H-indolizine-5-carboxamide Using the N-(6-bromo-1,3-benzothiazol-2-yl)-8-oxo-6,7-dihydro-5H-indolizine-5-carboxamide obtained in Reference Example 5 and commercially available [3-methyl-4-(trifluoromethoxy)phenyl]boronic acid, 14.0 mg (yield: 58%) of the title compound was obtained according to the method of Example 11.

Example 93

N-[6-(4-Chlorophenyl)-1,3-benzothiazol-2-yl]-8-oxo-6,7-dihydro-5H-indolizine-5-carboxamide Using the N-(6-bromo-1,3-benzothiazol-2-yl)-8-oxo-6,7-dihydro-5H-indolizine-5-carboxamide obtained in Reference Example 5 and commercially available 4-chlorophenylboronic acid, 2.8 mg (yield: 13%) of the title compound was obtained according to the method of Example 11.

Example 94

N-[6-(4-Fluorophenyl)-1,3-benzothiazol-2-yl]-8-oxo-6,7-dihydro-5H-indolizine-5-carboxamide Using the N-(6-bromo-1,3-benzothiazol-2-yl)-8-oxo-6,7-dihydro-5H-indolizine-5-carboxamide obtained in Reference Example 5 and commercially available 4-fluorophenylboronic acid, 13.0 mg (yield: 64%) of the title compound was obtained according to the method of Example 11.

Example 95

N-[5-(4-Benzoylphenyl)thiazol-2-yl]-8-oxo-6,7-dihydro-5H-indolizine-5-carboxamide Using commercially available 4-benzoylphenylboronic acid, 75.4 mg (yield: 28%) of the title compound was obtained as a solid according to the method of Example 11.

Example 96

N-[4-Isopropyl-5-[4-(trifluoromethoxy)phenyl]thiazol-2-yl]-8-oxo-6,7-dihydro-5H-indolizine-5-carboxamide Using the N-(5-bromo-4-isopropylthiazol-2-yl)-8-oxo-6,7-dihydro-5H-indolizine-5-carboxamide obtained in Reference Example 24 and commercially available [4-(trifluoromethoxy)phenyl]boronic acid, 112.2 mg (yield: 66%) of the title compound was obtained according to the method of Example 35.

Example 97

N-[5-[1-(2-Methylpropanoyl)-3,6-dihydro-2H-pyridin-4-yl]thiazol-2-yl]-8-oxo-6,7-dihydro-5H-indolizine-5-carboxamide To a solution of the tert-butyl 4-[2-[(8-oxo-6,7-dihydro-5H-indolizine-5-carbonyl)amino]thiazol-5-yl]-3,6-dihydro-2H-pyridine-1-carboxylate obtained in Example 51 (139 mg, 0.315 mmol) in dichloromethane (3 mL) was added trifluoroacetic acid (0.6 mL) at room temperature, followed by stirring for 2 hours. The reaction solution was concentrated under reduced pressure and azeotropically concentrated several times by addition of dichloromethane to obtain an oil material (226 mg). To a solution of the obtained oil material (68 mg) and N,N-diisopropylethylamine (0.10 mL) in dichloromethane (3 mL) was added 2-methylpropanoyl chloride (0.032 mL, 0.30 mmol) under ice cooling, followed by stirring for 2 hours. The reaction solution was diluted with dichloromethane and thereafter washed with water and saturated saline. After the organic layers were dried over anhydrous sodium sulfate, the solvent was distilled off under reduced pressure. The residue was purified by silica gel chromatography (n-hexane/ethyl acetate=4/1-1/2) to obtain 50.3 mg (yield: 81%) of the title compound as a solid.

Example 98

N-[5-[1-(Isopropylcarbamoyl)-3,6-dihydro-2H-pyridin-4-yl]thiazol-2-yl]-8-oxo-6,7-dihydro-5H-indolizine-5-carboxamide Using the tert-butyl 4-[2-[(8-oxo-6,7-dihydro-5H-indolizine-5-carbonyl)amino]thiazol-5-yl]-3,6-dihydro-2H-pyridine-1-carboxylate obtained in Example 51 and 2-isocyanatopropane, 30.6 mg (yield: 48%) of the title compound was obtained as a solid according to the method of Example 97.

Example 99

Methyl 2-[(8-oxo-6,7-dihydro-5H-indolizine-5-carbonyl)amino]-5-[4-(2,2,2-trifluoroethoxy)phenyl]thiazole-4-carboxylate Using the methyl 5-bromo-2-[(8-oxo-6,7-dihydro-5H-indolizine-5-carbonyl)amino]thiazole-4-carboxylate obtained in Reference Example 25 and commercially available [4-(2,2,2-trifluoroethoxy)phenyl]boronic acid, 42.3 mg (yield: 31%) of the title compound was obtained according to the method of Example 35.

Example 100

Methyl 5-(4-tert-butoxyphenyl)-2-[(8-oxo-6,7-dihydro-5H-indolizine-5-carbonyl)amino]thiazole-4-carboxylate Using the methyl 5-bromo-2-[(8-oxo-6,7-dihydro-5H-indolizine-5-carbonyl)amino]thiazole-4-carboxylate obtained in Reference Example 25 and commercially available (4-tert-butoxyphenyl)boronic acid, 45.8 mg (yield: 38%) of the title compound was obtained according to the method of Example 35.

Example 101

(5R)—N-[5-(4-tert-Butoxyphenyl)-4-methylthiazol-2-yl]-8-oxo-6,7-dihydro-5H-indolizine-5-carboxamide and (5S)-N-[5-(4-tert-butoxyphenyl)-4-methylthiazol-2-yl]-8-oxo-6,7-dihydro-5H-indolizine-5-carboxamide Using the N-[5-(4-tert-butoxyphenyl)-4-methylthiazol-2-yl]-8-oxo-6,7-dihydro-5H-indolizine-5-carboxamide obtained in Example 35 and YMC CHIRAL ART Cellulose-SC (10 μm) 250×10 mm I.D., flow rate: 2.3 ml/min, solvent: n-hexane/ethanol=40/60), optical resolution was performed. After the first peak eluted earlier was collected, the solvent was distilled off under reduced pressure, to obtain the title compound (53 mg, optical purity: >99% ee) as an amorphous material. Further, after the second peak eluted later was collected, the solvent was distilled off under reduced pressure, to obtain the title compound (53 mg, optical purity: >99% ee) as an amorphous material.

Tables below show the structural formulae and physicochemical data of the compounds synthesized in the Reference Examples and Examples.

TABLE 1-1

| Reference Example No. | Structural formula | Physical and chemical data |
|---|---|---|
| 1 | (structure) | $^1$H-NMR (DMSO-D$_6$) δ: 12.95 (1H, br s), 7.63 (1H, s), 7.21 (1H, t, J = 2.1 Hz), 6.85 (1H, dd, J = 3.9, 1.5 Hz), 6.27 (1H, dd, J = 3.9, 2.1 Hz), 5.35 (1H, dd, J = 5.4, 3.6 Hz), 2.60-2.46 (2H, m), 2.43-2.38 (2H, m); [M + H]+ = 340. |
| 2 | (structure) | $^1$H-NMR (DMSO-D$_6$) δ: 10.57 (1H, s), 7.58 (2H, d, J = 9.1 Hz), 7.52 (2H, d, J = 9.1 Hz), 7.18 (1H, t, J = 2.1 Hz), 6.83 (1H, dd, J = 3.9, 1.5 Hz), 6.26 (1H, dd, J = 3.9, 2.1 Hz), 5.18 (1H, t, J = 3.9 Hz), 2.58-2.41 (4H, m); [M + H]+ = 333. |
| 3 | (structure) | $^1$H-NMR (DMSO-D$_6$) δ: 10.34 (1H, s), 7.85 (1H, t, J = 8.5 Hz), 7.65 (1H, dd, J = 10.6, 2.1 Hz), 7.40 (1H, dd, J = 8.5, 2.1 Hz), 7.18 (1H, t, J = 1.8 Hz), 6.83 (1H, dd, J = 3.6, 1.2 Hz), 6.26 (1H, dd, J = 3.6, 1.8 Hz), 5.34 (1H, t, J = 3.6 Hz), 2.50-2.45 (4H, m); [M + H]+ = 351 |
| 4 | (structure) | $^1$H-NMR (DMSO-D$_6$) δ: 12.88 (1H, br s), 7.20 (1H, t, J = 2.1 Hz), 6.85 (1H, dd, J = 3.9, 1.5 Hz), 6.27 (1H, dd, J = 3.9, 2.1 Hz), 5.33 (1H, t, J = 4.2 Hz), 2.61-2.44 (2H, m), 2.42-2.32 (2H, m), 2.25 (3H, s); [M + H]+ = 354. |
| 5 | (structure) | $^1$H-NMR (DMSO-D$_6$) δ: 13.02 (1H, br s), 8.29 (1H, d, J = 1.8 Hz), 7.73 (1H, d, J = 8.5 Hz), 7.60 (1H, dd, J = 8.5, 1.8 Hz), 7.26 (1H, t, J = 2.1 Hz), 6.87 (1H, dd, J = 3.9, 1.5 Hz), 6.29 (1H, dd, J = 3.9, 2.1 Hz), 5.41 (1H, t, J = 3.9 Hz), 2.62-2.55 (2H, m), 2.45-2.40 (2H, m); [M + H]+ = 390. |

TABLE 1-1-continued

| Reference Example No. | Structural formula | Physical and chemical data |
|---|---|---|
| 6 | | $^1$H-NMR (DMSO-D$_6$) δ: 9.79 (1H, s), 7.47 (1H, s), 7.40-7.35 (2H, m), 7.19 (1H, t, J = 1.5 Hz), 6.83 (1H, dd, J = 3.9, 1.5 Hz), 6.27 (1H, dd, J = 3.9, 2.7 Hz), 5.27 (1H, t, J = 4.2 Hz), 2.56-2.44 (4H, m), 2.22 (3H, s); [M + H]+ = 347. |
| 7 | | $^1$H-NMR (DMSO-D$_6$) δ: 11.19 (1H, s), 8.50 (1H, s), 8.05-8.00 (2H, m), 7.20 (1H, t, J = 1.8 Hz), 6.83 (1H, dd, J = 3.9, 1.2 Hz), 6.26 (1H, dd, J = 3.9, 1.8 Hz), 5.32 (1H, br s), 2.50-2.39 (4H, m); [M + H]+ = 334. |
| 8 | | $^1$H-NMR (DMSO-D$_6$) δ: 10.76 (1H, s), 8.51 (1H, d, J = 1.8 Hz), 7.93 (1H, d, J = 8.8 Hz), 7.62 (1H, dd, J = 8.8, 1.8 Hz), 7.20 (1H, d, J = 1.8 Hz), 6.85 (1H, dd, J = 3.9, 1.5 Hz), 6.27 (1H, dd, J = 3.9, 1.8 Hz), 5.24 (1H, t, J = 3.9 Hz), 2.61-2.43 (4H, m); [M + H]+ = 346. |
| 9 | | $^1$H-NMR (CDCl$_3$) δ: 7.43-7.42 (2H, m), 7.29 (1H, s), 7.19 (2H, d, J = 7.9 Hz), 5.00 (2H, br s); [M + H]+ = 261. |

TABLE 1-2

| | | |
|---|---|---|
| 10 | | $^1$H-NMR (CDCl$_3$) δ: 11.38 (1H, br s), 7.62 (1H, s), 7.55-7.53 (2H, m), 7.46-7.44 (2H, m), 3.12 (3H, br s), 3.04 (3H, br s), 1.62 (9H, s); [M + H]+ = 348. |
| 11 | | $^1$H-NMR (CDCl$_3$) δ: 7.45-7.40 (4H, m), 7.36 (1H, s), 5.01 (2H, br s), 3.12 (3H, br s), 3.02 (3H, br s). |
| 12 | | $^1$H-NMR (CDCl$_3$) δ: 7.16 (1H, s), 6.92 (1H, d, J = 2.0 Hz), 6.87 (1H, dd, J = 7.8, 2.0 Hz), 6.79 (1H, d, J = 7.8 Hz), 5.98 (2H, s), 4.90 (2H, br s); [M + H]+ = 221. |

TABLE 1-2-continued
| | | |
|---|---|---|
| 13 | 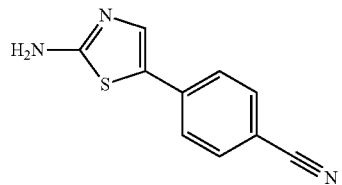 [SMILES: N#Cc1ccc(-c2cnc(N)s2)cc1] | ¹H-NMR (CDCl₃) δ: 7.61 (2H, dt, J = 8.5, 1.8 Hz), 7.48 (2H, dt, J = 8.5, 1.8 Hz), 7.45 (1H, s), 5.10 (2H, br s); [M + H]+ = 202. |
| 14 | 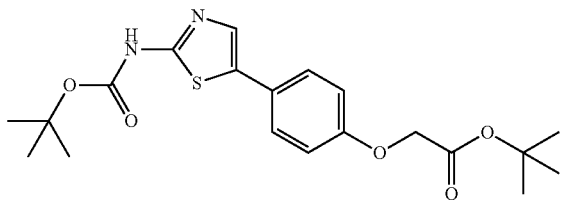 [SMILES: CC(C)(C)OC(=O)COc1ccc(-c2cnc(NC(=O)OC(C)(C)C)s2)cc1] | ¹H-NMR (CDCl₃) δ: 10.63 (1H, br s), 7.45 (1H, s), 7.43 (2H, d, J = 8.2 Hz), 6.91 (2H, d, J = 8.2 Hz), 4.54 (2H, s), 1.60 (9H, s), 1.50 (9H, s); [M + H]+ = 407. |
| 15 | 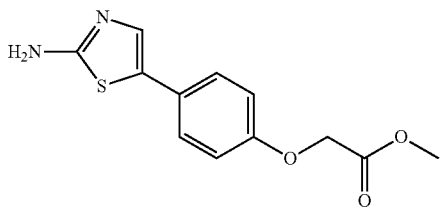 [SMILES: COC(=O)COc1ccc(-c2cnc(N)s2)cc1] | ¹H-NMR (CDCl₃) δ: 7.35 (2H, td, J = 6.0, 3.4 Hz), 7.19 (1H, s), 6.89 (2H, td, J = 6.0, 3.4 Hz), 4.86 (2H, br s), 4.65 (2H, s), 3.82 (3H, s); [M + H]+ = 265. |
| 16 | 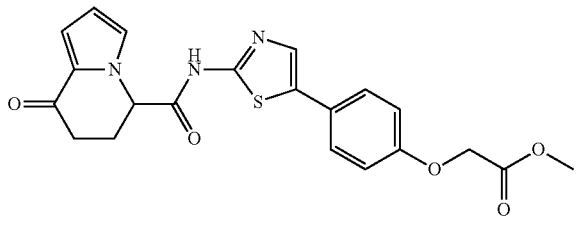 [SMILES: COC(=O)COc1ccc(-c2cnc(NC(=O)C3CCC(=O)c4cccn43)s2)cc1] | ¹H-NMR (CDCl₃) δ: 8.75 (1H, br s), 7.76-7.44 (3H, m), 7.19 (1H, dd, J = 3.9, 1.5 Hz), 6.99 (1H, dd, J = 2.4, 1.5 Hz), 6.93 (2H, dt, J = 9.0, 2.4 Hz), 6.49 (1H, dd, J = 3.9, 2.4 Hz), 5.14 (1H, dd, J = 5.1, 3.2 Hz), 4.67 (2H, s), 3.82 (3H, s), 2.90-2.85 (1H, m), 2.69-2.56 (3H, m); [M + H]+ = 426. |
| 17 |  | ¹H-NMR (CDCl₃) δ: 7.03 (1H, d, J = 1.8 Hz), 6.88 (1H, d, J = 1.8 Hz), 4.90-4.89 (1H, m), 3.81 (3H, s), 2.62-2.55 (4H, m); [M + H]+ = 272. |
TABLE 1-3
| | | |
|---|---|---|
| 18 | 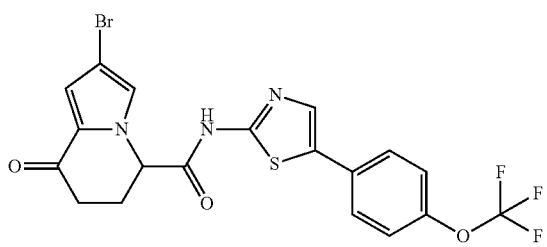 [SMILES: O=C1CCC(C(=O)Nc2ncc(-c3ccc(OC(F)(F)F)cc3)s2)n2cc(Br)cc21] | ¹H-NMR (DMSO-D₆) δ: 12.86 (1H, br s), 8.01-7.97 (1H, m), 7.75-7.71 (2H, m), 7.43-7.41 (3H, m), 6.91 (1H, d, J = 1.8 Hz), 5.36 (1H, t, J = 4.2 Hz), 2.65-2.50 (2H, m), 2.46-2.33 (2H, m); [M + H]+ = 500, 502. |

TABLE 1-3-continued

| | | |
|---|---|---|
| 19 | 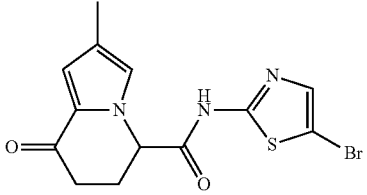 [SMILES: Cc1cc2n(c1)C(C(=O)Nc1ncc(Br)s1)CCC2=O] | ¹H-NMR (CDCl₃) δ: 8.40 (1H, br s), 7.35 (1H, s), 6.98 (1H, s), 6.75 (1H, s), 5.02 (1H, dd, J = 5.1, 2.7 Hz), 2.84-2.82 (1H, m), 2.65-2.54 (2H, m), 2.49-2.41 (1H, m), 2.17 (3H, s); [M + H]+ = 355. |
| 20 | 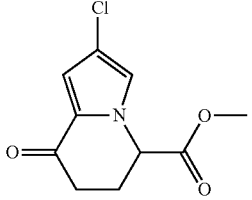 | ¹H-NMR (CDCl₃) δ: 6.94 (1H, d, J = 1.8 Hz), 6.83 (1H, d, J = 1.8 Hz), 4.87 (1H, dd, J = 4.2, 2.4 Hz), 3.81 (3H, s), 2.65-2.53 (4H, m); [M + H]+ = 228. |
| 21 | 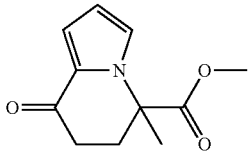 | 1295¹H-NMR (CDCl₃) δ: 7.09 (1H, dd, J = 3.9, 1.5 Hz), 7.04 (1H, t, J = 2.1 Hz), 6.35 (1H, dd, J = 3.9, 2.1 Hz), 3.73 (3H, s), 2.71-2.62 (1H, m), 2.60-2.48 (2H, m), 2.35-2.27 (1H, m), 1.89 (3H, s); [M + H]+ = 208. |
| 22 | 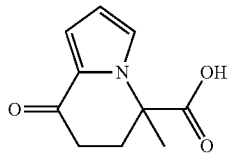 | ¹H-NMR (CDCl₃) δ: 7.10 (1H, d, J = 3.6 Hz), 7.06 (1H, d, J = 1.2 Hz), 6.36 (1H, t, J = 3.6 Hz), 2.72-2.60 (2H, m), 2.38-2.30 (2H, m), 1.93 (3H, s). |
| 23 | 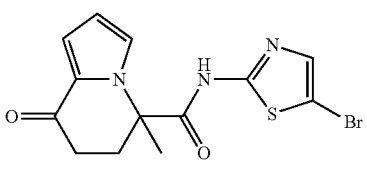 [SMILES: CC1(C(=O)Nc2ncc(Br)s2)CCC(=O)c2cccn21] | ¹H-NMR (CDCl₃) δ: 8.01 (1H, br s), 7.31 (1H, s), 7.21 (1H, dd, J = 3.9, 1.5 Hz), 7.12 (1H, dd, J = 2.7, 1.5 Hz), 6.53 (1H, dd, J = 3.9, 2.7 Hz), 2.89-2.84 (1H, m), 2.65 (1H, dt, J = 17.3, 3.2 Hz), 2.51-2.33 (2H, m), 1.98 (3H, s); [M + H]+ = 355. |
| 24 | 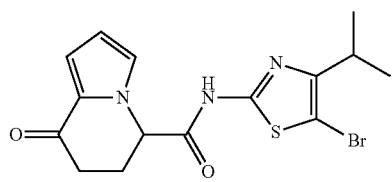 [SMILES: CC(C)c1nc(NC(=O)C2CCC(=O)c3cccn32)sc1Br] | ¹H-NMR (CDCl₃) δ: 8.36 (1H, br s), 7.21 (1H, dd, J = 4.2, 1.5 Hz), 6.99 (1H, dd, J = 2.4, 1.5 Hz), 6.52 (1H, dd, J = 4.2, 2.4 Hz), 5.11 (1H, dd, J = 4.8, 2.4 Hz), 3.18-3.08 (1H, m), 2.89-2.83 (1H, m), 2.69-2.48 (3H, m), 1.15 (6H, d, J = 7.3 Hz); [M + H]+ = 382. |
| 25 | 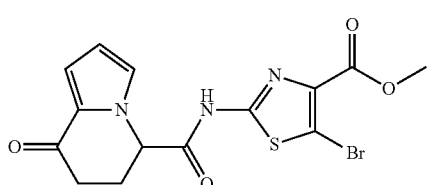 | ¹H-NMR (CDCl₃) δ: 7.17 (1H, dd, J = 4.2, 1.8 Hz), 6.95 (1H, t, J = 2.1 Hz), 6.48 (1H, dd, J = 4.2, 2.4 Hz), 5.15 (1H, dd, J = 5.1, 2.7 Hz), 3.92 (3H, s), 2.88-2.81 (1H, m), 2.68-2.57 (2H, m), 2.53-2.47 (1H, m); [M + H]+ = 398. |

TABLE 2-1

| Example No. | Structural formula | Physical and chemical data |
|---|---|---|
| 1 | | ¹H-NMR (CDCl₃) δ: 8.96 (1H, br s), 7.57 (1H, s), 7.55-7.52 (2H, m), 7.41-7.38 (2H, m), 7.33-7.32 (1H, m), 7.20 (1H, dd, J = 3.9, 1.6 Hz), 7.00 (1H, dd, J = 2.7, 1.6 Hz), 6.50 (1H, dd, J = 3.9, 2.7 Hz), 5.16 (1H, dd, J = 4.9, 3.3 Hz), 2.89-2.87 (1H, m), 2.71-2.53 (3H, m); [M + H]+ = 338. |
| 2 | | ¹H-NMR (DMSO-D₆) δ: 12.89 (1H, br s), 8.13 (1H, s), 7.97 (2H, d, J = 8.5 Hz), 7.76 (2H, d, J = 7.9 Hz), 7.24 (1H, t, J = 1.8 Hz), 6.86 (1H, dd, J = 4.3, 1.2 Hz), 6.28 (1H, dd, J = 3.7, 1.8 Hz), 5.38 (1H, t, J = 4.3 Hz), 3.85 (3H, s), 2.64-2.52 (2H, m), 2.45-2.42 (2H, m); [M + H]+ = 396. |
| 3 | | ¹H-NMR (CDCl₃) δ: 8.60 (1H, br s), 7.63 (1H, s), 7.56 (2H, dt, J = 8.5, 1.8 Hz), 7.46 (2H, dt, J = 8.5, 1.8 Hz), 7.20 (1H, dd, J = 3.9, 1.6 Hz), 7.00 (1H, dd, J = 2.5, 1.6 Hz), 6.51 (1H, dd, J = 3.9, 2.5 Hz), 5.16 (1H, dd, J = 4.9, 2.9 Hz), 3.13 (3H, br s), 3.02 (3H, br s), 2.92-2.87 (1H, m), 2.70-2.54 (3H, m); [M + H]+ = 409. |
| 4 | | ¹H-NMR (CDCl₃) δ: 7.44 (1H, s), 7.19 (1H, dd, J = 4.1, 1.4 Hz), 7.01-6.98 (3H, m), 6.83 (1H, dd, J = 5.9, 2.7 Hz), 6.49 (1H, dd, J = 4.1, 2.5 Hz), 6.00 (2H, s), 5.14 (1H, t, J = 4.1 Hz), 2.66-2.60 (4H, m); [M + H]+ = 382. |
| 5 | | ¹H-NMR (DMSO-D₆) δ: 12.91 (2H, br s), 8.10 (1H, s), 7.95 (2H, d, J = 7.9 Hz), 7.74 (2H, d, J = 7.9 Hz), 7.24 (1H, s), 6.87 (1H, d, J = 2.4 Hz), 6.29 (1H, s), 5.39 (1H, s), 2.58-2.44 (4H, m); [M + H]+ = 382. |
| 6 | | ¹H-NMR (DMSO-D₆) δ: 12.84 (1H, s), 8.07 (1H, s), 8.00 (1H, s), 7.90 (2H, d, J = 7.9 Hz), 7.69 (2H, d, J = 7.9 Hz), 7.40 (1H, s), 7.24 (1H, t, J = 2.1 Hz), 6.86 (1H, dd, J = 4.0, 1.5 Hz), 6.28 (1H, dd, J = 4.0, 2.1 Hz), 5.38 (1H, t, J = 4.3 Hz), 2.55-2.42 (4H, m); [M + H]+ = 381. |

TABLE 2-1-continued

| Example No. | Structural formula | Physical and chemical data |
|---|---|---|
| 7 | | $^1$H-NMR (DMSO-D$_6$) δ: 12.91 (1H, br s), 8.17 (1H, s), 7.86 (2H, d, J = 8.5 Hz), 7.80 (2H, d, J = 8.5 Hz), 7.23 (1H, dd, J = 2.4, 1.5 Hz), 6.86 (1H, dd, J = 4.2, 1.5 Hz), 6.28 (1H, dd, J = 4.2, 2.4 Hz), 5.37 (1H, t, J = 4.2 Hz), 2.61-2.53 (2H, m), 2.45-2.41 (2H, m).; [M + H]+ = 363. |

TABLE 2-2

| Example No. | Structural formula | Physical and chemical data |
|---|---|---|
| 8 | | $^1$H-NMR (CDCl$_3$) δ: 8.57 (1H, br s), 7.45 (1H, s), 7.45-7.42 (2H, m), 7.19 (1H, dd, J = 3.9, 1.5 Hz), 6.99 (1H, dd, J = 2.4, 1.5 Hz), 6.97-6.96 (2H, m), 6.50 (1H, dd, J = 3.9, 2.4 Hz), 5.14-5.13 (1H, m), 4.73 (2H, s), 3.10 (3H, s), 2.99 (3H, s), 2.89-2.87 (1H, m), 2.68-2.55 (3H, m); [M + H]+ = 439. |
| 9 | | $^1$H-NMR (DMSO-D$_6$) δ: 12.83 (1H, br s), 7.99 (1H, s), 7.73 (2H, d, J = 7.9 Hz), 7.42 (2H, d, J = 7.9 Hz), 7.23 (1H, t, J = 2.1 Hz), 6.86 (1H, dd, J = 3.9, 2.1 Hz), 6.28 (1H, dd, J = 3.9, 2.7 Hz), 5.37 (1H, t, J = 4.2 Hz), 2.63-2.50 (2H, m), 2.46-2.41 (2H, m); [M + H]+ = 422. |
| 10a First peak: Optically active form of compound of Example 9 | | HPLC measurement conditions Column: YMC CHIRAL ART Cellulose-SB (5um), 250 × 4.6 mm I.D., Column temperature: 25° C., Flow rate: 0.5 ml/min, Mobile phase: n-hexane/ethanol = 70/30, Measurement wavelength: 293 nm Retention time: tR = 14.9 min |
| 10b Second peak: Optically active form of compound of Example 9 | | HPLC measurement conditions Column: YMC CHIRAL ART Cellulose-SB (5um), 250 × 4.6 mm I.D., Column temperature: 25° C., Flow rate: 0.5 ml/min, Mobile phase: n-hexane/ethanol = 70/30, Measurement wavelength: 293 nm Retention time: tR = 21.6 min |
| 11 | | $^1$H-NMR (DMSO-D$_6$) δ: 12.73 (1H, br s), 7.83 (1H, s), 7.51 (2H, d, J = 8.5 Hz), 7.23 (1H, t, J = 2.1 Hz), 7.01 (2H, d, J = 8.5 Hz), 6.86 (1H, dd, J = 4.2, 1.8 Hz), 6.28 (1H, dd, J = 4.2, 2.1 Hz), 5.36 (1H, t, J = 4.2 Hz), 2.59-2.50 (2H, m), 2.45-2.44 (2H, m), 1.31 (9H, s); [M + H]+ = 410. |
| 12 | | $^1$H-NMR (DMSO-D$_6$) δ: 12.82 (1H, br s), 7.98 (1H, s), 7.63 (2H, d, J = 8.5 Hz), 7.47 (2H, d, J = 8.5 Hz), 7.23 (1H, s), 6.86 (1H, dd, J = 3.9, 1.5 Hz), 6.28 (1H, dd, J = 3.9, 2.1 Hz), 5.37 (1H, t, J = 3.9 Hz), 2.61-2.50 (2H, m), 2.45-2.41 (2H, m); [M + H]+ = 372. |

TABLE 2-3

| | | |
|---|---|---|
| 13 | (structure) | ¹H-NMR (DMSO-D$_6$) δ: 12.84 (1H, br s), 8.05 (1H, s), 7.73 (1H, s), 7.53 (1H, d, J = 7.9 Hz), 7.44 (1H, t, J = 7.9 Hz), 7.36 (1H, d, J = 7.9 Hz), 7.23 (1H, t, J = 2.2 Hz), 6.86 (1H, dd, J = 4.2, 1.2 Hz), 6.28 (1H, dd, J = 4.2, 2.2 Hz), 5.38 (1H, t, J = 4.2 Hz), 2.61-2.50 (2H, m), 2.46-2.41 (2H, m); [M + H]+ = 372. |
| 14 | (structure) | ¹H-NMR (CDCl$_3$) δ: 8.95 (1H, br s), 7.62 (1H, s), 7.50-7.48 (2H, m), 7.31-7.29 (2H, m), 7.20 (1H, dd, J = 3.9, 1.5 Hz), 6.99 (1H, dd, J = 2.7, 1.5 Hz), 6.50 (1H, dd, J = 3.9, 2.7 Hz), 5.16 (1H, t, J = 3.9 Hz), 2.91-2.86 (1H, m), 2.71-2.57 (3H, m); [M + H]+ = 372. |
| 15 | (structure) | ¹H-NMR (DMSO-D$_6$) δ: 12.83 (1H, s), 8.04 (1H, s), 7.54-7.51 (1H, m), 7.48-7.39 (2H, m), 7.23 (1H, t, J = 1.8 Hz), 7.17-7.11 (1H, m), 6.86 (1H, dd, J = 3.9, 1.5 Hz), 6.28 (1H, dd, J = 3.9, 1.8 Hz), 5.38 (1H, t, J = 4.2 Hz), 2.62-2.50 (2H, m), 2.45-2.41 (2H, m); [M + H]+ = 356. |
| 16 | (structure) | ¹H-NMR (DMSO-D$_6$) δ: 12.78 (1H, br s), 7.90 (1H, s), 7.67-7.62 (2H, m), 7.29-7.23 (3H, m), 6.86 (1H, dd, J = 3.9, 1.5 Hz), 6.28 (1H, dd, J = 3.9, 2.7 Hz), 5.37 (1H, t, J = 4.2 Hz), 2.62-2.50 (2H, m), 2.45-2.42 (2H, m); [M + H]+ = 356. |
| 17 | (structure) | ¹H-NMR (DMSO-D$_6$) δ: 12.84 (1H, s), 8.01 (1H, s), 7.78 (1H, td, J = 7.9, 1.2 Hz), 7.38-7.26 (3H, m), 7.24 (1H, t, J = 2.1 Hz), 6.86 (1H, dd, J = 3.9, 1.8 Hz), 6.28 (1H, dd, J = 3.9, 2.1 Hz), 5.38 (1H, t, J = 3.9 Hz), 2.58-2.53 (2H, m), 2.45-2.42 (2H, m); [M + H]+ = 356. |
| 18 | (structure) | ¹H-NMR (DMSO-D$_6$) δ: 12.73 (1H, br s), 7.87 (1H, s), 7.48 (2H, d, J = 7.9 Hz), 7.22 (3H, d, J = 7.9 Hz), 6.86 (1H, dd, J = 3.6, 1.2 Hz), 6.28 (1H, dd, J = 3.9, 2.7 Hz), 5.36 (1H, t, J = 4.2 Hz), 2.61-2.50 (2H, m), 2.45-2.42 (2H, m), 2.31 (3H, s); [M + H]+ = 352. |
| 19 | (structure) | ¹H-NMR (CDCl$_3$) δ: 9.38 (1H, br s), 7.36-7.21 (5H, m), 7.19 (1H, dd, J = 3.9, 0.9 Hz), 6.99 (1H, br s), 6.49 (1H, t, J = 3.0 Hz), 5.16 (1H, t, J = 3.9 Hz), 2.89-2.84 (1H, m), 2.71-2.59 (3H, m), 2.41 (3H, s); [M + H]+ = 352. |

TABLE 2-4

| | | |
|---|---|---|
| 20 | (structure) | ¹H-NMR (DMSO-D₆) δ: 12.76 (1H, br s), 7.91 (1H, s), 7.43 (1H, br s), 7.39 (1H, d, J = 7.8 Hz), 7.30 (1H, t, J = 7.8 Hz), 7.23 (1H, dd, J = 2.3, 1.6 Hz), 7.12 (1H, d, J = 7.8 Hz), 6.86 (1H, dd, J = 3.9, 1.6 Hz), 6.28 (1H, dd, J = 3.9, 2.3 Hz), 5.37 (1H, t, J = 4.3 Hz), 2.59-2.49 (2H, m), 2.47-2.41 (2H, m), 2.33 (3H, s); [M + H]+ = 352. |
| 21 | (structure) | ¹H-NMR (DMSO-D₆) δ: 12.89 (1H, br s), 8.11 (1H, s), 7.82 (2H, d, J = 8.4 Hz), 7.75 (2H, d, J = 8.4 Hz), 7.22 (1H, t, J = 2.3 Hz), 6.86 (1H, dd, J = 3.8, 1.5 Hz), 6.28 (1H, dd, J = 3.8, 2.3 Hz), 5.36 (1H, t, J = 4.2 Hz), 2.56-2.52 (2H, m), 2.45-2.43 (2H, m); [M + H]+ = 406. |
| 22 | (structure) | ¹H-NMR (DMSO-D₆) δ: 12.79 (1H, br s), 7.94 (1H, s), 7.62 (2H, d, J = 8.4 Hz), 7.51 (2H, d, J = 8.4 Hz), 7.37-7.31 (2H, m), 7.22 (1H, t, J = 2.3 Hz), 7.12 (1H, d, J = 7.6 Hz), 7.05-7.02 (1H, m), 6.86 (1H, dd, J = 3.8, 1.5 Hz), 6.28 (1H, dd, J = 3.8, 2.3 Hz), 5.34 (1H, t, J = 4.2 Hz), 3.78 (3H, s), 2.57-2.50 (2H, m), 2.46-2.44 (2H, m); [M + H]+ = 444. |
| 23 | (structure) | ¹H-NMR (DMSO-D₆) δ: 12.80 (1H, br s), 7.97 (1H, s), 7.70-7.66 (4H, m), 7.59 (2H, d, J = 8.4 Hz), 7.28 (2H, d, J = 8.4 Hz), 7.23 (1H, t, J = 2.3 Hz), 6.86 (1H, dd, J = 3.8, 1.5 Hz), 6.28 (1H, dd, J = 3.8 Hz), 5.36 (1H, t, J = 4.2 Hz), 2.59-2.50 (2H, m), 2.47-2.42 (2H, m), 2.34 (3H, s); [M + H]+ = 428. |
| 24 | (structure) | ¹H-NMR (DMSO-D₆) δ: 12.80 (1H, s), 8.08-8.06 (2H, m), 7.96-7.89 (3H, m), 7.83 (1H, dd, J = 8.4, 2.3 Hz), 7.52-7.50 (2H, m), 7.23 (1H, t, J = 1.9 Hz), 6.87 (1H, dd, J = 3.8, 1.5 Hz), 6.28 (1H, dd, J = 3.8, 1.9 Hz), 5.35 (1H, t, J = 4.2 Hz), 2.60-2.45 (4H, m); [M + H]+ = 388. |
| 25 | (structure) | ¹H-NMR (DMSO-D₆) δ: 12.86 (1H, br s), 8.06 (1H, s), 7.62-7.60 (2H, m), 7.54 (1H, t, J = 8.0 Hz), 7.29 (1H, dd, J = 9.2, 1.5 Hz), 7.22 (1H, t, J = 2.3 Hz), 6.86 (1H, dd, J = 3.8, 1.5 Hz), 6.28 (1H, dd, J = 3.8, 2.3 Hz), 5.36 (1H, t, J = 4.2 Hz), 2.58-2.50 (2H, m), 2.45-2.42 (2H, m); [M + H]+ = 422. |

TABLE 2-5

| # | Structure | NMR |
|---|---|---|
| 26 | 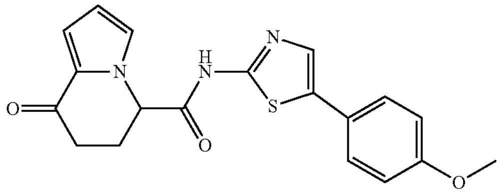 [SMILES: COc1ccc(-c2cnc(NC(=O)C3CCC(=O)c4cccn43)s2)cc1] | ¹H-NMR (DMSO-D₆) δ: 12.70 (1H, br s), 7.79 (1H, s), 7.53-7.52 (2H, m), 7.22 (1H, t, J = 2.1 Hz), 7.00-6.96 (2H, m), 6.86 (1H, dd, J = 3.9, 1.5 Hz), 6.28 (1H, dd, J = 3.9, 2.1 Hz), 5.35 (1H, t, J = 4.2 Hz), 3.77 (3H, s), 2.59-2.53 (2H, m), 2.45-2.41 (2H, m); [M + H]+ = 368. |
| 27 | 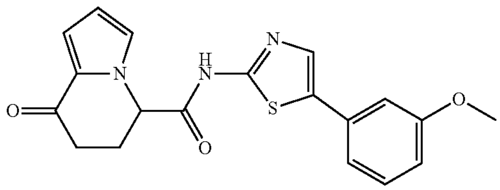 [SMILES: COc1cccc(-c2cnc(NC(=O)C3CCC(=O)c4cccn43)s2)c1] | ¹H-NMR (DMSO-D₆) δ: 12.78 (1H, br s), 7.96 (1H, s), 7.32 (1H, t, J = 8.0 Hz), 7.23 (1H, t, J = 1.9 Hz), 7.17-7.14 (2H, m), 6.89-6.87 (1H, m), 6.86 (1H, dd, J = 3.8, 1.5 Hz), 6.28 (1H, dd, J = 3.8, 2.4 Hz), 5.36 (1H, t, J = 4.2 Hz), 3.80 (3H, s), 2.59-2.50 (2H, m), 2.46-2.42 (2H, m); [M + H]+ = 368. |
| 28 | 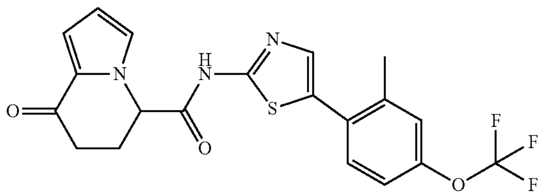 [SMILES: Cc1cc(OC(F)(F)F)ccc1-c1cnc(NC(=O)C2CCC(=O)c3cccn32)s1] | ¹H-NMR (DMSO-D₆) δ: 12.81 (1H, br s), 7.62 (1H, s), 7.49 (1H, d, J = 8.4 Hz), 7.36 (1H, s), 7.25 (1H, d, J = 8.4 Hz), 7.22 (1H, t, J = 1.9 Hz), 6.85 (1H, dd, J = 3.8, 1.5 Hz), 6.27 (1H, dd, J = 3.8, 1.9 Hz), 5.36 (1H, t, J = 4.6 Hz), 2.58-2.50 (2H, m), 2.45-2.43 (2H, m), 2.41 (3H, s); [M + H]+ = 436. |
| 29 | 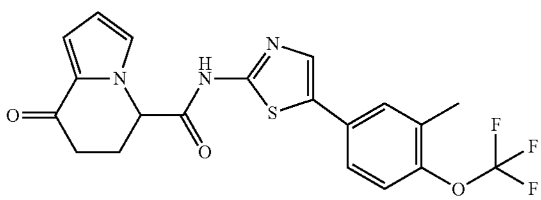 [SMILES: Cc1cc(-c2cnc(NC(=O)C3CCC(=O)c4cccn43)s2)ccc1OC(F)(F)F] | ¹H-NMR (DMSO-D₆) δ: 12.81 (1H, br s), 7.95 (1H, s), 7.66 (1H, d, J = 1.8 Hz), 7.54 (1H, dd, J = 8.5, 1.8 Hz), 7.36-7.34 (1H, m), 7.23 (1H, t, J = 2.7 Hz), 6.86 (1H, dd, J = 4.0, 2.0 Hz), 6.28 (1H, dd, J = 4.0, 2.7 Hz), 5.36 (1H, t, J = 4.3 Hz), 2.61-2.48 (2H, m), 2.47-2.42 (2H, m), 2.30 (3H, s); [M + H]+ = 436. |
| 30 | 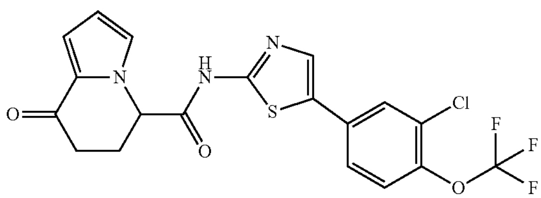 [SMILES: O=C1CCC(C(=O)Nc2ncc(-c3ccc(OC(F)(F)F)c(Cl)c3)s2)n2cccc21] | ¹H-NMR (DMSO-D₆) δ: 12.88 (1H, br s), 8.07 (1H, s), 7.99 (1H, d, J = 2.3 Hz), 7.64 (1H, dd, J = 8.4, 2.3 Hz), 7.59 (1H, dd, J = 8.4, 1.5 Hz), 7.22 (1H, t, J = 2.3 Hz), 6.86 (1H, dd, J = 3.8, 1.5 Hz), 6.28 (1H, dd, J = 3.8, 2.3 Hz), 5.35 (1H, t, J = 4.2 Hz), 2.59-2.50 (2H, m), 2.46-2.42 (2H, m); [M + H]+ = 456. |
| 31 | 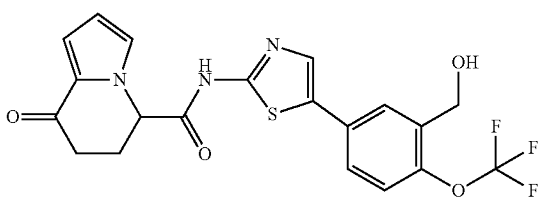 [SMILES: O=C1CCC(C(=O)Nc2ncc(-c3ccc(OC(F)(F)F)c(CO)c3)s2)n2cccc21] | ¹H-NMR (DMSO-D₆) δ: 12.83 (1H, br s), 7.94 (1H, s), 7.75 (1H, d, J = 2.3 Hz), 7.64 (1H, dd, J = 8.4, 2.3 Hz), 7.36 (1H, dd, J = 8.4, 1.5 Hz), 7.23 (1H, t, J = 2.3 Hz), 6.86 (1H, dd, J = 4.2, 1.5 Hz), 6.28 (1H, dd, J = 4.2, 2.3 Hz), 5.46 (1H, t, J = 5.4 Hz), 5.36 (1H, t, J = 4.2 Hz), 4.58 (2H, d, J = 5.4 Hz), 2.59-2.50 (2H, m), 2.46-2.43 (2H, m); [M + H]+ = 452. |

TABLE 2-6

| 32 | | ¹H-NMR (DMSO-D₆) δ: 12.71 (1H, br s), 7.78 (1H, s), 7.52 (2H, td, J = 6.1, 3.6 Hz), 7.45 (2H, d, J = 7.3 Hz), 7.39 (2H, t, J = 7.3 Hz), 7.33 (1H, tt, J = 7.3, 1.8 Hz), 7.22 (1H, t, J = 2.3 Hz), 7.06 (2H, td, J = 6.1, 3.6 Hz), 6.86 (1H, dd, J = 3.8, 1.5 Hz), 6.28 (1H, dd, J = 3.8, 2.3 Hz), 5.34 (1H, t, J = 4.2 Hz), 5.14 (2H, s), 2.59-2.50 (2H, m), 2.44-2.43 (2H, m); [M + H]+ = 444. |

TABLE 2-6-continued

| | | |
|---|---|---|
| 33 | (structure) | ¹H-NMR (DMSO-D₆) δ: 12.70 (1H, br s), 7.78 (1H, s), 7.49 (2H, d, J = 8.0 Hz), 7.23 (1H, s), 6.95 (2H, d, J = 8.0 Hz), 6.86 (1H, d, J = 3.0 Hz), 6.28 (1H, s), 5.36 (1H, s), 4.66-4.60 (1H, m), 2.49-2.46 (4H, m), 1.26 (6H, d, J = 6.0 Hz); [M + H]+ = 396. |
| 34 | (structure) | ¹H-NMR (DMSO-D₆) δ: 12.72 (1H, s), 7.45-7.45 (4H, m), 7.38-7.33 (1H, m), 7.22 (1H, t, J = 1.5 Hz), 6.85 (1H, dd, J = 4.0, 1.5 Hz), 6.28 (1H, dd, J = 4.0, 2.4 Hz), 5.34 (1H, t, J = 4.0 Hz), 2.56-2.52 (2H, m), 2.44-2.41 (2H, m), 2.37 (3H, s); [M + H]+ = 352. |
| 35 | (structure) | ¹H-NMR (DMSO-D₆) δ: 12.67 (1H, br s), 7.35 (2H, d, J = 8.5 Hz), 7.21 (1H, br s), 7.04 (2H, d, J = 8.5 Hz), 6.85 (1H, br s), 6.27 (1H, d, J = 3.6 Hz), 5.33 (1H, br s), 2.50-2.43 (4H, br m), 2.35 (3H, s), 1.32 (9H, s); [M + H]+ = 424. |
| 36 | (structure) | ¹H-NMR (DMSO-D₆) δ: 12.77 (1H, br s), 7.58 (2H, dt, J = 8.5, 1.8 Hz), 7.45 (2H, d, J = 8.5 Hz), 7.21 (1H, t, J = 1.8 Hz), 6.85 (1H, dd, J = 3.9, 1.8 Hz), 6.27 (1H, dd, J = 3.9, 2.4 Hz), 5.35 (1H, t, J = 3.9 Hz), 2.58-2.48 (2H, m), 2.45-2.41 (2H, m), 2.38 (3H, s); [M + H]+ = 436. |
| 37 | (structure) | ¹H-NMR (DMSO-D₆) δ: 12.74 (1H, br s), 7.88 (1H, s), 7.55 (2H, t, J = 4.2 Hz), 7.34 (2H, d, J = 8.4 Hz), 7.22 (1H, t, J = 1.9 Hz), 6.85 (1H, dd, J = 3.8, 1.5 Hz), 6.27 (1H, dd, J = 3.8, 1.9 Hz), 5.34 (1H, t, J = 4.6 Hz), 5.21 (1H, t, J = 5.4 Hz), 4.49 (2H, d, J = 4.6 Hz), 2.56-2.49 (2H, m), 2.45-2.43 (2H, m); [M + H]+ = 368. |
| 38 | (structure) | ¹H-NMR (DMSO-D₆) δ: 7.74 (1H, s), 7.49 (2H, dt, J = 8.4, 1.5 Hz), 7.20 (1H, t, J = 2.3 Hz), 6.98 (2H, dt, J = 8.4, 1.5 Hz), 6.84 (1H, dd, J = 3.8, 1.5 Hz), 6.26 (1H, dd, J = 3.8, 2.3 Hz), 5.29 (1H, t, J = 4.2 Hz), 4.11-4.09 (2H, m), 3.66-3.65 (2H, m), 3.30 (3H, s), 2.54-2.49 (2H, m), 2.45-2.43 (2H, m); [M + H]+ = 412. |

TABLE 2-7

| | | |
|---|---|---|
| 39 | (structure) | ¹H-NMR (DMSO-D₆) δ: 12.79 (1H, br s), 7.91 (1H, s), 7.65 (2H, dd, J = 8.4, 2.3 Hz), 7.26 (1H, t, J = 74.2 Hz), 7.23-7.21 (3H, m), 6.86 (1H, dd, J = 3.8, 1.5 Hz), 6.28 (1H, dd, J = 3.8, 2.3 Hz), 5.35 (1H, t, J = 4.6 Hz), 2.58-2.49 (2H, m), 2.45-2.42 (2H, m); [M + H]+ = 404. |

TABLE 2-7-continued

| 40 | (structure) | ¹H-NMR (DMSO-D₆) δ: 12.82 (1H, br s), 7.94 (1H, s), 7.77 (1H, d, J = 1.5 Hz), 7.45 (1H, d, J = 8.4 Hz), 7.39 (1H, dd, J = 8.4, 1.5 Hz), 7.22 (1H, t, J = 2.7 Hz), 6.86 (1H, dd, J = 4.2, 1.5 Hz), 6.28 (1H, dd, J = 4.2, 2.7 Hz), 5.36 (1H, t, J = 4.2 Hz), 2.60-2.50 (2H, m), 2.45-2.42 (2H, m); [M + H]+ = 418. |
| --- | --- | --- |
| 41 | (structure) | ¹H-NMR (DMSO-D₆) δ: 12.67 (1H, br s), 7.75 (1H, s), 7.45 (2H, d, J = 9.1 Hz), 7.22 (1H, t, J = 2.1 Hz), 6.98 (2H, d, J = 9.1 Hz), 6.86 (1H, dd, J = 3.9, 1.5 Hz), 6.28 (1H, dd, J = 3.9, 2.1 Hz), 5.35 (1H, t, J = 4.2 Hz), 3.73 (4H, t, J = 4.8 Hz), 3.13 (4H, t, J = 4.8 Hz), 2.60-2.50 (2H, m), 2.46-2.41 (2H, m); [M + H]+ = 423. |
| 42 | (structure) | ¹H-NMR (DMSO-D₆) δ: 12.91 (1H, br s), 8.16 (1H, s), 7.87 (2H, dd, J = 8.4, 2.3 Hz), 7.76 (2H, d, J = 8.4 Hz), 7.24 (1H, t, J = 1.9 Hz), 6.87 (1H, dd, J = 4.2, 1.5 Hz), 6.29 (1H, dd, J = 4.2, 1.9 Hz), 5.39 (1H, t, J = 4.2 Hz), 2.63 (6H, s), 2.61-2.54 (2H, m), 2.47-2.42 (2H, m); [M + H]+ = 445. |
| 43 | (structure) | ¹H-NMR (DMSO-D₆) δ: 12.76 (1H, br s), 7.88 (1H, s), 7.59-7.56 (1H, m), 7.46 (2H, d, J = 7.9 Hz), 7.41 (2H, t, J = 7.9 Hz), 7.37-7.26 (3H, m), 7.22 (1H, t, J = 1.8 Hz), 6.86 (1H, dd, J = 4.2, 1.8 Hz), 6.28 (1H, dd, J = 4.2, 2.4 Hz), 5.36 (1H, t, J = 3.9 Hz), 5.21 (2H, s), 2.59-2.50 (2H, m), 2.45-2.41 (2H, m); [M + H]+ = 462. |
| 44 | (structure) | ¹H-NMR (DMSO-D₆) δ: 12.76 (1H, br s), 7.85 (1H, s), 7.66 (1H, t, J = 8.5 Hz), 7.47-7.32 (5H, m), 7.22 (1H, t, J = 1.8 Hz), 7.07 (1H, dd, J = 12.8, 2.4 Hz), 6.94 (1H, dd, J = 8.5, 2.4 Hz), 6.86 (1H, dd, J = 4.3, 1.5 Hz), 6.28 (1H, dd, J = 4.3, 1.8 Hz), 5.37 (1H, t, J = 4.3 Hz), 5.16 (2H, s), 2.60-2.52 (2H, m), 2.46-2.41 (2H, m); [M + H]+ = 462. |

TABLE 2-8

| 45 |  | ¹H-NMR (DMSO-D₆) δ: 12.73 (1H, br s), 7.85 (1H, s), 7.57 (2H, d, J = 8.5 Hz), 7.23 (1H, t, J = 2.1 Hz), 7.11 (2H, d, J = 8.5 Hz), 6.86 (1H, dd, J = 3.6, 1.2 Hz), 6.28 (1H, dd, J = 3.6, 2.1 Hz), 5.36 (1H, t, J = 3.9 Hz), 4.80 (2H, q, J = 8.9 Hz), 2.59-2.53 (2H, m), 2.45-2.42 (2H, m); [M + H]+ = 436. |
| --- | --- | --- |

TABLE 2-8-continued

| # | Structure | Data |
|---|---|---|
| 46 | (structure) | ¹H-NMR (DMSO-D₆) δ: 12.76 (1H, br s), 7.86 (1H, s), 7.61 (2H, d, J = 8.5 Hz), 7.41 (2H, t, J = 7.9 Hz), 7.23 (1H, t, J = 2.1 Hz), 7.17 (1H, t, J = 7.9 Hz), 7.07-7.03 (4H, m), 6.86 (1H, dd, J = 4.2, 1.5 Hz), 6.28 (1H, dd, J = 4.2, 2.1 Hz), 5.36 (1H, t, J = 4.2 Hz), 2.59-2.50 (2H, m), 2.45-2.42 (2H, m); [M − H]− = 428. |
| 47 | (structure) | ¹H-NMR (DMSO-D₆) δ: 12.82 (1H, br s), 7.99 (1H, s), 7.61 (2H, d, J = 8.5 Hz), 7.56 (2H, d, J = 8.5 Hz), 7.23 (1H, t, J = 2.1 Hz), 6.86 (1H, dd, J = 3.9, 1.5 Hz), 6.28 (1H, dd, J = 3.9, 2.1 Hz), 5.37 (1H, t, J = 3.9 Hz), 2.60-2.50 (2H, m), 2.45-2.41 (2H, m); [M + H]+ = 416. |
| 48 | (structure) | ¹H-NMR (DMSO-D₆) δ: 7.89 (1H, s), 7.64-7.60 (2H, m), 7.25-7.20 (3H, m), 6.85 (1H, dd, J = 4.0, 1.5 Hz), 6.27 (1H, dd, J = 4.0, 2.4 Hz), 5.31 (1H, t, J = 4.3 Hz), 2.55-2.50 (2H, m), 2.46-2.42 (2H, m), 1.49 (9H, s); [M + H]+ = 454. |
| 49 | (structure) | ¹H-NMR (DMSO-D₆) δ: 12.69 (1H, br s), 7.77 (1H, s), 7.52-7.48 (2H, m), 7.22 (1H, dd, J = 2.4, 1.5 Hz), 6.99-6.95 (2H, m), 6.85 (1H, dd, J = 4.0, 1.5 Hz), 6.27 (1H, dd, J = 4.0, 2.4 Hz), 5.34 (1H, t, J = 4.0 Hz), 3.76 (2H, d, J = 6.7 Hz), 2.58-2.50 (2H, m), 2.45-2.42 (2H, m), 2.06-1.96 (1H, m), 0.97 (6H, d, J = 6.7 Hz); [M + H]+ = 410. |
| 50 | (structure) | ¹H-NMR (CDCl₃) δ: 8.77 (1H, s), 7.18-7.17 (2H, m), 6.97 (1H, dd, J = 2.7, 1.5 Hz), 6.48 (1H, dd, J = 3.9, 2.7 Hz), 6.09 (1H, t, J = 3.9 Hz), 5.11 (1H, t, J = 4.2 Hz), 2.88-2.83 (1H, m), 2.67-2.53 (3H, m), 2.38-2.32 (2H, m), 2.21-2.16 (2H, m), 1.79-1.73 (2H, m), 1.68-1.62 (2H, m); [M + H]+ = 342. |
| 51 | (structure) | ¹H-NMR (DMSO-D₆) δ: 12.67 (1H, br s), 7.45 (1H, s), 7.20 (1H, dd, J = 2.4, 1.2 Hz), 6.84 (1H, dd, J = 4.0, 1.5 Hz), 6.26 (1H, dd, J = 4.0, 2.4 Hz), 5.92 (1H, br s), 5.30 (1H, t, J = 4.0 Hz), 3.95 (2H, br s), 3.51 (2H, t, J = 5.5 Hz), 2.58-2.49 (2H, m), 2.46-2.39 (4H, m), 1.41 (9H, s); [M − H]− = 441. |

TABLE 2-9

| # | Structure | Data |
|---|---|---|
| 52 | (structure) | ¹H-NMR (DMSO-D₆) δ: 12.83 (1H, br s), 8.29 (1H, d, J = 2.4 Hz), 8.22 (1H, d, J = 2.4 Hz), 7.95 (1H, s), 7.21 (1H, t, J = 1.8 Hz), 6.85 (1H, dd, J = 4.0, 1.5 Hz), 6.27 (1H, dd, J = 4.0, 1.8 Hz), 5.34 (1H, t, J = 4.3 Hz), 4.14 (2H, d, J = 6.7 Hz), 2.58-2.53 (2H, m), 2.45-2.41 (2H, m), 2.11-2.01 (1H, m), 0.98 (6H, d, J = 6.7 Hz); [M + H]+ = 445. |

TABLE 2-9-continued

| | Structure | NMR / MS |
|---|---|---|
| 53 | 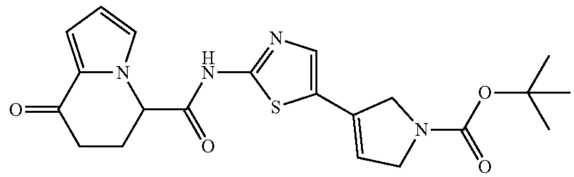 [SMILES: CC(C)(C)OC(=O)N1CC=C(c2cnc(NC(=O)C3CCC(=O)c4cccn43)s2)C1] | ¹H-NMR (DMSO-D₆) δ: 12.79 (1H, br s), 7.48 (1H, s), 7.21 (1H, s), 6.85 (1H, dd, J = 4.0, 1.5 Hz), 6.27 (1H, dd, J = 4.0, 2.4 Hz), 5.98 (1H, d, J = 17.1 Hz), 5.33 (1H, t, J = 3.7 Hz), 4.38-4.33 (2H, br m), 4.17-4.12 (2H, br m), 2.57-2.50 (2H, m), 2.43-2.39 (2H, m), 1.44 (9H, d, J = 6.1 Hz); [M + H]+ = 429. |
| 54 | 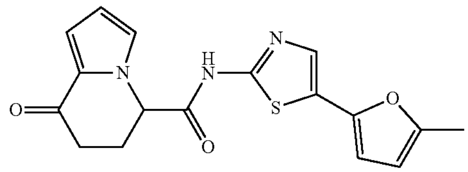 [SMILES: Cc1ccc(-c2cnc(NC(=O)C3CCC(=O)c4cccn43)s2)o1] | ¹H-NMR (DMSO-D₆) δ: 12.78 (1H, br s), 7.67 (1H, s), 7.22 (1H, dd, J = 2.4, 1.2 Hz), 6.86 (1H, dd, J = 4.0, 1.2 Hz), 6.58 (1H, d, J = 3.1 Hz), 6.28 (1H, dd, J = 4.0, 2.4 Hz), 6.18 (1H, dd, J = 3.1, 1.2 Hz), 5.35 (1H, t, J = 4.3 Hz), 2.62-2.50 (2H, m), 2.46-2.41 (2H, m), 2.30 (3H, s); [M + H]+ = 342. |
| 55 | 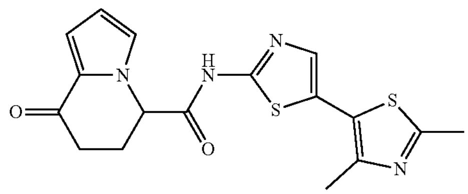 [SMILES: Cc1nc(C)c(-c2cnc(NC(=O)C3CCC(=O)c4cccn43)s2)s1] | ¹H-NMR (DMSO-D₆) δ: 12.86 (1H, br s), 7.59 (1H, s), 7.20 (1H, dd, J = 2.4, 1.2 Hz), 6.85 (1H, dd, J = 4.0, 1.2 Hz), 6.27 (1H, dd, J = 4.0, 2.4 Hz), 5.33 (1H, t, J = 4.3 Hz), 2.60 (3H, s), 2.56-2.50 (2H, m), 2.45-2.41 (2H, m), 2.40 (3H, s); [M + H]+ = 373. |
| 56 | 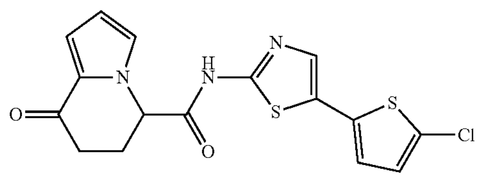 [SMILES: O=C1CCC(C(=O)Nc2ncc(-c3ccc(Cl)s3)s2)n2cccc21] | ¹H-NMR (DMSO-D₆) δ: 7.69 (1H, s), 7.19 (1H, t, J = 1.5 Hz), 7.10 (2H, d, J = 4.0 Hz), 6.84 (1H, dd, J = 4.0, 1.5 Hz), 6.26 (1H, dd, J = 4.3, 2.4 Hz), 5.29 (1H, t, J = 4.0 Hz), 2.55-2.50 (2H, m), 2.44-2.40 (2H, m); [M + H]+ = 378. |
| 57 | 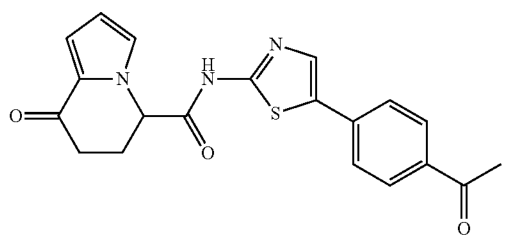 [SMILES: CC(=O)c1ccc(-c2cnc(NC(=O)C3CCC(=O)c4cccn43)s2)cc1] | ¹H-NMR (DMSO-D₆) δ: 12.89 (1H, br s), 8.13 (1H, s), 7.98 (2H, dt, J = 8.7, 2.0 Hz), 7.75 (2H, dt, J = 8.7, 2.0 Hz), 7.23 (1H, t, J = 2.1 Hz), 6.86 (1H, dd, J = 4.0, 1.5 Hz), 6.28 (1H, dd, J = 4.0, 2.1 Hz), 5.38 (1H, t, J = 4.3 Hz), 2.58 (3H, s), 2.56-2.52 (2H, m), 2.45-2.42 (2H, m); [M + H]+ = 380. |
| 58 | 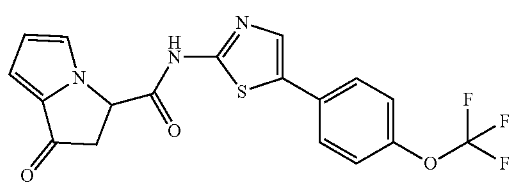 [SMILES: O=C1CC(C(=O)Nc2ncc(-c3ccc(OC(F)(F)F)cc3)s2)n2cccc21] | ¹H-NMR (DMSO-D₆) δ: 12.91 (1H, br s), 8.00 (1H, s), 7.74 (2H, d, J = 8.5 Hz), 7.42 (2H, d, J = 8.5 Hz), 7.39 (1H, d, J = 1.8 Hz), 6.67 (1H, d, J = 4.2 Hz), 6.54 (1H, dd, J = 4.2, 1.8 Hz), 5.50 (1H, dd, J = 8.5, 3.0 Hz), 3.44 (1H, dd, J = 18.1, 8.5 Hz), 3.09 (1H, dd, J = 18.1, 3.0 Hz); [M + H]+ = 408. |

TABLE 2-10

| | Structure | NMR / MS |
|---|---|---|
| 59 | 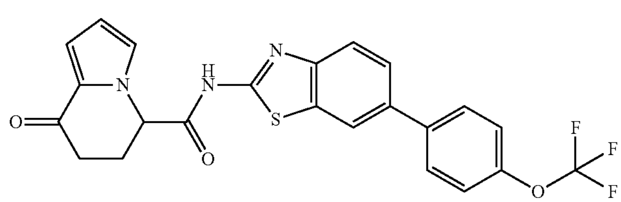 [SMILES: O=C1CCC(C(=O)Nc2nc3ccc(-c4ccc(OC(F)(F)F)cc4)cc3s2)n2cccc21] | ¹H-NMR (DMSO-D₆) δ: 13.00 (1H, br s), 8.37 (1H, d, J = 1.8 Hz), 7.89-7.84 (3H, m), 7.78 (1H, dd, J = 8.5, 1.8 Hz), 7.47 (2H, d, J = 8.5 Hz), 7.28 (1H, t, J = 2.1 Hz), 6.88 (1H, dd, J = 3.8, 1.5 Hz), 6.30 (1H, dd, J = 3.8, 2.1 Hz), 5.43 (1H, t, J = 4.2 Hz), 2.66-2.56 (2H, m), 2.47-2.38 (2H, m); [M + H]+ = 472. |

TABLE 2-10-continued

| 60 | 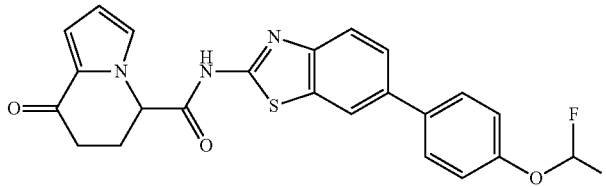 | ¹H-NMR (DMSO-D₆) δ: 12.97 (1H, br s), 8.33 (1H, d, J = 1.5 Hz), 7.85 (1H, d, J = 8.4 Hz), 7.80-7.76 (3H, m), 7.38 (1H, t, J = 74.9 Hz), 7.28-7.28 (3H, m), 6.88 (1H, dd, J = 3.8, 1.5 Hz), 6.30 (1H, dd, J = 3.8, 2.3 Hz), 5.43 (1H, t, J = 4.2 Hz), 2.64-2.56 (2H, m), 2.44-2.42 (2H, m); [M + H]+ = 454. |
| --- | --- | --- |
| 61 | 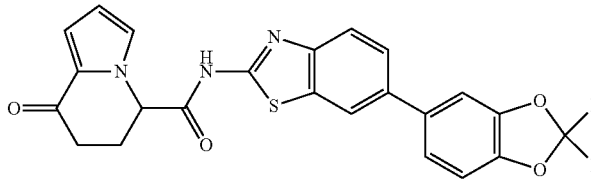 | ¹H-NMR (DMSO-D₆) δ: 12.99 (1H, br s), 8.33 (1H, d, J = 1.5 Hz), 7.84 (1H, d, J = 8.4 Hz), 7.82 (1H, d, J = 1.5 Hz), 7.76 (1H, dd, J = 8.4, 1.9 Hz), 7.58 (1H, dd, J = 8.4, 1.5 Hz), 7.51 (1H, d, J = 8.4 Hz), 7.27 (1H, t, J = 1.9 Hz), 6.87 (1H, dd, J = 3.8, 1.9 Hz), 6.29 (1H, dd, J = 3.8, 2.7 Hz), 5.42 (1H, t, J = 4.2 Hz), 2.62-2.56 (2H, m), 2.47-2.40 (2H, m); [M + H]+ = 468. |
| 62 | 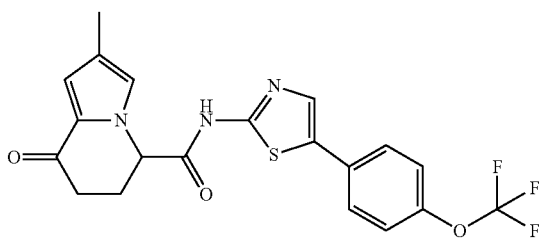 [SMILES: Cc1cc2n(c1)C(C(=O)Nc1ncc(-c3ccc(OC(F)(F)F)cc3)s1)CCC2=O] | ¹H-NMR (CDCl₃) δ: 8.64 (1H, br s), 7.56-7.54 (3H, m), 7.25 (2H, d, J = 8.5 Hz), 6.99 (1H, s), 6.77 (1H, s), 5.06-5.05 (1H, m), 2.87-2.84 (1H, m), 2.66-2.46 (3H, m), 2.17 (3H, s); [M + H]+ = 436. |
| 63 | 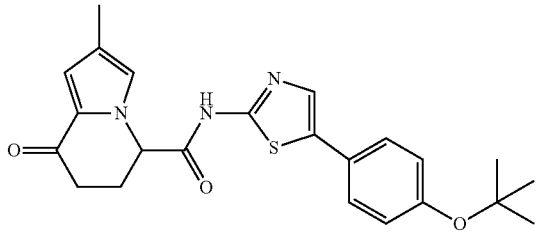 [SMILES: Cc1cc2n(c1)C(C(=O)Nc1ncc(-c3ccc(OC(C)(C)C)cc3)s1)CCC2=O] | ¹H-NMR (CDCl₃) δ: 8.72 (1H, br s), 7.50 (1H, s), 7.45-7.41 (2H, m), 7.03-7.00 (2H, m), 6.98 (1H, s), 6.77 (1H, s), 5.05 (1H, t, J = 3.9 Hz), 2.89-2.83 (1H, m), 2.65-2.50 (3H, m), 2.17 (3H, s), 1.37 (9H, s); [M + H]+ = 424. |
| 64 | 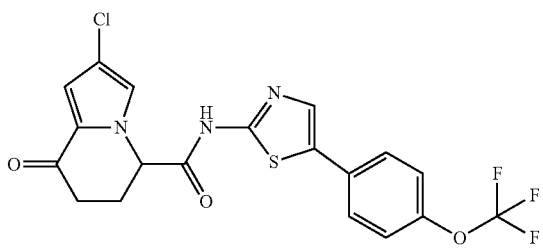 [SMILES: O=C1CCC(C(=O)Nc2ncc(-c3ccc(OC(F)(F)F)cc3)s2)n2cc(Cl)cc21] | ¹H-NMR (DMSO-D₆) δ: 12.86 (1H, br s), 7.99 (1H, s), 7.76-7.72 (2H, m), 7.43-7.41 (3H, m), 6.86 (1H, d, J = 1.8 Hz), 5.35 (1H, t, J = 3.9 Hz), 2.64-2.50 (2H, m), 2.47-2.35 (2H, m); |
| 65 | 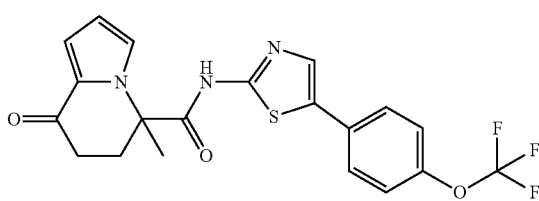 [SMILES: CC1(C(=O)Nc2ncc(-c3ccc(OC(F)(F)F)cc3)s2)CCC(=O)c2cccn21] | ¹H-NMR (CDCl₃) δ: 8.07 (1H, br s), 7.55 (1H, s), 7.54 (2H, d, J = 8.5 Hz), 7.26-7.24 (3H, m), 7.16 (1H, s), 6.56 (1H, t, J = 3.3 Hz), 2.90 (1H, dt, J = 13.5, 3.6 Hz), 2.68 (1H, dt, J = 17.5, 3.6 Hz), 2.54-2.48 (1H, m), 2.39 (1H, td, J = 13.5, 4.4 Hz), 2.01 (3H, s); [M + H]+ = 436. |

TABLE 2-11

| | | |
|---|---|---|
| 66 | | ¹H-NMR (DMSO-D₆) δ: 12.47 (1H, br s), 7.85 (1H, s), 7.47 (2H, d, J = 8.4 Hz), 7.33 (1H, t, J = 2.3 Hz), 7.22 (2H, d, J = 8.4 Hz), 6.87 (1H, dd, J = 3.8, 1.5 Hz), 6.31 (1H, dd, J = 3.8, 2.3 Hz), 2.83 (1H, d, J = 14.5 Hz), 2.50-2.39 (2H, m), 2.30 (3H, s), 2.28-2.21 (1H, m), 2.00 (3H, s); [M + H]+ = 366. |
| 67 | | ¹H-NMR (DMSO-D₆) δ: 12.49 (1H, br s), 7.89 (1H, s), 7.42 (1H, s), 7.38 (1H, d, J = 7.6 Hz), 7.33 (1H, s), 7.29 (1H, t, J = 7.6 Hz), 7.11 (1H, d, J = 7.6 Hz), 6.87 (1H, d, J = 3.4 Hz), 6.31 (1H, t, J = 3.4 Hz), 2.83 (1H, d, J = 14.5 Hz), 2.50-2.39 (2H, m), 2.32 (3H, s), 2.29-2.22 (1H, m), 2.01 (3H, s); [M + H]+ = 366. |
| 68 | | ¹H-NMR (DMSO-D₆) δ: 7.86 (1H, s), 7.70 (1H, d, J = 1.5 Hz), 7.41 (1H, d, J = 8.4 Hz), 7.33 (1H, dd, J = 8.4, 2.7 Hz), 7.30 (1H, t, J = 2.7 Hz), 6.84 (1H, dd, J = 3.8, 1.5 Hz), 6.28 (1H, t, J = 3.8 Hz), 2.50-2.42 (2H, m), 2.36-2.26 (2H, m), 1.95 (3H, s); [M + H]+ = 432. |
| 69 | | ¹H-NMR (DMSO-D₆) δ: 12.39 (1H, br s), 7.77 (1H, s), 7.49-7.46 (2H, m), 7.33 (1H, t, J = 1.5 Hz), 6.96-6.93 (2H, m), 6.87 (1H, dd, J = 4.2, 1.5 Hz), 6.31 (1H, dd, J = 4.2, 2.3 Hz), 4.67-4.59 (1H, m), 2.83 (1H, d, J = 14.5 Hz), 2.47 (1H, t, J = 3.8 Hz), 2.43-2.37 (1H, m), 2.27-2.20 (1H, m), 2.00 (3H, s), 1.26 (6H, d, J = 6.1 Hz); [M + H]+ = 410. |
| 70 | | ¹H-NMR (DMSO-D₆) δ: 12.54 (1H, br s), 7.95 (1H, s), 7.65 (1H, d, J = 2.3 Hz), 7.52 (1H, dd, J = 9.2, 2.3 Hz), 7.35-7.34 (2H, m), 6.87 (1H, t, J = 2.3 Hz), 6.31 (1H, dd, J = 3.8, 2.3 Hz), 2.83 (1H, d, J = 12.2 Hz), 2.83 (3H, s), 2.47-2.36 (2H, m), 2.31-2.21 (1H, m), 2.01 (3H, s); [M + H]+ = 450. |
| 71 | | ¹H-NMR (DMSO-D₆) δ: 12.61 (1H, br s), 8.10 (1H, s), 7.99 (1H, d, J = 2.3 Hz), 7.64-7.60 (2H, m), 7.33 (1H, t, J = 1.5 Hz), 6.88 (1H, dd, J = 3.8, 1.5 Hz), 6.32 (1H, dd, J = 4.2, 2.7 Hz), 2.83 (1H, d, J = 13.8 Hz), 2.50-2.38 (2H, m), 2.28-2.21 (1H, m), 2.02 (3H, s); [M + H]+ = 470. |

TABLE 2-12

| | | |
|---|---|---|
| 72 |  | ¹H-NMR (DMSO-D₆) δ: 12.57 (1H, br s), 8.09 (1H, s), 7.62-7.60 (2H, m), 7.54 (1H, t, J = 8.4 Hz), 7.34 (1H, t, J = 2.3 Hz), 7.30 (1H, d, J = 8.4 Hz), 6.88 (1H, dd, J = 3.8, 1.5 Hz), 6.32 (1H, t, J = 3.8 Hz), 2.83 (1H, d, J = 13.0 Hz), 2.50-2.38 (2H, m), 2.28-2.21 (1H, m), 2.02 (3H, s); [M + H]+ = 436. |

TABLE 2-12-continued

| | | |
|---|---|---|
| 73 | | ¹H-NMR (DMSO-D₆) δ: 10.62 (1H, br s), 7.78 (2H, d, J = 9.1 Hz), 7.73 (2H, d, J = 9.1 Hz), 7.68 (2H, d, J = 9.1 Hz), 7.43 (2H, d, J = 9.1 Hz), 7.20 (1H, t, J = 1.8 Hz), 6.85 (1H, dd, J = 3.9, 1.8 Hz), 6.27 (1H, dd, J = 3.9, 2.4 Hz), 5.23 (1H, t, J = 4.2 Hz), 2.60-2.43 (4H, m); [M + H]+ = 415. |
| 74 | | ¹H-NMR (DMSO-D₆) δ: 10.57 (1H, br s), 7.73 (1H, d, J = 1.5 Hz), 7.71-7.65 (4H, m), 7.51-7.46 (2H, m), 7.20 (1H, t, J = 1.9 Hz), 6.85 (1H, dd, J = 3.8, 1.5 Hz), 6.27 (1H, dd, J = 3.8, 1.9 Hz), 5.21 (1H, t, J = 4.6 Hz), 2.59-2.44 (4H, m); [M + H]+ = 411. |
| 75 | | ¹H-NMR (DMSO-D₆) δ: 10.55 (1H, s), 7.72-7.68 (4H, m), 7.67-7.63 (2H, m), 7.35 (1H, t, J = 74.2 Hz), 7.26-7.23 (2H, m), 7.19 (1H, t, J = 1.9 Hz), 6.84 (1H, dd, J = 3.8, 1.5 Hz), 6.27 (1H, dd, J = 3.8, 1.9 Hz), 5.21 (1H, t, J = 4.2 Hz), 2.60-2.44 (4H, m); [M + H]+ = 397. |
| 76 | | ¹H-NMR (DMSO-D₆) δ: 10.62 (1H, br s), 7.98 (1H, d, J = 2.3 Hz), 7.77-7.71 (5H, m), 7.62 (1H, dd, J = 8.0, 2.3 Hz), 7.20 (1H, t, J = 1.9 Hz), 6.85 (1H, dd, J = 3.8, 1.5 Hz), 6.27 (1H, dd, J = 3.8, 1.9 Hz), 5.22 (1H, t, J = 3.8 Hz), 2.59-2.54 (1H, m), 2.51-2.44 (3H, m); [M + H]+ = 449. |
| 77 | | ¹H-NMR (DMSO-D₆) δ: 10.75 (1H, s), 7.77 (2H, d, J = 9.1 Hz), 7.71 (2H, d, J = 9.1 Hz), 7.68 (2H, d, J = 9.1 Hz), 7.44 (2H, d, J = 9.1 Hz), 6.92 (1H, d, J = 4.2 Hz), 6.48 (1H, d, J = 4.2 Hz), 5.27 (1H, d, J = 3.6 Hz), 2.72-2.66 (1H, m), 2.56-2.45 (3H, m); [M + H]+ = 494. |
| 78 | | ¹H-NMR (CDCl₃) δ: 8.31 (1H, t, J = 8.2 Hz), 7.53 (2H, d, J = 8.2 Hz), 7.35-7.17 (6H, m), 7.04 (1H, s), 6.52 (1H, s), 5.06 (1H, s), 2.93-2.88 (1H, m), 2.68-2.61 (3H, m); [M + H]+ = 433. |

TABLE 2-13

| | | |
|---|---|---|
| 79 | | ¹H-NMR (DMSO-D₆) δ: 10.38 (1H, s), 8.06 (1H, d, J = 2.4 Hz), 8.02 (1H, t, J = 8.2 Hz), 7.82 (1H, dd, J = 8.5, 2.4 Hz), 7.78 (1H, dd, J = 12.2, 2.4 Hz), 7.64 (1H, dd, J = 8.5, 1.8 Hz), 7.60 (1H, dd, J = 8.5, 1.8 Hz), 7.20 (1H, t, J = 2.4 Hz), 6.84 (1H, dd, J = 4.0, 1.5 Hz), 6.28 (1H, dd, J = 4.0, 2.4 Hz), 5.39 (1H, t, J = 3.7 Hz), 2.57-2.44 (4H, m); [M + H]+ = 467. |
| 80 | | ¹H-NMR (DMSO-D₆) δ: 10.29 (1H, s), 7.93 (1H, t, J = 8.5 Hz), 7.63-7.59 (3H, m), 7.48 (1H, dd, J = 8.5, 1.8 Hz), 7.20 (1H, t, J = 2.1 Hz), 7.05 (2H, d, J = 8.5 Hz), 6.84 (1H, dd, J = 4.2, 1.5 Hz), 6.27 (1H, dd, J = 4.2, 2.1 Hz), 5.37 (1H, t, J = 3.9 Hz), 2.57-2.44 (4H, m), 1.33 (9H, s); [M + H]+ = 421 |

TABLE 2-13-continued

| | | |
|---|---|---|
| 81 | | ¹H-NMR (DMSO-D₆) δ: 9.81 (1H, s), 7.78 (2H, d, J = 8.5 Hz), 7.58 (1H, s), 7.56-7.49 (2H, m), 7.44 (2H, d, J = 8.5 Hz), 7.21 (1H, t, J = 2.1 Hz), 6.84 (1H, dd, J = 4.2, 1.8 Hz), 6.29 (1H, dd, J = 4.2, 2.1 Hz), 5.31 (1H, t, J = 3.9 Hz), 2.60-2.46 (4H, m), 2.30 (3H, s); [M + H]+ = 429. |
| 82 | | ¹H-NMR (DMSO-D₆) δ: 11.15 (1H, s), 8.73 (1H, dd, J = 2.1, 0.9 Hz), 8.16 (1H, dd, J = 8.5, 2.4 Hz), 8.13 (1H, d, J = 8.5 Hz), 7.87-7.86 (2H, m), 7.48 (2H, d, J = 7.9 Hz), 7.22 (1H, dd, J = 2.4, 1.2 Hz), 6.85 (1H, dd, J = 4.0, 1.2 Hz), 6.27 (1H, dd, J = 4.0, 2.4 Hz), 5.36 (1H, t, J = 3.7 Hz), 2.56-2.41 (4H, m); [M + H]+ = 416. |
| 83 | | ¹H-NMR (DMSO-D₆) δ: 10.77 (1H, s), 8.58 (1H, d, J = 1.8 Hz), 8.20 (2H, d, J = 9.1 Hz), 8.05 (1H, d, J = 9.1 Hz), 7.63 (1H, dd, J = 9.1, 1.8 Hz), 7.57 (2H, d, J = 9.1 Hz), 7.22 (1H, t, J = 2.1 Hz), 6.85 (1H, dd, J = 3.9, 1.5 Hz), 6.28 (1H, dd, J = 3.9, 2.1 Hz), 5.26 (1H, t, J = 4.2 Hz), 2.62-2.45 (4H, m); [M + H]+ = 472. |
| 84 | | ¹H-NMR (DMSO-D₆) δ: 12.76 (1H, br s), 7.54 (1H, d, J = 1.8 Hz), 7.48 (1H, d, J = 8.5 Hz), 7.26 (1H, dd, J = 8.5, 1.8 Hz), 7.21 (1H, t, J = 2.4 Hz), 6.85 (1H, dd, J = 4.0, 1.5 Hz), 6.27 (1H, dd, J = 4.0, 2.4 Hz), 5.33 (1H, t, J = 4.3 Hz), 2.59-2.54 (2H, m), 2.43-2.40 (2H, m), 2.35 (3H, s); [M + H]+ = 432. |

TABLE 2-14

| | | |
|---|---|---|
| 85 | | ¹H-NMR (DMSO-D₆) δ: 12.70 (1H, br s), 7.48-7.47 (2H, m), 7.43-7.40 (2H, m), 7.37-7.29 (3H, m), 7.20-7.17 (2H, m), 6.85 (1H, dd, J = 4.0, 1.5 Hz), 6.27 (1H, dd, J = 4.0, 2.0 Hz), 5.32 (1H, t, J = 4.0 Hz), 5.22 (2H, s), 2.56-2.54 (2H, m), 2.44-2.39 (2H, m), 2.34 (3H, s); [M + H]+ = 476. |
| 86 | | ¹H-NMR (DMSO-D₆) δ: 12.64 (1H, br s), 7.34-7.33 (2H, m), 7.20 (1H, t, J = 2.1 Hz), 7.01-6.99 (2H, m), 6.85 (1H, dd, J = 4.0, 1.5 Hz), 6.27 (1H, dd, J = 4.0, 2.1 Hz), 5.32 (1H, t, J = 4.0 Hz), 3.77 (2H, d, J = 6.7 Hz), 2.57-2.53 (2H, m), 2.43-2.41 (2H, m), 2.33 (3H, s), 2.07-1.97 (1H, m), 0.98 (6H, d, J = 6.7 Hz); [M + H]+ = 424. |
| 87 | | ¹H-NMR (DMSO-D₆) δ: 12.77 (1H, br s), 8.18 (1H, d, J = 2.0 Hz), 7.98 (1H, d, J = 2.0 Hz), 7.21 (1H, t, J = 2.1 Hz), 6.85 (1H, dd, J = 4.0, 1.5 Hz), 6.27 (1H, dd, J = 4.0, 2.1 Hz), 5.34 (1H, t, J = 4.0 Hz), 4.15 (2H, d, J = 6.7 Hz), 2.59-2.54 (2H, m), 2.44-2.39 (2H, m), 2.33 (3H, s), 2.12-2.02 (1H, m), 0.99 (6H, d, J = 6.7 Hz); [M + H]+ = 460. |

TABLE 2-14-continued

| 88 | 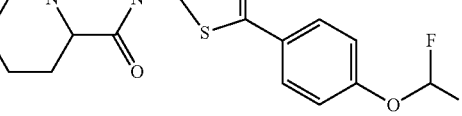 | ¹H-NMR (DMSO-D₆) δ: 12.68 (1H, br s), 7.41-7.40 (2H, m), 7.20 (1H, t, J = 2.4 Hz), 7.14-7.13 (2H, m), 6.85 (1H, dd, J = 4.0, 1.5 Hz), 6.27 (1H, dd, J = 4.0, 2.4 Hz), 5.33 (1H, t, J = 4.3 Hz), 4.80 (2H, q, J = 8.7 Hz), 2.58-2.51 (2H, m), 2.44-2.40 (2H, m), 2.34 (3H, s); [M + H]+ = 450. |
| 89 | | ¹H-NMR (DMSO-D₆) δ: 12.75 (1H, br s), 7.47 (1H, s), 7.38 (2H, s), 7.20 (1H, t, J = 2.0 Hz), 6.85 (1H, dd, J = 4.0, 1.5 Hz), 6.27 (1H, dd, J = 4.0, 2.0 Hz), 5.32 (1H, t, J = 4.0 Hz), 2.58-2.51 (2H, m), 2.43-2.41 (2H, m), 2.37 (3H, s), 2.31 (3H, s); [M + H]+ = 450. |
| 90 | | ¹H-NMR (DMSO-D₆) δ: 12.60 (1H, br s), 7.18 (1H, t, J = 2.1 Hz), 6.84 (1H, dd, J = 4.0, 1.5 Hz), 6.26 (1H, dd, J = 4.0, 2.1 Hz), 5.84 (1H, br s), 5.29 (1H, t, J = 4.3 Hz), 3.97 (2H, br s), 3.50 (2H, t, J = 5.5 Hz), 2.54-2.45 (2H, m), 2.42-2.33 (4H, m), 2.30 (3H, s), 1.42 (9H, s); [M + H]+ = 457. |

TABLE 2-15

| 91 | 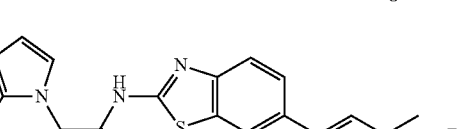 | ¹H-NMR (DMSO-D₆) δ: 12.72 (1H, br s), 7.52-7.48 (2H, m), 7.28 (1H, t, J = 74.5 Hz), 7.27-7.24 (2H, m), 7.21 (1H, t, J = 2.1 Hz), 6.85 (1H, dd, J = 4.0, 1.5 Hz), 6.27 (1H, dd, J = 4.0, 2.1 Hz), 5.34 (1H, t, J = 4.0 Hz), 2.58-2.52 (2H, m), 2.44-2.40 (2H, m), 2.35 (3H, s); [M + H]+ = 418. |
| 92 |  | ¹H-NMR (DMSO-D₆) δ: 12.98 (1H, br s), 8.35 (1H, d, J = 1.8 Hz), 7.86 (1H, d, J = 8.5 Hz), 7.79-7.77 (2H, m), 7.67 (1H, dd, J = 8.5, 2.4 Hz), 7.40 (1H, dd, J = 8.5, 1.2 Hz), 7.27 (1H, t, J = 2.1 Hz), 6.87 (1H, dd, J = 4.0, 1.5 Hz), 6.29 (1H, dd, J = 4.0, 2.1 Hz), 5.43 (1H, t, J = 4.0 Hz), 2.63-2.57 (2H, m), 2.45-2.42 (2H, m), 2.36 (3H, s); [M + H]+ = 486. |
| 93 | | ¹H-NMR (DMSO-D₆) δ: 12.98 (1H, br s), 8.35 (1H, d, J = 1.8 Hz), 7.85 (1H, d, J = 8.5 Hz), 7.78-7.76 (3H, m), 7.55-7.51 (2H, m), 7.27 (1H, t, J = 2.1 Hz), 6.87 (1H, dd, J = 4.0, 1.5 Hz), 6.29 (1H, dd, J = 4.0, 2.1 Hz), 5.42 (1H, t, J = 4.3 Hz), 2.61-2.57 (2H, m), 2.46-2.41 (2H, m); [M + H]+ = 422. |
| 94 | 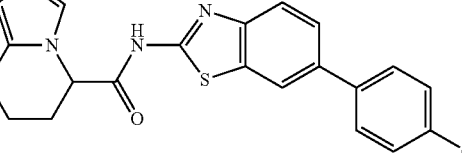 | ¹H-NMR (DMSO-D₆) δ: 12.97 (1H, br s), 8.30 (1H, d, J = 1.8 Hz), 7.83 (1H, d, J = 8.5 Hz), 7.79-7.72 (3H, m), 7.30 (2H, t, J = 8.5 Hz), 7.26 (1H, t, J = 2.1 Hz), 6.87 (1H, dd, J = 4.0, 1.5 Hz), 6.29 (1H, dd, J = 4.0, 2.1 Hz), 5.40 (1H, t, J = 4.3 Hz), 2.62-2.56 (2H, m), 2.47-2.42 (2H, m); [M + H]+ = 406. |

TABLE 2-15-continued

| 95 | (structure) | ¹H-NMR (DMSO-D₆) δ: 12.91 (1H, s), 8.15 (1H, s), 7.82-7.74 (6H, m), 7.69 (1H, t, J = 6.7 Hz), 7.58-7.57 (2H, m), 7.24 (1H, br s), 6.87 (1H, d, J = 3.6 Hz), 6.29 (1H, t, J = 3.6 Hz), 5.39 (1H, t, J = 3.9 Hz), 2.63-2.53 (2H, m), 2.45-2.43 (2H, m); [M + H]+ = 442. |
| --- | --- | --- |
| 96 | (structure) | ¹H-NMR (DMSO-D₆) δ: 12.85 (1H, br s), 7.51 (2H, d, J = 8.5 Hz), 7.46 (2H, d, J = 8.5 Hz), 7.20 (1H, s), 6.85 (1H, d, J = 3.6 Hz), 6.27 (1H, t, J = 2.7 Hz), 5.34 (1H, t, J = 4.2 Hz), 3.11-3.04 (1H, m), 2.57-2.55 (2H, br m), 2.44-2.42 (2H, br m), 1.23 (6H, d, J = 6.7 Hz); [M + H]+ = 464. |

TABLE 2-16

| 97 | (structure) | ¹H-NMR (DMSO-D₆) δ: 12.68 (1H, br s), 7.48 (1H, s), 7.21 (1H, t, J = 1.5 Hz), 6.85 (1H, dd, J = 3.9, 1.5 Hz), 6.27 (1H, dd, J = 3.9, 2.4 Hz), 5.98-5.94 (1H, br m), 5.33 (1H, t, J = 4.2 Hz), 4.18 (1H, br s), 4.05 (1H, br s), 3.69-3.63 (2H, m), 2.99-2.81 (1H, m), 2.59-2.49 (4H, m), 2.44-2.39 (2H, br m), 1.01 (3H, d, J = 6.7 Hz), 0.98 (3H, d, J = 6.7 Hz); [M + H]+ = 413. |
| --- | --- | --- |
| 98 | (structure) | ¹H-NMR (DMSO-D₆) δ: 12.67 (1H, br s), 7.48 (1H, s), 7.21 (1H, t, J = 1.8 Hz), 6.85 (1H, dd, J = 3.9, 1.8 Hz), 6.27 (1H, dd, J = 3.9, 2.7 Hz), 6.18 (1H, d, J = 7.3 Hz), 5.94 (1H, t, J = 3.6 Hz), 5.33 (1H, t, J = 4.2 Hz), 3.94-3.90 (2H, br m), 3.80-3.72 (1H, m), 3.49 (2H, t, J = 5.7 Hz), 2.59-2.49 (2H, m), 2.44-2.38 (4H, br m), 1.05 (6H, d, J = 6.0 Hz); [M + H]+ = 428. |
| 99 | (structure) | ¹H-NMR (CDCl₃) δ: 8.82 (1H, br s), 7.49-7.45 (2H, m), 7.18 (1H, dd, J = 4.2, 1.2 Hz), 7.01-6.96 (3H, m), 6.49 (1H, dd, J = 4.2, 2.4 Hz), 5.16 (1H, dd, J = 5.1, 2.7 Hz), 4.40 (2H, q, J = 8.1 Hz), 3.79 (3H, s), 2.88-2.82 (1H, m), 2.69-2.51 (3H, m); [M + H]+ = 494. |
| 100 | (structure) | ¹H-NMR (CDCl₃) δ: 8.80 (1H, br s), 7.42-7.39 (2H, m), 7.18 (1H, dd, J = 4.2, 1.2 Hz), 7.04-7.02 (2H, m), 6.97 (1H, t, J = 2.4 Hz), 6.48 (1H, dd, J = 4.2, 2.4 Hz), 5.16 (1H, dd, J = 4.8, 2.4 Hz), 3.78 (3H, s), 2.87-2.82 (1H, m), 2.69-2.52 (3H, m), 1.40 (9H, s); [M + H]+ = 468. |
| 101a First peak: Optically active form of compound of Example 35 | | HPLC measurement conditions Column: YMC CHIRAL ART Cellulose-SC (5um), 250 × 4.6 mm I.D., Column temperature: 25° C., Flow rate: 0.5 ml/min, |

TABLE 2-16-continued

| | |
|---|---|
| 101b Second peak: Optically active form of compound of Example 35 | Mobile phase: n-hexane/ethanol = 40/60, Measurement wavelength: 288 nm Retention time: tR = 13.6 min HPLC measurement conditions Column: YMC CHIRAL ART Cellulose-SC (5um), 250 × 4.6 mm I.D., Column temperature: 25° C., Flow rate: 0.5 ml/min, Mobile phase: n-hexane/ethanol = 40/60, Measurement wavelength: 288 nm Retention time: tR = 23.4 min |

Experimental Example 1

Evaluation of Effect to Promote Differentiation from Human iPS Cells into Insulin-Producing Cells The evaluation system of the effect (efficacy) to promote differentiation from human iPS cells into insulin-producing cells was constructed with reference to known information (Non Patent Document 6). Further, the medium used in each differentiation stage was also produced with reference to known information (differentiation media A to E (Media A to E) described in Non Patent Document 6 were used respectively for stages 1 to 5; however, a medium free from GLP-1 receptor agonist and nicotinamide was used as differentiation medium E).

In order to evaluate the efficacy of each compound, the compound of Example 1 was used as a positive control, and dimethylsulfoxide (DMSO) (SIGMA, D2650) with a final concentration of 0.1% was used as a control untreated with compounds. Each compound was dissolved in DMSO, and two types of compound solutions were prepared so as to have final concentrations of 2 µM and 10 µM after the compound was added to the medium. In the following evaluation, the compound solutions were added to the medium to 0.1% that is the final concentration of DMSO. First, induction from human iPS cell Toe strain (National Institutes of Biomedical Innovation, Health and Nutrition) into cells on day 7 of culture (2 days after replacement with differentiation medium C (cells in the differentiation process from FOXA2-positive primitive gut tube cells into PDX1-positive pancreatic progenitor cells)) was performed according to the method of Non Patent Document 6 for "inducing differentiation from human iPS cells into pancreatic β cells", and the cells were collected and thereafter stored in liquid nitrogen using Bambanker (NIPPON Genetics Co, Ltd.) at $1\times10^7$ cells/mL/tube, to produce a cell stock for evaluation. The cell stock was dissolved at the start of the evaluation of efficacy, suspended in differentiation medium C for stage 3 (DMEM high glucose (Life technologies, 11965092), 0.25 µM SANT-1, 0.1 µM LDN193189 (Stemgent, 04-0074), 10 µM SB431542, 2 µM Retinoic acid (Stemgent, 04-0021), 1% B27 serum free supplement (Life technologies, 17504044) and thereafter seeded in a 96-well plate (Corning, #3340) coated with Synthemax II (Corning, #5656) at $1\times10^5$ cells/well. After culturing for 2 days, the medium was removed, and new differentiation medium C for stage 3 with the compound or only DMSO added was added thereto at 100 µL/well. After culturing for 2 days, the medium was removed, and new differentiation medium D for stage 4 (DMEM high glucose, 0.1 µM LDN193189, 5 µM TGF-β type I receptor kinase inhibitor II (Calbiochem 616452), 0.3 µM (-)-indolactam V (Enzo life science ALX-420-011-C300), 1% B27 serum free supplement) with the compound or only DMSO added was added thereto at 100 µL/well. After culturing for 2 to 3 days, the medium was removed, and new differentiation medium E for stage 5 (GLP-1 receptor agonist and nicotinamide-free; Knockout DMEM/F-20 (Life technologies, 12660012), 1% B27 serum free supplement) with the compound or only DMSO added was added thereto at 200 µL/well. After culturing for 2 days, the medium was removed, and a 4% paraformaldehyde phosphorus acid buffer (Wako, 163-20145) was added thereto at 150 µL/well and left standing for 30 to 60 minutes at room temperature to fix the cells. A phosphorus acid buffer (PBS) (Takara, T9181) containing 1% Triton X-100 (Sigma, T8787) was left standing for 15 minutes at room temperature, then washed with PBS-T (Takara, T9183), and was blocked for 1 hour using 20% Blocking One (Nacalai tesque, Tokyo, Japan) diluted with PBS-T at room temperature. After the removal of Blocking One, guinea pig anti-insulin antibody (Abcam, ab7842) diluted 200-fold with 20% Blocking One was added thereto at 50 µL/well, followed by standing at 4° C. overnight. After washing with PBS-T 3 times, Alexa Fluor 548-labeled anti-guinea pig antibody (Life Technologies, A11075) diluted 1000-fold with 20% Blocking One and 6-diamidino-2-phenylindole (DAPI) (Roche Diagnostics, Basel, Switzerland) were added thereto, followed by standing at room temperature for 2 hours. After washing with PBS-T 3 times, the fluorescence images of the cells were analyzed.

The cell images were captured using a high-content imaging system Opera Phenix or Operetta (PerkinElmer). Further, the total number of insulin-positive cells and DAPI-positive cells was measured by analysis using Harmony (PerkinElmer) to calculate the ratio of the number of the insulin-positive cells with respect to the total number of the cells (insulin-positive cell rate). The compound of Example 1 was used as a positive control, and DMSO with a final concentration of 0.1% was used as a control untreated with compounds. The increment in insulin-positive cell rate (average insulin-positive cell rate of 30 cases: 13%) of 10 µM of the compound of Example 1 from the control untreated with compounds (average insulin-positive cell rate of 30 cases: 4.9%) was taken as 100%. The increment in insulin-positive cell rate of each compound at each concentration was converted into a percentage (%) based on the above, to obtain an activity value. The primary evaluation of the compound including the positive control was performed for each compound at two concentrations of 2 µM and 10 µM using a plurality of wells. The activity intensity was determined by comparing the sum of activity values at the two concentrations with the positive control. The case where the sum of activity values at the two concentrations was obviously higher than the control untreated with compounds while being lower than the positive control was expressed as +, the case where the sum was equivalent to the positive control was expressed as ++, and the case where the sum was higher than the positive control was expressed as +++. Compounds having a weak activity intensity were evaluated again at a concentration of 0.4, 2, 5 or 10 μM using a plurality of wells, and compounds obviously exhibiting a higher activity value than the control untreated with compounds or exhibiting an activity value of 15% or more at any concentration and exhibiting a significant difference ($P<0.05$) in the t test as compared with the control untreated with compounds were determined to be effective. Compounds exhibiting comparatively strong efficacy were subjected to the secondary evaluation at a concentration from 0.01 to 10 μM using a plurality of wells, in order to investigate the concentration-dependent effect, to calculate EC50 (when the efficacy of 10 μM of the compound of Example 1 was taken as 100%, the concentration of the compound at which the efficacy corresponding to 50% thereof can be exerted) using Sigma Plot (Systat Software).

Table 3 and Table 4 show the results of Experimental Example 1.

TABLE 3

| Example No. | Activity |
| --- | --- |
| 1 | ++ |
| 2 | ++ |
| 3 | + |
| 4 | ++ |
| 5 | + |
| 6 | + |
| 7 | + |
| 8 | ++ |
| 9 | +++ |
| 10a | +++ |
| 10b | +++ |
| 11 | +++ |
| 12 | ++ |
| 13 | ++ |
| 14 | + |
| 15 | + |
| 16 | ++ |
| 17 | ++ |
| 18 | ++ |
| 19 | ++ |
| 20 | ++ |
| 21 | +++ |
| 22 | +++ |
| 23 | + |
| 24 | + |
| 25 | +++ |
| 26 | ++ |
| 27 | ++ |
| 28 | +++ |
| 29 | +++ |
| 30 | +++ |
| 31 | + |
| 32 | +++ |
| 33 | +++ |
| 34 | ++ |
| 35 | +++ |
| 36 | +++ |
| 37 | + |
| 38 | +++ |
| 39 | +++ |
| 40 | +++ |
| 41 | + |
| 42 | + |
| 43 | +++ |
| 44 | + |
| 45 | +++ |
| 46 | +++ |
| 47 | ++ |
| 48 | + |
| 49 | +++ |
| 50 | + |
| 51 | +++ |
| 52 | +++ |
| 53 | ++ |
| 54 | + |
| 55 | + |
| 56 | ++ |
| 57 | + |
| 58 | ++ |
| 59 | +++ |
| 60 | ++ |
| 61 | + |
| 62 | +++ |
| 63 | +++ |
| 64 | ++ |
| 65 | +++ |
| 66 | ++ |
| 67 | ++ |
| 68 | ++ |
| 69 | ++ |
| 70 | ++ |
| 71 | +++ |
| 72 | +++ |
| 73 | + |
| 74 | + |
| 75 | + |
| 76 | + |
| 77 | + |
| 78 | ++ |
| 79 | + |
| 80 | + |
| 81 | + |
| 82 | + |
| 83 | + |
| 84 | +++ |
| 85 | +++ |
| 86 | +++ |
| 87 | +++ |
| 88 | +++ |
| 89 | +++ |
| 90 | +++ |
| 91 | +++ |
| 92 | +++ |
| 93 | +++ |
| 94 | +++ |
| 95 | +++ |
| 96 | + |
| 97 | ++ |
| 98 | ++ |
| 99 | ++ |
| 100 | + |
| 101a | + |
| 101b | +++ |

TABLE 4

| Example No. | E050 (μM) |
| --- | --- |
| 1 | 5.8 |
| 9 | 0.23 |
| 10a | 1.2 |
| 10b | 0.22 |
| 11 | 0.49 |
| 21 | 0.45 |
| 30 | 1.0 |
| 35 | 0.25 |
| 36 | 0.31 |
| 40 | 0.82 |
| 43 | 0.19 |
| 45 | 0.13 |
| 46 | 0.54 |
| 58 | 1.6 |
| 59 | 0.54 |
| 65 | 1.8 |
| 88 | 0.24 |
| 93 | 0.29 |
| 101b | 0.09 |

It was found from the results of Experimental Example 1 that a compound of the present invention or a salt thereof could efficiently differentiate pluripotent stem cells into insulin-producing cells as compared with the case without addition of the compound.

Experimental Example 2

Evaluation of UCHL1 Activation

The evaluation system of the enzymatic activity of UCHL1 was constructed with reference to known information (the method described in Non Patent Document, PNAS, 110, 3489-3494, 2013). In order to check the establishment of the evaluation system, it was confirmed that the enzymatic activity was inhibited by LDN-57444 (SIGMA, L4170) with a final concentration of 50 µM as a UCHL1 inhibitor. Using dimethylsulfoxide (DMSO) (SIGMA, D2650) as a control untreated with compounds (which will be hereinafter referred to as control), each test compound was dissolved in DMSO in use. DMSO and the test compound solutions were each added to the enzymatic reaction solution to a final concentration of 2%. For measuring the enzymatic activity, UCHL1 protein (R&D, E-340-025) was first dissolved in a buffer {50 mM Tris-HCl (pH7.4), 1 mM dithiothreitol (SIGMA, D9779) and 1 mM EDTA (GIBCO, #15575)} to a final concentration of 25 nM and stored at 4° C. After 40 µl/well of the UCHL1 protein solution was dispensed in a 96-well plate (Thermo Scientific, #236105), DMSO or the test compound solutions were each added to a final concentration of 10 µM, and 10 µl of a fluorescence-labeled substrate ubiquitin-AMC (7-amido-4-methylcoumarin) (Enzo, BML-SE211) was further added thereto at room temperature to a final concentration of 570 nM to prepare an enzymatic reaction solution, thereby starting the enzymatic reaction. The amount of fluorescence (excitation wavelength: 350 nm and fluorescence wavelength: 440 nm) of AMC generated due to hydrolysis of the fluorescence-labeled substrate was measured 10 minutes and 2 hours after the start of the enzymatic reaction, to calculate the increment in amount of fluorescence by subtraction between the two.

The amount of fluorescence of AMC was measured using Envision (PerkinElmer). The increment in amount of fluorescence of the control was taken as 100%, and the increment in amount of fluorescence of each test compound was expressed as a percentage (%) based on this, to obtain an enzymatic activity value.

Enzymatic activity value (%)={(Amount of fluorescence increment of each test compound)/
(Amount of fluorescence increment of control)
}×100

The control experiment and the experiment with addition of the test compound were each conducted with n=6 and n=3, and the average thereof was shown as an enzymatic activity value.

Table 5 shows the results of Experimental Example 2.

TABLE 5

| Subject compound | Enzyme activity (c/o) |
| --- | --- |
| Control | 100 |
| LDN-57444 | 6 |
| Example 9 | 270 |
| Example 88 | 422 |
| Example 101b | 318 |

It was found from the results of Experimental Example 2 that a compound of the present invention or a salt thereof activated UCHL1. Accordingly, a compound of the present invention can be used for treating or preventing diseases (such as neurodegenerative diseases) that can be treated or prevented by activating UCHL1.

Experimental Example 3

Evaluation of Action to Improve Pathological Conditions of Diabetes Using ZDF Rats After repeated oral administration of the compound according to Example 9 to 8 week-old male ZDF disease rats (CHARLES RIVER LABORATORIES JAPAN, INC.) for 4 weeks (from Day 1 to 28), a glucose tolerance test was conducted on Day 28 to investigate the effect to improve the pathological conditions of diabetes. On Day 0, the ZDF disease rats were subjected to measurement of blood sugar, insulin value, and body weight, as needed, and were grouped by multivariable block assignment. The experiments were conducted in a total of 3 groups of 4 male ZDF Lean rats (lean group), a group of 8 ZDF disease rats with a 0.5 w/v % methylcellulose 400 solution (which will be hereinafter referred to as 0.5% MC) administered (vehicle group), and a group of 8 ZDF disease rats with the compound of Example 9 administered (Example 9 group). The compound according to Example 9 was suspended in 0.5% MC and was orally administered 10 mg/kg once a day.

The glucose tolerance test was conducted as follows. That is, fasting was performed from the evening before the glucose tolerance test to the next morning, and the final administration of the compound was performed 30 minutes before the glucose tolerance test. A 50% Otsuka sugar solution (Otsuka Pharmaceutical Co., Ltd.) was orally administered at 4 mL/kg to conduct a glucose load of 2 g/kg. Before the glucose loading and 60 minutes after the glucose loading, blood was collected from the tail vein, and the blood sugar was measured.

The blood sugar was measured using glucose C2-Test Wako (Cat No. 437-90902 for 700 times, available from Wako Pure Chemical Industries, Ltd). Table 6 shows the value obtained by subtracting the measured value before the glucose loading from the measured value 60 minutes after the glucose loading of each individual (Δ blood plasma glucose).

TABLE 6

| Administration group | Δ Plasma glucose (mg/dL) |
| --- | --- |
| Lean | 45.8 |
| Vehicle | 248.2 |
| Example 9 | −275.8 |

It was found from the results of Experimental Example 3 that a compound of the present invention or a salt thereof exhibited an effect to improve the pathological conditions of diabetes. Accordingly, a compound of the present invention or a salt thereof can be used for treating or preventing diabetes in warm-blooded animals (particularly humans).

The invention claimed is:
1. A compound represented by formula (I):

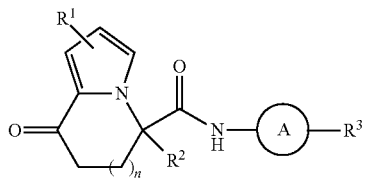
(I)

wherein each substituent is defined as follows:
$R^1$ represents a hydrogen atom, a halogen atom, or a C1-C6 alkyl group;
$R^2$ represents a hydrogen atom or a C1-C6 alkyl group;
$R^3$ represents an aryl group optionally substituted with one to four substituents independently selected from a substituent group α, a C5-C10 cycloalkenyl group optionally substituted with one to four substituents independently selected from a substituent group α, or a heterocyclyl group optionally substituted with one to four substituents independently selected from a substituent group α;
the substituents of substituent group α are selected from the group consisting of a halogen atom, a cyano group, a carboxy group, a C1-C6 alkyl group, a C1-C6 alkoxy group, a halogeno-C1-C6 alkyl group, a halogeno-C1-C6 alkoxy group, a hydroxy C1-C6 alkyl group, a C1-C6 alkoxy C1-C6 alkoxy group, a (C1-C6 alkyl) carbonyl group, a (C1-C6 alkoxy)carbonyl group, a (C1-C6 alkoxy)carbonyloxy group, a phenyl C1-C6 alkoxy group, a non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, a phenoxy group optionally substituted with one to four substituents independently selected from a substituent group β, a phenyl group optionally substituted with one to four substituents independently selected from the substituent group β, and a benzoyl group optionally substituted with one to four substituents independently selected from the substituent group β;
the substituents of substituent group β are selected from the group consisting of a halogen atom, a C1-C6 alkyl group, a C1-C6 alkoxy group, a halogeno-C1-C6 alkyl group, a halogeno-C1-C6 alkoxy group, and a (C1-C6 alkoxy)carbonyl group;
n represents 0 or 1; and
A represents a group represented by any one of formulas (i) to (iv) below:

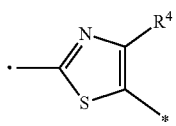
(i)

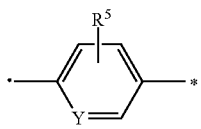
(ii)

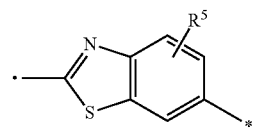
(iii)

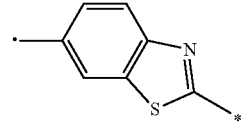
(iv)

wherein each substituent is defined as follows:
• and * each represent a bond, where • is bonded to the nitrogen atom of the amido group of formula (I), and * is bonded to $R^3$;
$R^4$ represents a hydrogen atom, a C1-C6 alkyl group, a halogeno-C1-C6 alkyl group, or a (C1-C6 alkoxy) carbonyl group;
$R^5$ represents a hydrogen atom, a halogen atom, or a C1-C6 alkyl group; and
Y represents N or CH; or a stereoisomer or a salt thereof.
2. A compound according to claim 1, wherein
$R^3$ represents a naphthyl group, a 1,3-benzodioxolyl group, a 2,2-dihalogeno-1,3-benzodioxolyl group, a C5-C10 cycloalkenyl group, a phenyl group optionally substituted with one or two substituents independently selected from a substituent group α1, or a 5- or 6-membered heterocyclyl group optionally substituted with one or two substituents independently selected from the substituent group α1;
the substituents of substituent group α1 are selected from the group consisting of a halogen atom, a cyano group, a carboxy group, a phenoxy group, a benzoyl group, a C1-C6 alkyl group, a C1-C6 alkoxy group, a halogeno-C1-C6 alkyl group, a halogeno-C1-C6 alkoxy group, a hydroxy C1-C6 alkyl group, a C1-C6 alkoxy C1-C6 alkoxy group, a (C1-C6 alkyl)carbonyl group, a (C1-C6 alkoxy)carbonyl group, a (C1-C6 alkoxy)carbonyloxy group, a phenyl C1-C6 alkoxy group, a 5- or 6-membered non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, and a phenyl group optionally substituted with one or two substituents independently selected from a substituent group β1; and
the substituents of substituent group β1 are selected from the group consisting of a halogen atom, a C1-C6 alkyl group, a C1-C6 alkoxy group, and a (C1-C6 alkoxy) carbonyl group; or a stereoisomer or a salt thereof.
3. A compound according to claim 1, wherein
$R^3$ represents a naphthyl group, a 1,3-benzodioxolyl group, a 2,2-dihalogeno-1,3-benzodioxolyl group, a C5-C10 cycloalkenyl group, a phenyl group optionally substituted with one or two substituents independently selected from a substituent group α2, or a 5- or 6-membered heterocyclyl group optionally substituted with one or two substituents independently selected from a substituent group γ2;
the substituents of substituent group α2 are selected from the group consisting of a halogen atom, a cyano group, a carboxy group, a phenoxy group, a benzoyl group, a C1-C6 alkyl group, a C1-C6 alkoxy group, a halogeno-C1-C6 alkyl group, a halogeno-C1-C6 alkoxy group, a hydroxy C1-C6 alkyl group, a C1-C6 alkoxy C1-C6 alkoxy group, a (C1-C6 alkyl)carbonyl group, a (C1-C6 alkoxy)carbonyl group, a (C1-C6 alkoxy)carbonyloxy group, a phenyl C1-C6 alkoxy group, a 5- or 6-membered non-aromatic heterocyclyl group, a carbamoyl group optionally substituted with one or two C1-C6 alkyl groups, a C1-C6 alkoxy group substituted by a carbamoyl group optionally substituted with one or two C1-C6 alkyl groups, a sulfamoyl group substituted with one or two C1-C6 alkyl groups, and a phenyl group optionally substituted with one or two substituents independently selected from a substituent group β2;

the substituents of substituent group β2 are selected from the group consisting of a halogen atom, a C1-C6 alkyl group, and a C1-C6 alkoxy group; and the substituents of substituent group γ2 are selected from the group consisting of a halogen atom, a C1-C6 alkyl group, a C1-C6 alkoxy group, a (C1-C6 alkyl)carbonyl group, and a (C1-C6 alkoxy)carbonyl group; or a stereoisomer or a salt thereof.

4. A compound according to claim 1, wherein $R^3$ represents a naphthyl group, a 1,3-benzodioxolyl group, a 2,2-difluoro-1,3-benzodioxolyl group, a C5-C8 cycloalkene-1-yl group, a phenyl group optionally substituted with one or two substituents independently selected from a substituent group α3, or a 5- or 6-membered heterocyclyl group optionally substituted with one or two substituents independently selected from a substituent group γ3;

the substituents of substituent group α3 are selected from the group consisting of a halogen atom, a cyano group, a carboxy group, a phenoxy group, a benzoyl group, a C1-C4 alkyl group, a C1-C4 alkoxy group, a halogeno-C1-C2 alkyl group, a halogeno-C1-C2 alkoxy group, a hydroxy C1-C4 alkyl group, a C1-C2 alkoxy C1-C2 alkoxy group, a (C1-C4 alkyl)carbonyl group, a (C1-C4 alkoxy)carbonyl group, a (C1-C4 alkoxy)carbonyloxy group, a phenyl C1-C4 alkoxy group, a morpholin-1-yl group, a carbamoyl group optionally substituted with one or two C1-C4 alkyl groups, a C1-C2 alkoxy group substituted by a carbamoyl group optionally substituted with one or two C1-C4 alkyl groups, a sulfamoyl group substituted with one or two C1-C4 alkyl groups, and a phenyl group optionally substituted with one or two substituents independently selected from a substituent group β3;

the substituents of substituent group β3 are selected from the group consisting of a fluorine atom, a chlorine atom, a C1-C4 alkyl group, or a C1-C4 alkoxy group; and the substituents of substituent group γ3 are selected from the group consisting of a halogen atom, a C1-C4 alkyl group, a C1-C4 alkoxy group, a (C1-C4 alkyl)carbonyl group, and a (C1-C4 alkoxy)carbonyl group; or a stereoisomer or a salt thereof.

5. A compound according to claim 1, wherein $R^1$ represents a hydrogen atom, a chlorine atom, or a methyl group, or a stereoisomer or a salt thereof.

6. A compound according to claim 1, wherein $R^2$ represents a hydrogen atom or a methyl group, or a stereoisomer or a salt thereof.

7. A compound according to claim 1, wherein A represents a group represented by formula (i), and $R^4$ represents a hydrogen atom, a C1-C6 alkyl group, a halogeno-C1-C6 alkyl group, or a (C1-C6 alkoxy)carbonyl group, or a stereoisomer or a salt thereof.

8. A compound according to claim 7, wherein $R^4$ represents a hydrogen atom, a methyl group, or a trifluoromethyl group, or a stereoisomer or a salt thereof.

9. A compound according to claim 1, wherein A represents a group represented by formula (ii), and $R^5$ represents a hydrogen atom, a halogen atom, or a C1-C6 alkyl group, or a stereoisomer or a salt thereof.

10. A compound according to claim 9, wherein $R^5$ represents a hydrogen atom, a fluorine atom, or a methyl group, or a stereoisomer or a salt thereof.

11. A compound according to claim 1, wherein A represents a group represented by formula (iii), and $R^5$ represents a hydrogen atom, a fluorine atom, or a methyl group, or a stereoisomer or a salt thereof.

12. A compound according to claim 1, wherein A represents a group represented by formula (iv), or a stereoisomer or a salt thereof.

13. A compound according to claim 1, wherein n represents 1, or a stereoisomer or a salt thereof.

14. A compound according to claim 1, wherein $R^3$ represents a 2,2-difluoro-1,3-benzodioxolyl group, a 1-tert-butoxycarbonyl-3,6-dihydro-2H-pyridine-4-yl group, or a phenyl group optionally substituted with one or two substituents independently selected from the group consisting of a fluorine atom, a chlorine atom, a trifluoromethyl group, a tert-butoxy group, a trifluoromethoxy group, a 2,2,2-trifluoroethoxy group, a benzyloxy group, and a phenoxy group, or a stereoisomer or a salt thereof.

15. A compound according to claim 1, selected from the group consisting of:

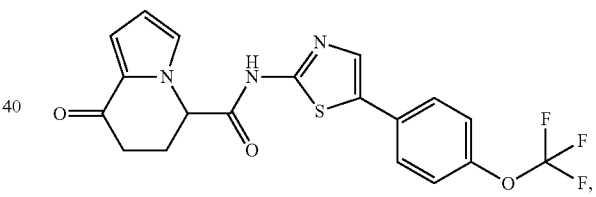

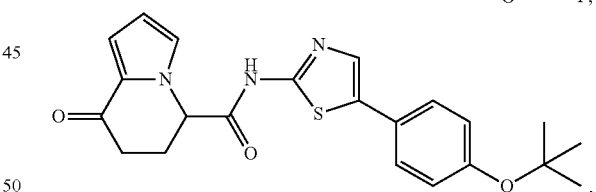

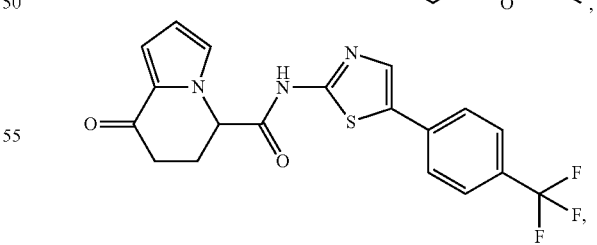

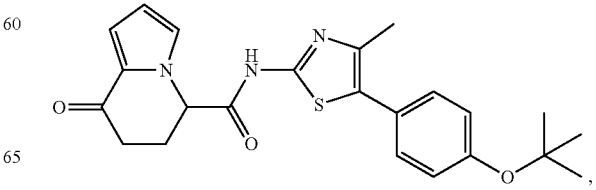

-continued

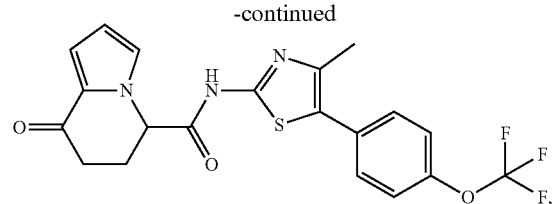

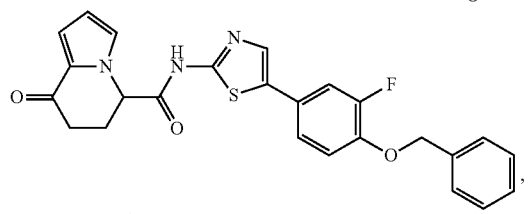, and

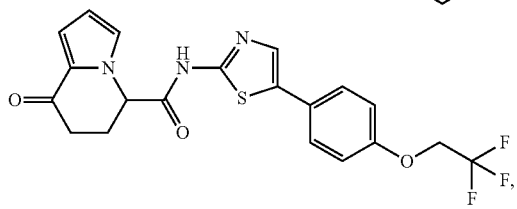

and stereoisomers or salts thereof.

16. A compound according to claim 1, represented by the formula:

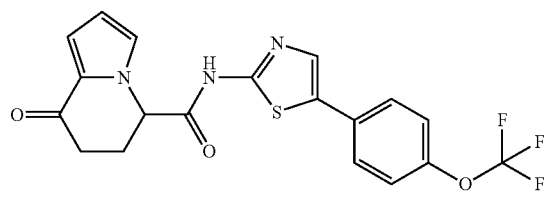 [SMILES: O=C1CCC(C(=O)Nc2ncc(-c3ccc(OC(F)(F)F)cc3)s2)n2cccc21]

or a stereoisomer or a salt thereof.

17. An optical isomer of the compound according to claim 1, represented by the formula:

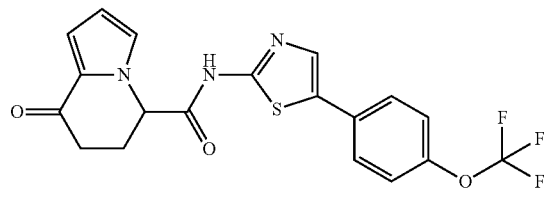 [SMILES: O=C1CCC(C(=O)Nc2ncc(-c3ccc(OC(F)(F)F)cc3)s2)n2cccc21]

or a salt thereof.

18. A compound according to claim 1, represented by the formula:

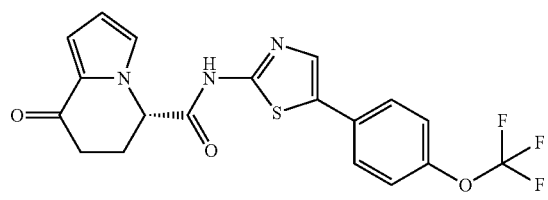 [SMILES: O=C1CC[C@@H](C(=O)Nc2ncc(-c3ccc(OC(F)(F)F)cc3)s2)n2cccc21]

or a salt thereof.

19. A compound according to claim 1, represented by the formula:

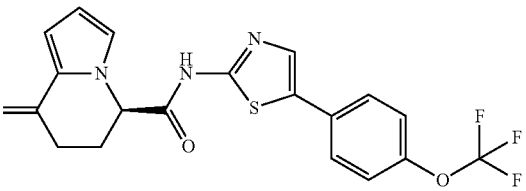

or a salt thereof.

20. A compound according to claim 1, represented by the formula:

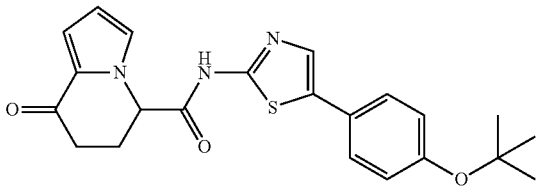 [SMILES: CC(C)(C)Oc1ccc(-c2cnc(NC(=O)C3CCC(=O)c4cccn43)s2)cc1]

or a stereoisomer or a salt thereof.

21. A compound according to claim 1, represented by the formula:

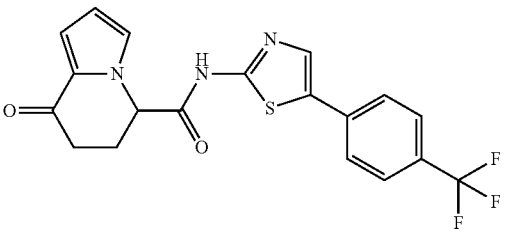 [SMILES: O=C1CCC(C(=O)Nc2ncc(-c3ccc(C(F)(F)F)cc3)s2)n2cccc21]

or a stereoisomer or a salt thereof.

22. A compound according to claim 1, represented by the formula:

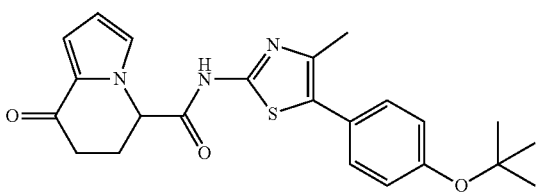 [SMILES: Cc1nc(NC(=O)C2CCC(=O)c3cccn32)sc1-c1ccc(OC(C)(C)C)cc1]

or a stereoisomer or a salt thereof.

23. An optical isomer of the compound according to claim 1, represented by the formula:

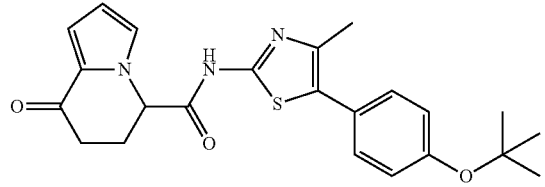 [SMILES: Cc1nc(NC(=O)C2CCC(=O)c3cccn32)sc1-c1ccc(OC(C)(C)C)cc1]

or a salt thereof.

24. A compound according to claim 1, represented by the formula:

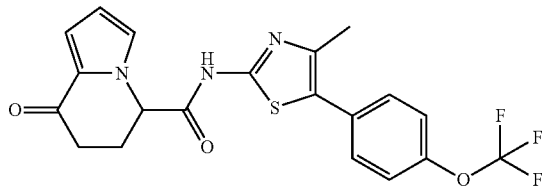 [SMILES: Cc1nc(NC(=O)C2CCC(=O)c3cccn32)sc1-c1ccc(OC(F)(F)F)cc1]

or a stereoisomer or a salt thereof.

25. A compound according to claim 1, represented by the formula:

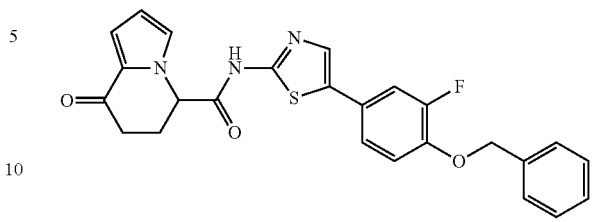

or a stereoisomer or a salt thereof.

26. A compound according to claim 1, represented by the formula:

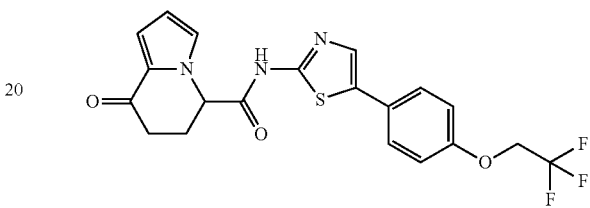

or a stereoisomer or a salt thereof.

27. A pharmaceutical composition comprising a compound according to claim 1, or a stereoisomer or a pharmaceutically acceptable salt thereof, and a pharmaceutically acceptable carrier.

* * * * *